US005352670A

United States Patent [19]

Venot et al.

[11] Patent Number: 5,352,670

[45] Date of Patent: Oct. 4, 1994

[54] METHODS FOR THE ENZYMATIC SYNTHESIS OF ALPHA-SIALYLATED OLIGOSACCHARIDE GLYCOSIDES

[75] Inventors: Andre P. Venot, Agoura Hills, Calif.; Frank M. Unger, Vienna, Austria; Mohammed A. Kashem, Agoura Hills, Calif.; Paul Bird, Edmondton, Canada; M. Abdul Mazid, Novato, Calif.

[73] Assignee: Alberta Research Council, Edmonton, Canada

[21] Appl. No.: 771,007

[22] Filed: Oct. 2, 1991

Related U.S. Application Data

[63] Continuation-in-part of Ser. No. 714,161, Jun. 10, 1991.

[51] Int. Cl.[5] .................... A01N 43/04; A61K 31/715; C12N 11/18; C12P 21/06

[52] U.S. Cl. .......................................... 514/54; 514/57; 435/175; 435/193; 435/230; 435/69.1; 436/63; 436/64

[58] Field of Search ........................ 435/175, 193, 69.1, 435/280, , 230; 514/54, 57; 536/27; 436/64, 63

[56] References Cited

U.S. PATENT DOCUMENTS

| | | | |
|---|---|---|---|
| 4,137,401 | 1/1979 | Lemieux et al. | 536/116 |
| 4,195,174 | 3/1980 | Lemieux et al. | 536/18 |
| 4,727,136 | 2/1988 | Jennings et al. | 530/395 |
| 5,032,505 | 7/1991 | Pierce et al. | 436/64 |
| 5,047,335 | 9/1991 | Paulson et al. | 435/69.1 |
| 5,059,535 | 10/1991 | Mazid et al. | 435/175 |
| 5,070,021 | 12/1991 | Welply | 536/27 |

FOREIGN PATENT DOCUMENTS

| | | |
|---|---|---|
| 0319253 | 6/1989 | European Pat. Off. . |
| 0395217 | 10/1990 | European Pat. Off. . |

OTHER PUBLICATIONS

KG.I Nillson, PCT Int. Appl. WO 89/09275, 5 Oct. 1989.

S. Sabesan, et al., "Combined Chemical and Enzymatic Synthesis of Sialyloligosaccharides and Characterization by 500 MHz $^1H$ and $^{13}C$ n.m.r. Spectroscopy ", *J. Amer. Chem. Soc.*, 108 1986 pp. 2068–2080.

J. Thiem, et al., "Synthesis of the Trisaccharide Neu5Ac–α(2–6)Gal–62 (1–4)GlcNAc by the use of Immobilized Enzymes," *Agnew Chem. Int. Ed. Engl.*, 95 (1982) pp. 1096–1097.

C. Auge, et al., "The Use of Immobilized Glycosyltransferases in the Synthesis of Sialyloligosaccharides," *Carbohydr. Res.*, 200 (1990) pp. 9308–9309.

C. Unverzagt, et al., "High Efficiency Synthesis of Sialyloligosaccharides and Sialylgylcopeptides", *J. Amer. Chem. Soc.*, 112, (1990) pp. 9308–9309.

H. T. de Heij, et al., "Combined Chemical And Enzymatic Synthesis of a Disailylated Tetrasaccharide Analoguous to M and N Blood Group Determinants of Glycophorin A", *J. Carbohydr. Chem., 7 (1988) pp. 209–222.*

M. Palcic et al., "Enzymatic Synthesis of Oligosaccharides Terminating in the Tumor–Associated Sialyl–Lewis Determinant", *Carbohydr. Res.*, 190 (1989) pp. 1–11.

S. Yazawa, et al., "Use of Benzyl 2–Acetamido–2–deoxzy–3–0–(2–O–methyl–β–D–galactosyl)–β–D––glucopyranoside[2′–O–methyllactoN–biose 1βBn] as a Specific Acceptor for GDP–Fucose: N–Acetylglucosamide α(1–4)–L–Fucosyltransferase", *Anal. Biochem.*, 187 (1990) pp. 374–378.

(List continued on next page.)

*Primary Examiner*—Michael G. Wityshyn

*Assistant Examiner*—Louise N. Leary

*Attorney, Agent, or Firm*—Burns, Doane, Swecker & Mathis

[57] ABSTRACT

Disclosed are methods for the enzymatic synthesis of alpha-sialylated oligosaccharide glycosides. Specifically, in the disclosed methods, sialyltransferase is activated to transfer an analogue of sialic acid, employed as its CMP-nucleotide derivative, to an oligosaccharide glycoside. The analogue of sialic acid and the oligosaccharide employed in this method are selected to be compatible with the sialyltransferase employed.

17 Claims, 13 Drawing Sheets

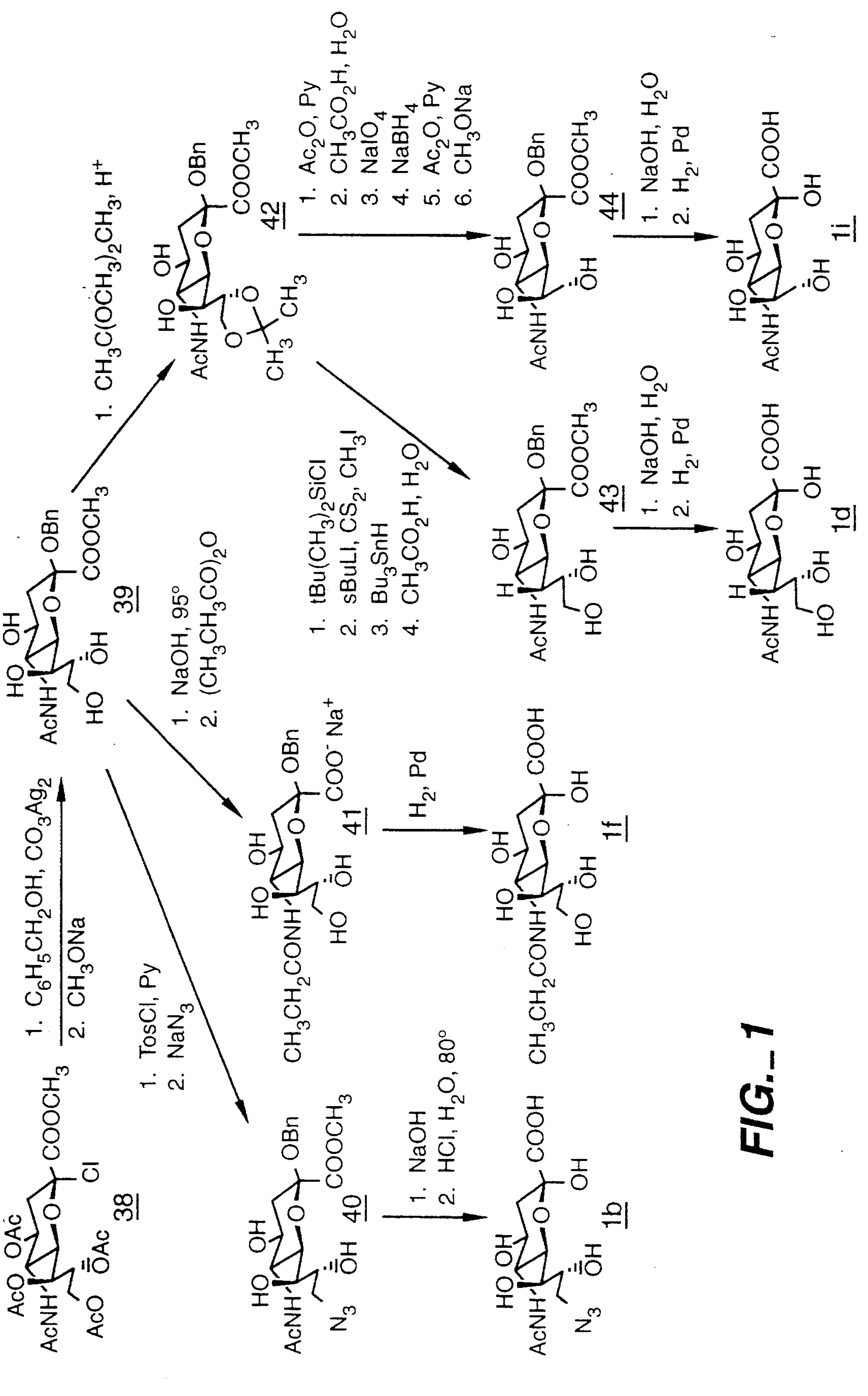
38 39 42 44 1i 43 1d 41 1f 40 1b
FIG._1

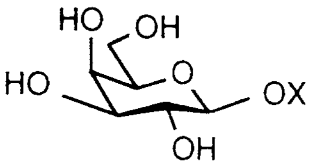
3b, d
| | X |
|---|---|
| 3b | $X_2$ |
| 3d | $X_4$ |
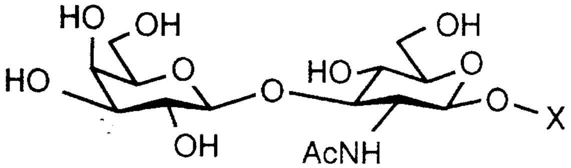
4a, b, c, d
| | X |
|---|---|
| 4a | $X_1$ |
| 4b | $X_2$ |
| 4c | $X_3$ |
| 4d | $X_4$ |
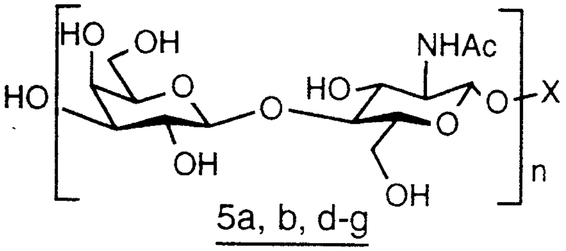
5a, b, d-g
| | n | X |
|---|---|---|
| 5a | 1 | $X_1$ |
| 5b | 1 | $X_2$ |
| 5d | 1 | $X_4$ |
| 5e | 1 | $X_5$ |
| 5f | 1 | $X_6$ |
| 5g | 2 | $X_2$ |
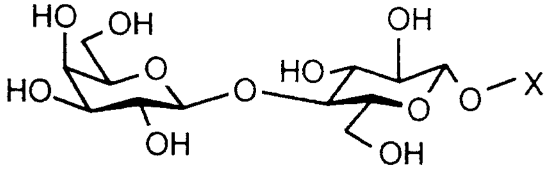
6a
| | X |
|---|---|
| 6a | $X_2$ |
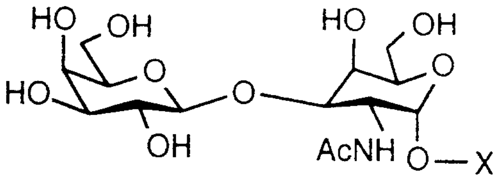
7a
| | X |
|---|---|
| 7a | $X_2$ |
$X_1 = (CH_2)_8CH_2OH$
$X_2 = (CH_2)_8CO_2CH_3$
$X_3 = (CH_2)_5OCH_2CH = CH_2$
$X_4 = OCH_3$
$X_5 =$ 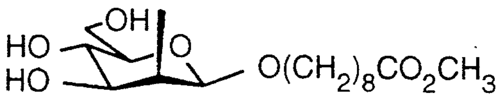
$X_6 =$ 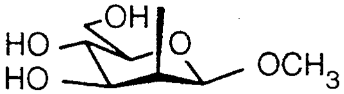
FIG._2

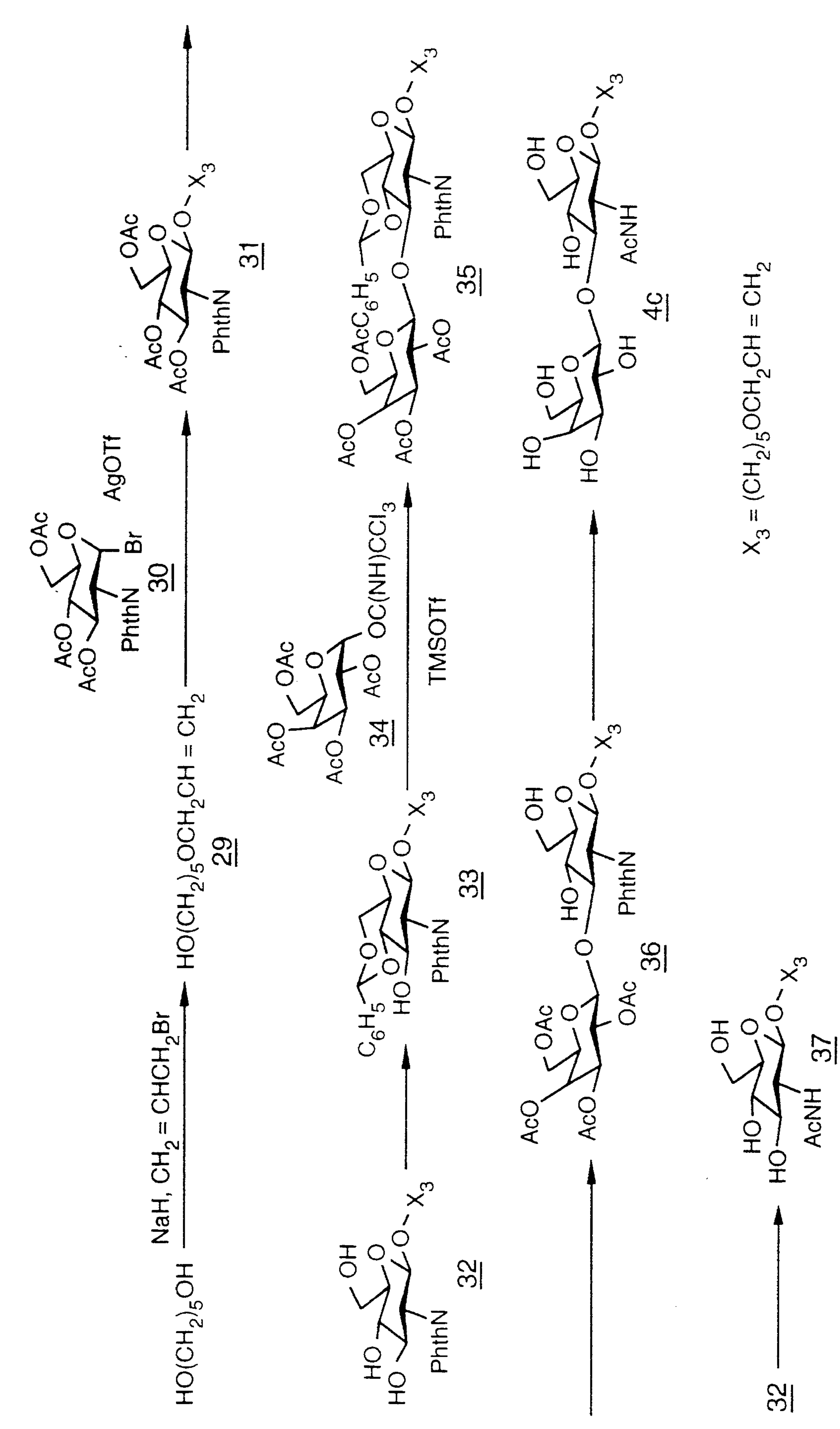
29 30 31 32 33 34 35 36 4c 37
FIG._3

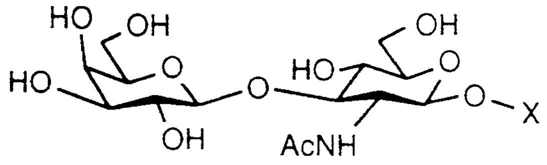
4a, b
CMP – Z
βGal(1→3/4)βGlcNAc α(2→3') ST
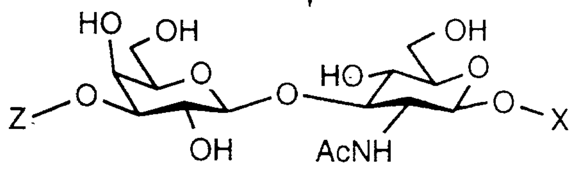
8, 9
α(2-3') Sialylated Lewis^c (Type I) Structures
| Acceptor | X | Sialic Acid (Z) | Product |
|---|---|---|---|
| 4a | $X_1$ | 1a<br>1b<br>1c<br>1d<br>1f | 8a<br>8b<br>8c<br>8d<br>8f |
| 4b | $X_2$ | 1c<br>1e<br>1g<br>1i | 9c<br>9e<br>9g<br>9i |
8b, k, m
GDP — Fuc
βGlcNAc α(1→3/4) Fuc T
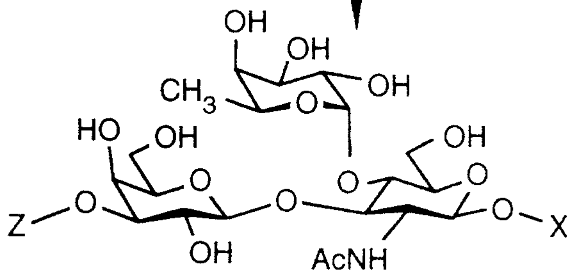
17b, k, m
Sialylated Lewis^a (CA19-9) Structures
| Acceptor | X | Sialic Acid Z | Product |
|---|---|---|---|
| 8b | $X_1$ | 1b | 17b |
| 8k(a) | $X_1$ | 1k | 17k |
| 8m(b) | $X_1$ | 1m | 17m |
(a) See Figure 10
(b) See Figure 9
*FIG._4*

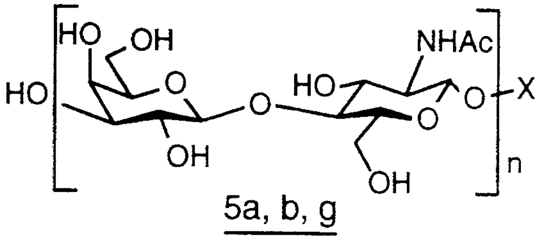
5a, b, g
CMP – Z
βGal(1→3/4)βGlcNAc α(2→3') ST
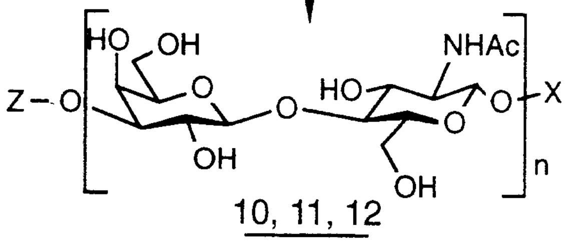
10, 11, 12
α(2-3') Sialylated LacNAc (Type II) Structures
| Acceptor | n | X | Sialic Acid Z | Product |
|---|---|---|---|---|
| 5a | 1 | $X_1$ | 1b | 10b |
| | | | 1c | 10c |
| 5b | 1 | $X_2$ | 1c | 11c |
| 5g | 2 | $X_2$ | 1a | 12a |
11c, 12a
GDP — Fuc
βGlcNAc α(1→3/4) Fuc T
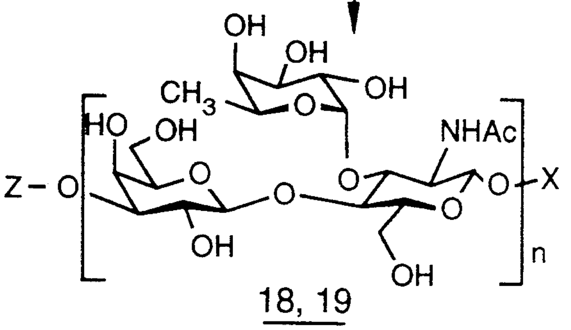
18, 19
Sialylated Lewis Structures
| Acceptor | n | X | Sialic Acid (Z) | Product |
|---|---|---|---|---|
| 11c | 1 | $X_2$ | 1c | 18c |
| 12a | 2 | $X_2$ | 1a | 19a |
*FIG._5*

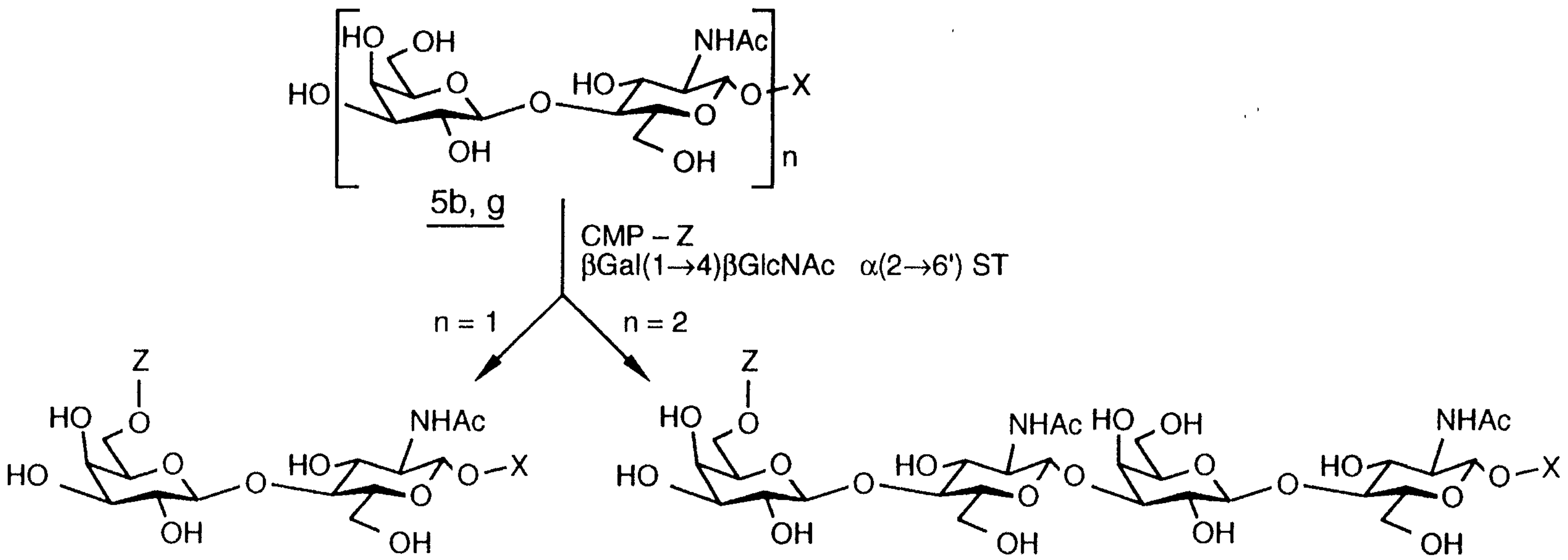
5b, g
13
14
α(2-6) Sialylated LacNAc (Type II) Structures
| Acceptor | n | X | Sialic Acid (Z) | Product |
|---|---|---|---|---|
| 5b | 1 | $X_2$ | 1a | 13a |
| | | | 1b | 13b |
| | | | 1c | 13c |
| | | | 1d | 13d |
| | | | 1e | 13e |
| | | | 1f | 13f |
| | | | 1g | 13g |
| | | | 1h | 13h |
| 5g | 2 | $X_2$ | 1g | 14g |
FIG._6

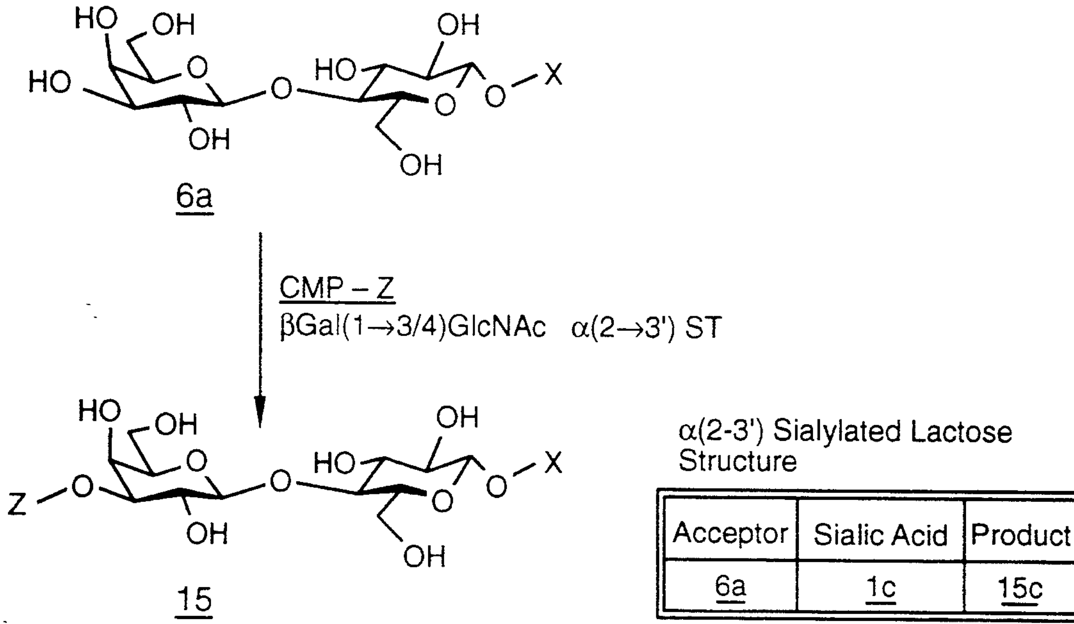
6a
15
α(2-3') Sialylated Lactose Structure
| Acceptor | Sialic Acid | Product |
|---|---|---|
| 6a | 1c | 15c |
FIG._7
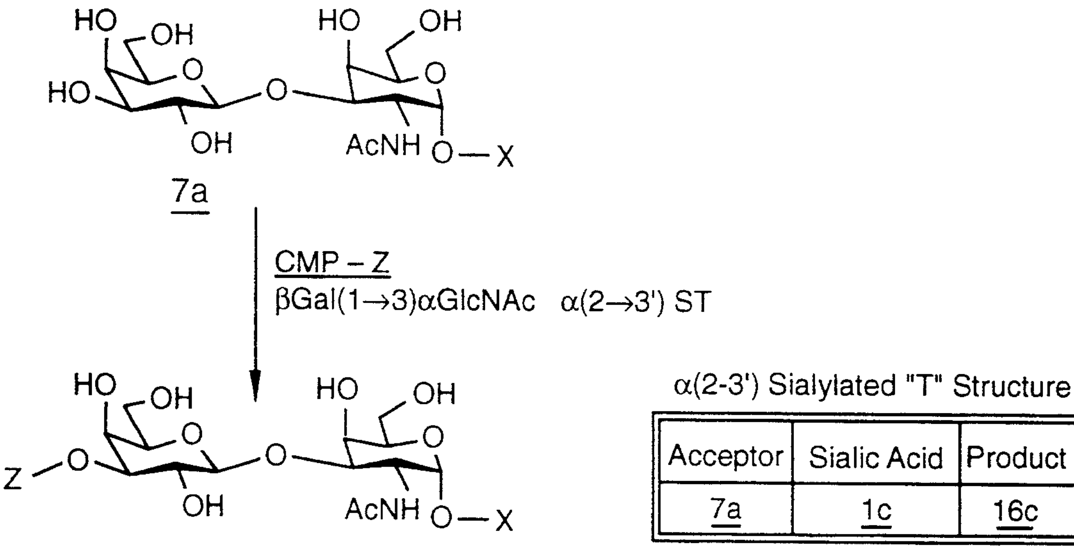
7a
16
α(2-3') Sialylated "T" Structure
| Acceptor | Sialic Acid | Product |
|---|---|---|
| 7a | 1c | 16c |
FIG._8

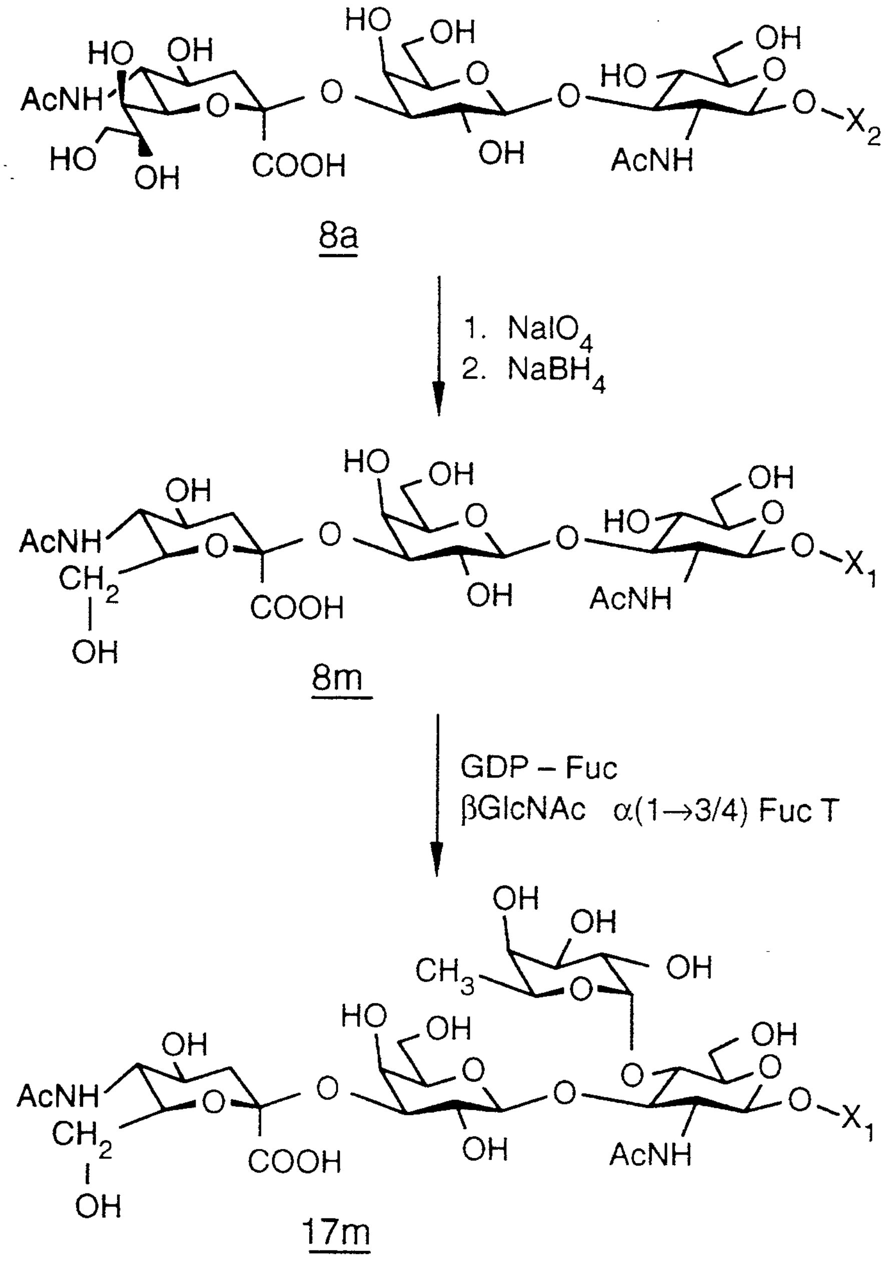
*FIG._9*

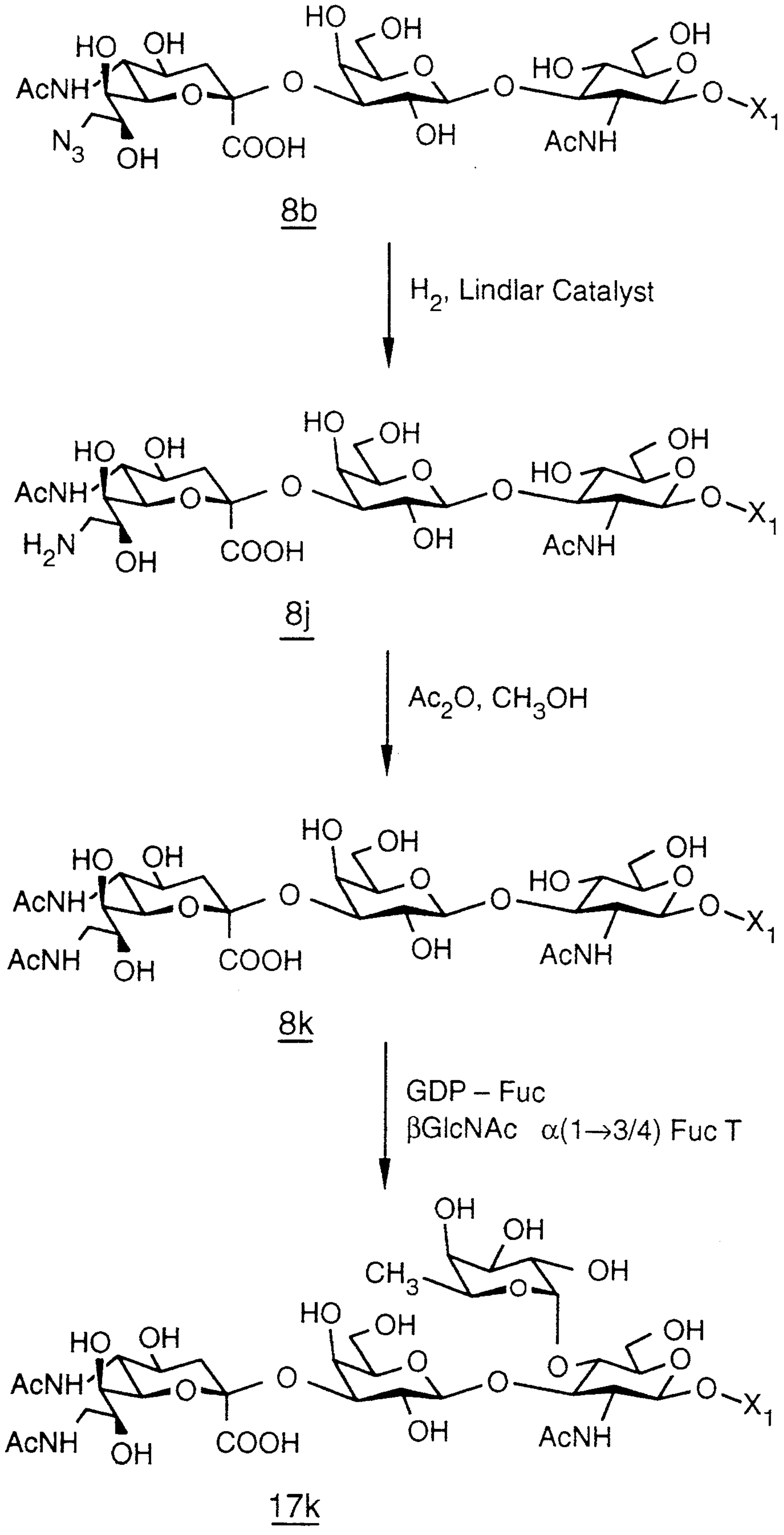
8b
8j
8k
17k
*FIG._10*

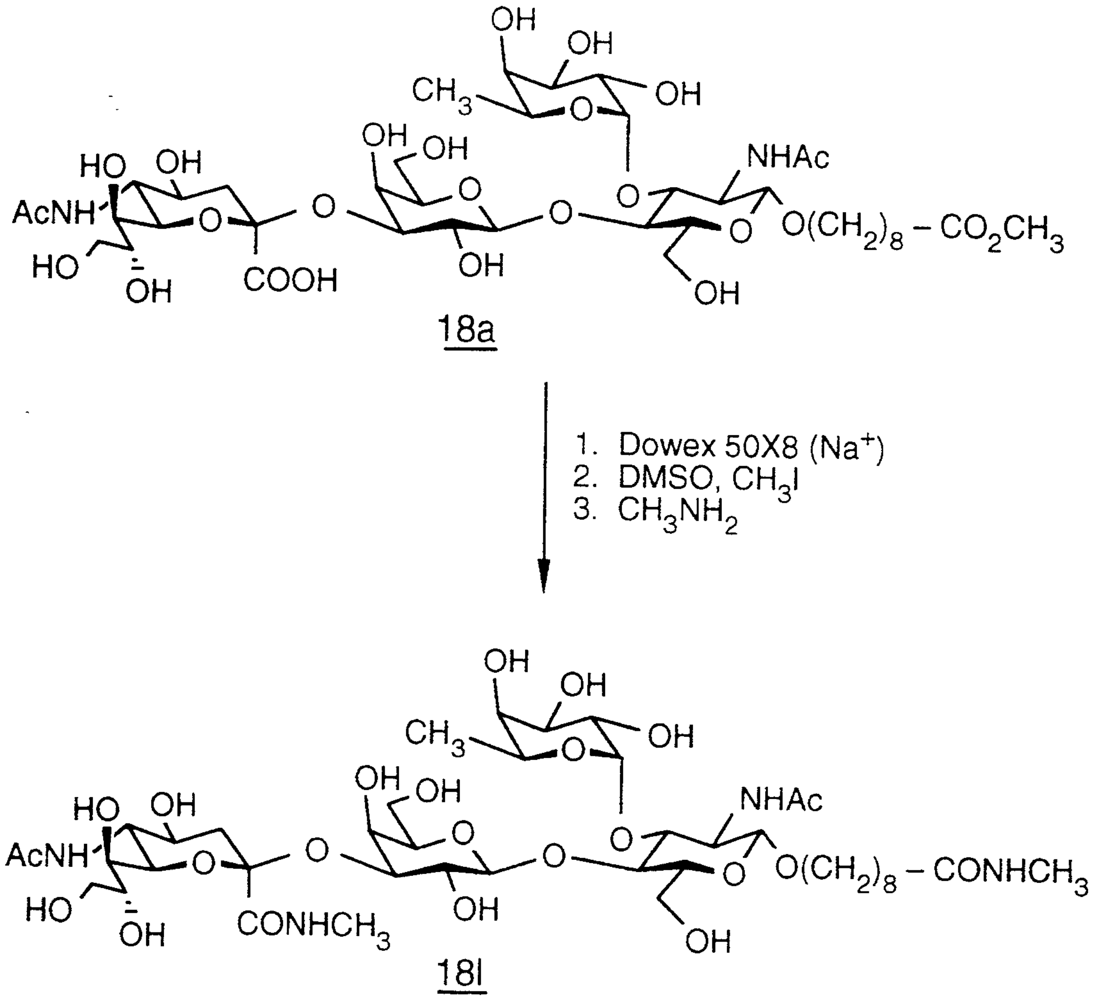
FIG._11

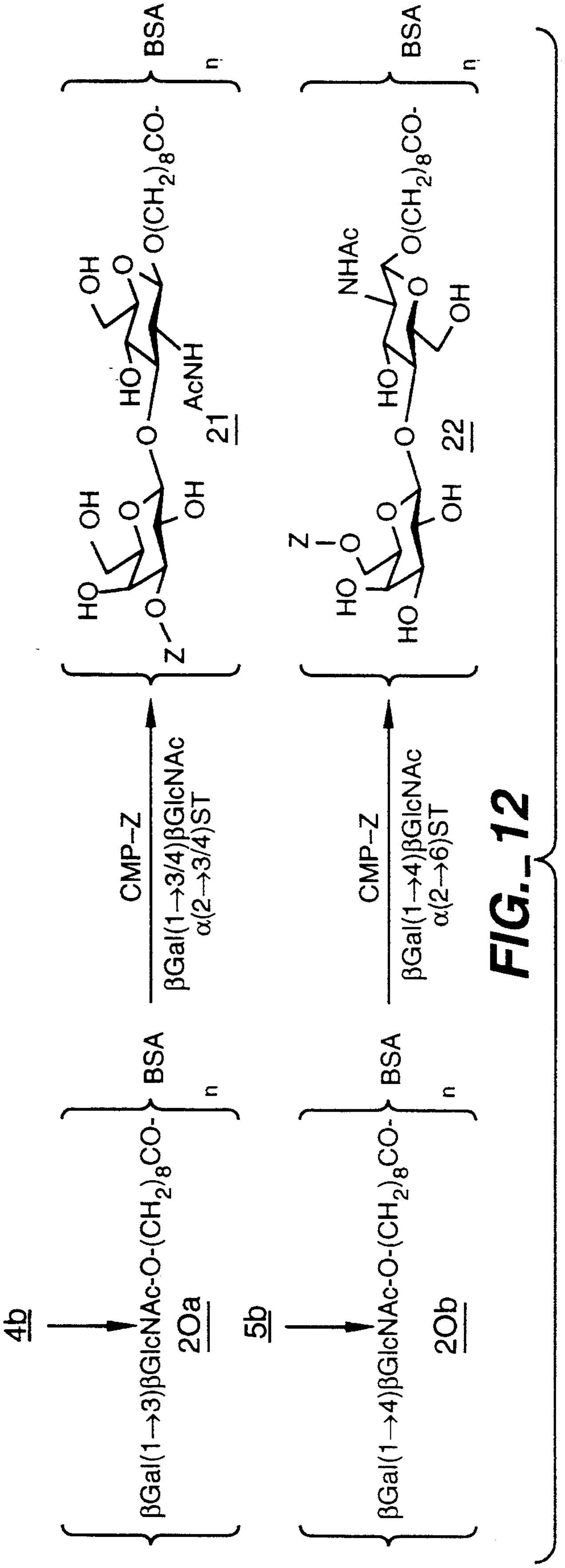
4b 20a 21
5b 20b 22
FIG._12
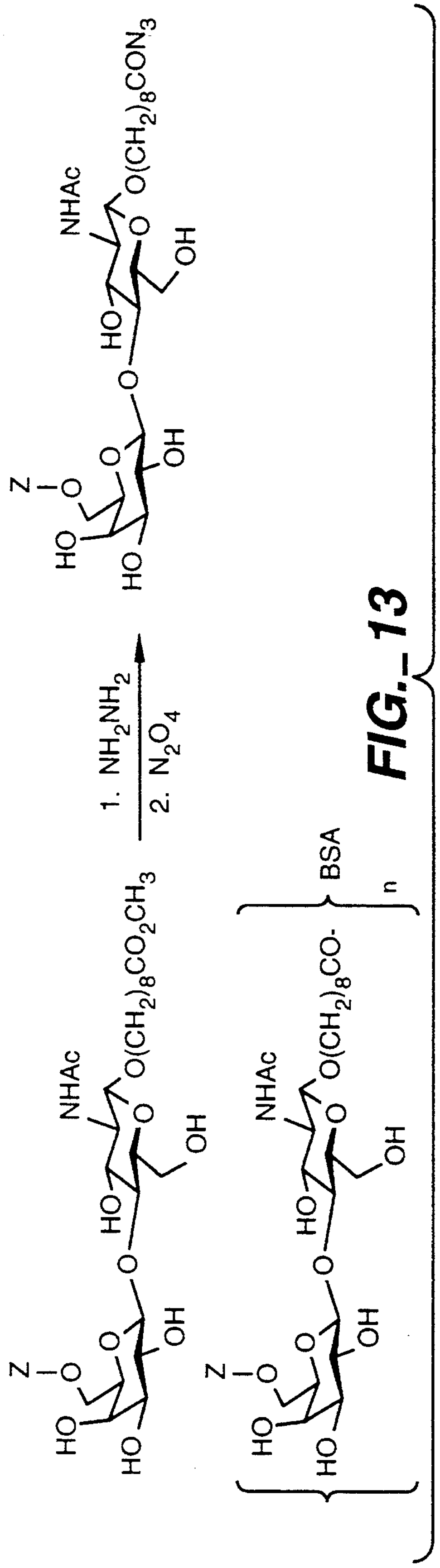
FIG._13

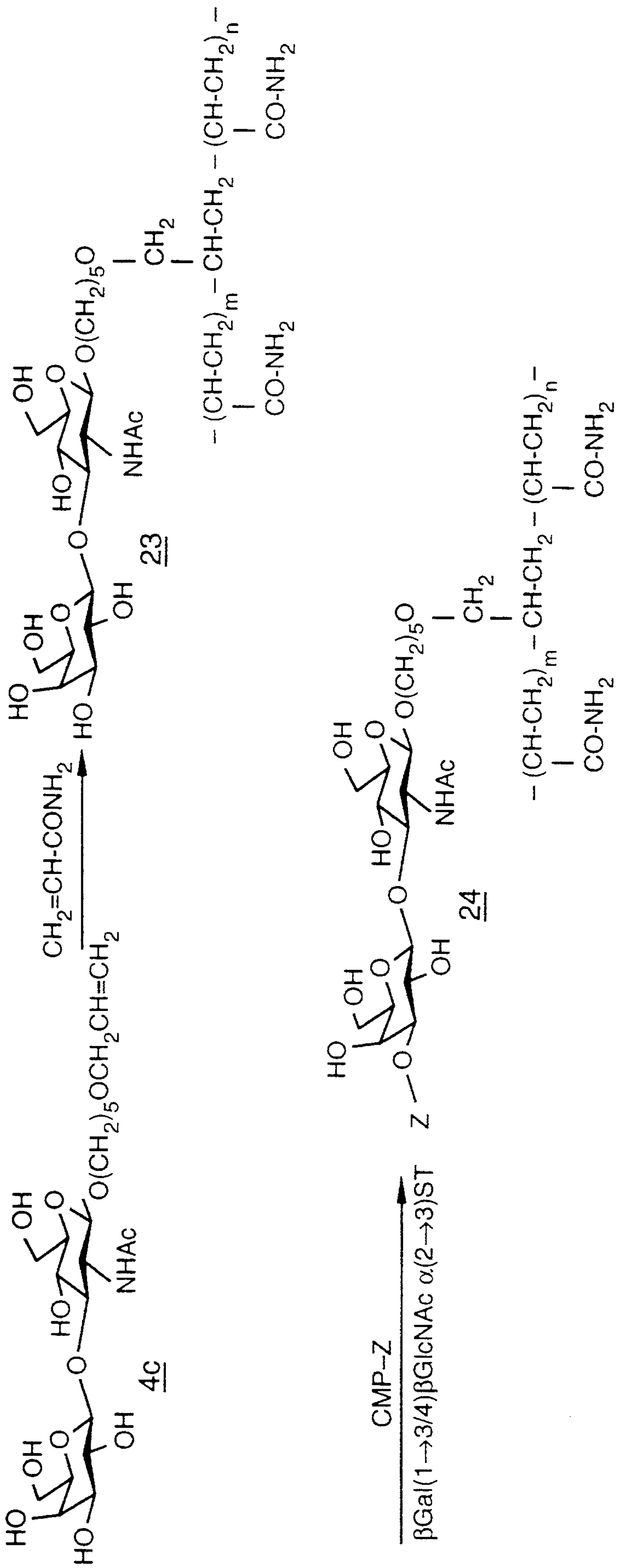
4c
23
24
FIG._14

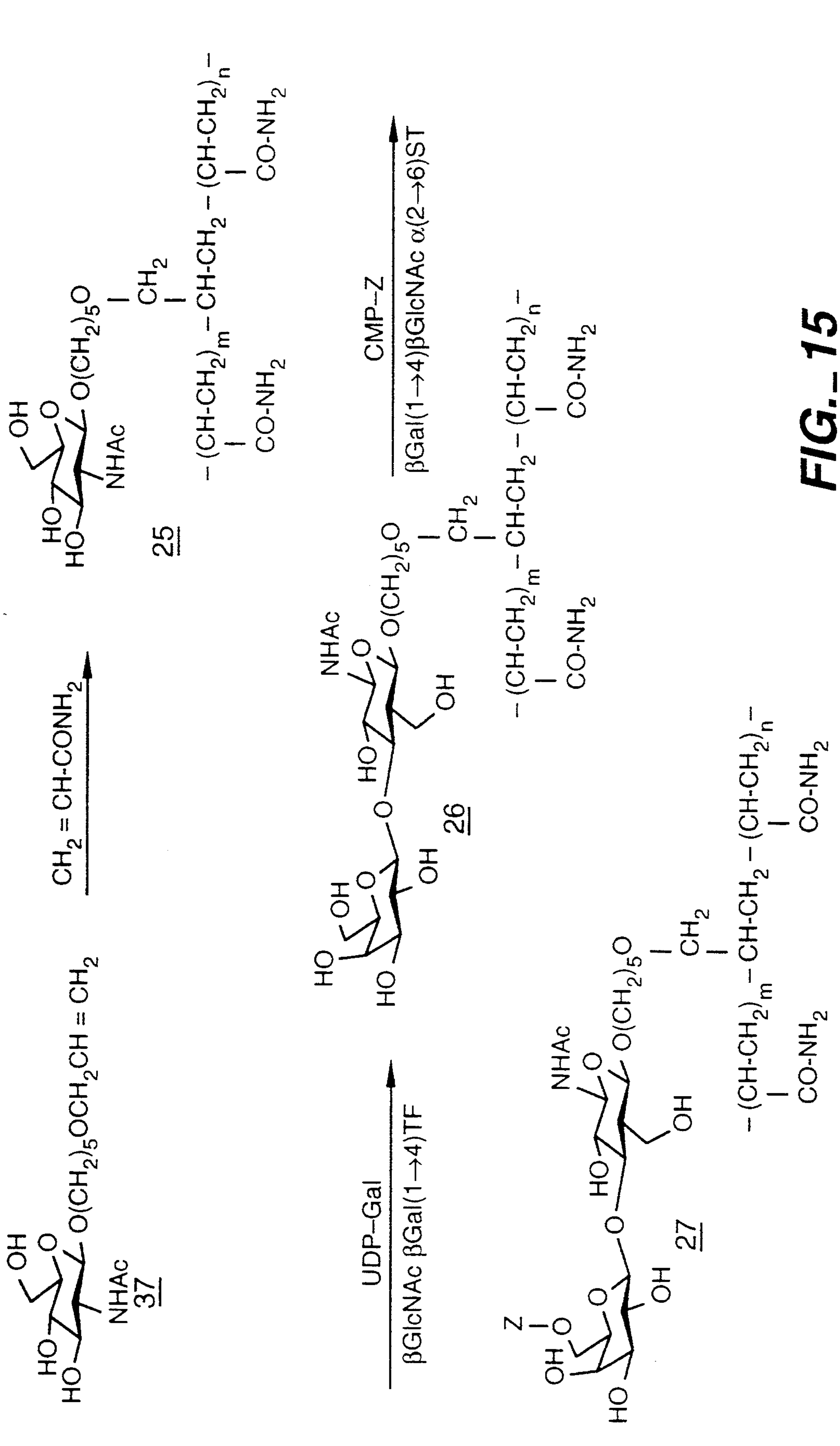
37
25
26
27
FIG._15

METHODS FOR THE ENZYMATIC SYNTHESIS OF ALPHA-SIALYLATED OLIGOSACCHARIDE GLYCOSIDES

CROSS-REFERENCE TO RELATED APPLICATIONS

This application is a continuation-in-part of U.S. Ser. No. 07/714,161 filed Jun. 10, 1991 which application is incorporated herein by reference in its entirety.

BACKGROUND OF THE INVENTION

1. Field of the Invention

This invention is directed to methods for the enzymatic synthesis of alpha-sialylated oligosaccharide glycosides. Specifically, in the methods of this invention, sialyltransferase is employed to transfer an analogue of sialic acid, employed as its CMP-nucleotide, to an oligosaccharide glycoside. The analogue of sialic acid and the oligosaccharide glycoside employed in this method are selected to be compatible with the sialyltransferase employed.

2. References

The following references are cited in this application as superscript numbers at the relevant portion of the application:

1. Horowitz, the Glycoconjugates, Vols. I-V, Pigman, Editor New York Academic Press (1977, 1978, 1982, 1983)
2. Hakomori, Adv. Cancer Res., 52:257-331 (1989)
3. Ippolito et al., U.S. Ser. No. 07/714,161 filed Jun. 10, 1991 as Attorney Docket No. 2275-0018 and entitled "Immunosuppressive and Tolerogenic Oligosaccharide Derivatives"
4. Schengrund et al., J. Biol. Chem., 264: 13233-13237 (1989)
5. Paulson, "Interaction of Animal Viruses with Cell Surface Receptors" in "The Receptors" Conn Ed N.Y. Acad. Press, pp. 131-219 (1985)
6. Feizi, TIBS, 16:84-86 (1991)
7. Brandley et al., Cell, 63:861-863 (1990)
8. Houghton et al., Symposium on Gangliosides and Cancer, pp. 233-237, VCH Publishers (1988)
9. Irie et al., Symposium on Gangliosides and Cancer, pp. 247-257, VCH Publishers (1988)
10. Howard, in "Towards Better Carbohydrate Vaccines"; Proceedings of a meeting organized by the World Health Organization, R. Bell, G. Torrigani, Editors, pp. 212-236, Wiley, Chichester (1987).
11. Henningsson et al., Cancer Immunol. Immunother., 25:231-241 (1987)
12. Fung et al., Cancer Res., 50:4308-4314 (1990)
13. Livingston et al., Proc. Natl. Acad. Sci. (USA), 84:2911-2915 (1987)
14. Naor et al., Prog. Allergy, 22:107-146 (1977)
15. Orskov et al., J. Exp. Med., 149:669-685 (1979)
16. Barsoum et al., Mol. Immunol., 18:495-550 (1981)
17. Jennings et al., U.S. Pat. No. 4,727,136 (1985)
18. Honda et al., J. Blochem., (Tokyo) 95:1323-1329 (1984)
19. Nakamura et al., J. Biochem., (Tokyo) 99:219-226 (1986)
20. Reuter et al., Glycoconjugate J., 5:133-135 (1988)
21. Weinstein et al., J. Biol. Chem., 257:13835-13844 (1982)
22. Paulsen et al., J. Biol. Chem., 252:2356-2362 (1977)

23. Evans-Sadler et al., J. Biol. Chem., 254:4434-4443 (1979)
24. Conradt et al., Japanese-German Symp. pp. 104-105 Berlin (1988)
25. Joziasse et al., J. Biol. Chem., 260:4941-4951 (1985)
26. Evans-Sadler, J. Biol. Chem., 254:5934-5941 (1979)
27. Bergh et al., Eur. J. Biochem., 136:113-118 (1983)
28. Higa et al., J. Biol. Chem., 260:8838-8849 (1985)
29. Paulsen et al., Eur. J. Biochem., 140:523-530 (1984)
30. de Heij et al., Carbohydr. Res., 149:85-99 (1986)
31. Sialic Acids in "Cell Biology Monographs" Schauer, Editor, Vol. 10 (1982)
32. Okamoto et al., Tetrahedron, 46, No. 17, pp. 5835-5837 (1990).
33. Ratcliffe et al., U.S. Pat. No. 5,079,353, (1987).
34. Abbas et al., Proc. Japanese-German Symp. Berlin, pp. 20-21 (1988).
35. Paulsen, Agnew. Chem. Int. Ed. Eng., 21:155-173 (1982).
36. Schmidt, Agnew. Chem. Int. Ed. Eng., 25:212-235 (1986).
37. Fûgedi et al., Glycoconj. J., 4:97-108 (1987).
38. Kameyama et al., Carbohydr. Res., 209:$C_1$-$C_4$ (1991).
39. Brossmer et al., Biochem. Biophys. Acta., 96:1282-1289 (1980)
40. Gross et al., Eur. J. Biochem., 168:595-602 (1987)
41. Zbiral et al., Monatsh. Chem., 119:127-141 (1988)
42. Sharma et al., Carbohydr. Res., 175:25-34 (1989)
43. Hasegawa et al., J. Carbohydr. Chem., 8:579-588 (1989)
44. Zbiral et al., Monatsh. Chem., 116:87-98 (1985)
45. Salunkhe et al., Liebigs Ann. Chem., pp. 187-189 (1988)
46. Hasegawa et al., J. Carbohydr. Chem., 8:135-144 (1989)
47. Gross et al., Biochemistry, 27:4279-4283 (1989)
48. Zbiral et al., Carbohydr. Res., 194:C15-C18 (1989)
49. Gross et al., FEBS Lett., 232:145-147 (1988)
50. Paulsen et al., Liebigs Ann. Chem., pp. 277-279 (1988)
51. Nakajima et al., Agric. Biol. Chem., 52:1209-1215 (1988)
52. Baumberger et al., Helv. Chem. Acta, 69:1535-1541 (1986)
53. Beau et al., Eur. J. Biochem., 160:531-540 (1980)
54. Mack et al., Tetrahedron Lett., 28:191-194 (1987)
55. Gross et al., Eur. J. Biochem., 177:583-589 (1988)
56. Christian et al., Carbohydr. Res., 194:49-61 (1989)
57. Conradt et al., FEBS Lett., 170:295-300 (1984)
58. Christian et al., Carbohydr. Res., 162:1-11 (1987)
59. Haverkamp et al., Hoppe-Seyler's Z. Physiol. Chem., 360:159-166 (1979)
60. Gross et al., Glycoconj. J., 4:145-156 (1987)
61. Hagedorn et al., XIIIth Carbohydr. Symp., Ithaca (1986) A4
62. Toone et al., Tetrahedron, No. 17, 45:5365-5422 (1989)
63. Aplin et al., C. R. C. Crit. Rev. Biochem., pp.259-306 (1981)
64. Dick et al., Glycoconjugates of Bacterial Carbohydrate Antigens in "Contributions to Microbiology and Immunology, Conjugate Vaccines" Crue et al Eds, Basel, Karger, 10:48-114 (1989)
65. Lemieux et al., J. Amer. Chem. Soc., 97:4076-4083 (1975)
66. Pinto et al., Carbohydr. Chem., 124:313-318 (1983)
67. Bernstein et al., Carbohydr. Res., 78:C1-C3 (1980)

68. Lee et al., Carbohydr. Res., 37:193–201 (1974)
69. Mazid et al., U.S. Pat. No. 5,059,535,
70. Kean et al., J. Biol. Chem., 241:5643–5650 (1960)
71. Gross et al., Biochemistry 28:7386–7392 (1989)
72. Lemieux et al., U.S. Patent No. 4,137,401 (1976).
73. Lemieux et al., U.S. Patent No. 4,195,174 (1978).
74. Paulsen et al., Carbohydr. Res., 125:21–45 (1984).
75. Sabesan et al., Can. J. Chem., 62:644–652 (1984).
76. Alais et al., Carbohydr. Res., 207:11–31 (1990).
77. Lemieux et al., U.S. Patent No. 4,767,845 (1987)
78. Unverzagt et al., J. Amer. Chem. Soc., 112:9308–9309 (1990)
79. Palcic et al., Carbohydr. Res., 190:1–11 (1990); and
80. Chernyak et al., Carbohydr. Res., 141:199–212 (1985)
81. Ritter et al., Int. J. Cancer, 48:379–385 (1991).
82. Ritter et al., Immunobiology, 182:32–43 (1991)
83. Beyer et al., Adv. Enzymol., 52:24–158 (1981)

3. State of the Art

Carbohydrates and/or oligosaccharides are present on a variety of natural and pathological glycoconjugates[1]. Of particular interest are carbohydrates and oligosaccharides containing sialic acid residues particularly at the nonreducing sugar terminus[31]. Such sialic acid terminated carbohydrates and oligosaccharides are present in a number of products which have been implicated in a wide range of biological phenomena based, in part, on the concept of recognition signals carried by the carbohydrate structures and by their binding to specific ligands.

Specifically, such sialic acid terminated carbohydrates and oligosaccharides are believed to be receptors for the binding of toxins[4], pathogenic agents such as viruses[5], and are believed to be recognition sites for a variety of lectins, particularly those involved in cellular adhesion[6,7], etc.

Similarly, certain oligosaccharides including sialic acid terminated oligosaccharides have been identified as capable of suppressing a cell-mediated immune response to an antigen. The ability of such oligosaccharides to suppress a cell mediated immune response to an antigen is described by Ippolito et al.[3] which reference is incorporated herein by reference in its entirety.

Additionally, the presence of certain sialyl terminated oligosaccharides in tumor-related antigens is documented in the art[1] and, in general, the structures of the oligosaccharides present on such antigens have been modified in some way from normal oligosaccharides so as to lead to the expression of tumor related antigens[2]. The prospect of passive immunotherapy with monoclonal antibodies directed against some sialylated tumor-associated antigens, such as the gangliosides $GD_2$, $GD_3$ and $GM_2$, in patients with melanoma is being investigated[8,9]. However, most tumor-associated antigens are unable to lead to the production of tumor specific antibodies which would either inhibit or prevent the growth of such tumors. Without being limited to any theory, it is believed that this is due to the absence of real tumor specific antigens and that the structure of such antigens cross-react with that of similar structures expressed in a restricted number of normal tissue. In addition, carbohydrate antigens are generally not believed to lead to a T-cell mediated immune response that is expected to play a role in active immunity[10]. However, some recent studies indicate that, in some cases, tumor-associated carbohydrate antigens may stimulate anticancer T-cell immunity[11,12] or the production of cytotoxic antibodies[13].

In view of the general inability of carbohydrate tumor-related antigens to produce cytotoxic tumor specific antibodies, it has been proposed to chemically modify naturally occurring weak antigens so as to improve their antigenicity[14]. In this regard, methods for chemical modification of specific groups on carbohydrate tumor-related antigens have been reported and, because of the importance of the sialic acid group in sialylated oligosaccharide antigens, much of the focus of chemical modifications to non-or weakly-immunogenic or naturally occurring antigens has been to derivatize the sialic acid residue in the expectation that such modification could result in improved immunogenicity.

Specifically, the art has recognized that some structural modifications present on naturally occurring sialic acids render the corresponding oligosaccharides immunogenic in selected hosts. For example, *E. coli* K1 polysaccharide [an alpha(2-8) linked polymer of N-acetylneuraminic acid] is a poor immunogen but antigenic variations resulting from a partial and random O-acetylation of the sialic acid gave polysaccharides with increased immunogenic properties.[15] Chemical modifications of the sialic acid moiety of rabbit transferrin provides a modified antigen that produced cross-reacting auto-antibodies in rabbits[16]. Likewise, the creation of a more immunogenic epitope by chemical modification of the sialic acid group of B meningococcal polysaccharide has been achieved by the replacement of the N-acetyl with an N-propionyl group. The resulting artificial antigens produced high levels of cross-reacting antibodies as well as imparting a boosting effect[17]. Other literature references disclose immunogenic properties for the ganglioside $GM_1$[18,19] and $GM_3$[82] obtained by chemical modification of the sialic acid group[18,19].

Recent work with artificial antigens indicates that while chemically modified sialosides (melanoma associated glycolipid antigens) are antigenic in humans, the antibodies generated by these modified sialosides do not cross-react with the natural substance.[81] On the other hand, when injected into mice, chemically modified sialylated antigens produce antibodies which do cross-react with the natural substance. Accordingly, cross-reacting monoclonal or polyclonal antibodies generated in mice would serve as a basis for either a diagnostic assay for determining the presence and/or amount of the natural substance in a human host or as a basis for antibody therapy for a disease condition in which the natural substance is attack by the antibodies which can optionally be coupled to a therapeutic agent.

It is also contemplated that the chemical modification of the sialic acid group of sialylated oligosaccharide glycosides could result in oligosaccharide glycosides having improved activity in the suppression of cell-mediated immune responses to an antigen.

However, chemical modification of the sialic acid group of such antigens or of such oligosaccharides is not feasible on a practical level by virtue of the fact that the chemical reactions employed must be specific for the intended modification so that the antigen or oligosaccharide is not altered in some unintended manner. As is apparent, such limitations make impractical the extent and type of chemical modifications which can be conducted on oligosaccharides or antigens.

Alternatively, it is also possible to initially modify the sialic acid which is then coupled to an oligosaccharide glycoside by chemical synthesis so as to provide an alphasialylated oligosaccharide containing an analogue of sialic acid. In this approach, a modified sialic acid residue is chemically generated and then chemically added to a specific site of an oligosaccharide. The modified oligosaccharide could either be used in methods for suppression of cell-mediated immune responses; or, if an appropriate aglycon group is employed, the modified oligosaccharide could be linked to a carrier to generate an artificial conjugate, including artificial antigens.

However, this approach is complicated by the fact that such a chemical synthesis invariably involves multistep procedures which, at best, generally leads to overall moderate yields in the final product. Additionally, the inherent difficulties in chemically making stereoselectively an alpha-sialoside linkage dictate that the complete chemical synthesis of alpha-sialylated oligosaccharides would be a lengthy and a particularly difficult process for modified sialic acids.

In view of the above, it would be particularly advantageous to develop methods for the facile preparation of alpha-sialylated oligosaccharides containing an analogue of sialic acid. The present invention accomplishes this by using sialyltransferases to effect efficient coupling of an analogue of sialic acid activated as its CMP-nucleotide derivative (an artificial donor as defined below) to a saccharide glycoside or an oligosaccharide glycoside (an artificial acceptor as defined below).

While admittedly sialyltransferase enzymes are known to transfer N-acetylneuraminic acid (natural donor), activated as its cytidine monophosphate (CMP) derivative, to the terminal oligosaccharide structures of glycolipids and glycoproteins (natural acceptors), the use of such transferases in the transfer of an analogue of N-acetylneuraminic acid (artificial donor) to the non-reducing sugar terminus of an oligosaccharide glycoside (artificial acceptor) and other artificial acceptors has not heretofore been disclosed. At best, the art discloses that sialyltransferases can accept modification in either the donor or the acceptor and still result in the transfer but the art fails to suggest that sialyltransferases can accept modification in both the donor and the acceptor and still efficiently transfer analogues of sialic acid. The finding that sialyltransferases possess sufficient recognition flexibility to transfer an artificial donor to an artificial acceptor is particularly surprising in view of the unpredictability of catalysis including enzyme catalysis.

SUMMARY OF THE INVENTION

The present invention is directed to methods for the versatile synthesis of oligosaccharide glycosides terminated in the non-reducing sugar end by an analogue of N-acetylneuraminic acid. In particular, the methods of this invention employ sialyltransferases to transfer analogues of sialic acid, activated as their CMP-nucleotide derivatives, to oligosaccharide glycoside acceptors.

Accordingly, in one of its method aspects, the present invention is directed to a method for the enzymatic synthesis of an alpha-sialylated oligosaccharide glycoside containing an analogue of sialic acid which method comprises the steps of:

a) selecting a sialyltransferase;

b) selecting an analogue of sialic acid which compatible with the sialyltransferase selected in step a);

c) converting said analogue to its CMP-nucleotide derivative;

d) contacting said CMP-nucleotide derivative with an oligosaccharide glycoside acceptor of the formula oligosaccharide-Y-R in the presence of the sialyltransferase under conditions whereby the selected acid is transferred from the CMP-nucleotide derivative to the non-reducing sugar terminus of the oligosaccharide glycoside acceptor so as to form an alphasialylated oligosaccharide containing an analogue of sialic acid wherein R represents an aglycon moiety containing at least one carbon atom, Y is selected from the group consisting of O, NH and S, and oligosaccharide is an oligosaccharide of from 2 to about 10 saccharide units in which the terminal units at the non-reducing terminus of the oligosaccharide are compatible with the selected sialyltransferase.

In a preferred embodiment, the analogue of sialic acid is converted to its CMP-nucleotide derivative by use of the enzyme CMP-sialic acid synthase.

In still another preferred embodiment, the aglycon moiety, R, is selected from the group consisting of —(A)—Z′ wherein A represents a bond, an alkylene group of from 2 to 10 carbon atoms, and a moiety of the form $—(CH_2—CR_2G)_n—$ wherein n is an integer equal to 1 to 5; $R_2$ is selected from the group consisting of hydrogen, methyl, or ethyl; and G is selected from the group consisting of hydrogen, oxygen, sulphur, nitrogen, phenyl and phenyl substituted with 1 to 3 substituents selected from the group consisting of amine, hydroxyl, halogen, alkyl of from 1 to 4 carbon atoms and alkoxy of from 1 to 4 carbon atoms; and Z′ is selected from the group consisting of hydrogen, methyl and, when G is not oxygen, sulphur or nitrogen and A is not a bond, then Z′ is also selected from the group consisting of —OH, —SH, $—NH_2$, $—NHR_3$, $—N(R_3)_2$, —C(O)OH, $—C(O)OR_3$, $—C(O)NH—NH_2$, $—C(O)NH_2$, $—C(O)NHR_3$, $—C(O)N(R_3)_2$, and $—OR_4$ wherein each $R_3$ is independently alkyl of from 1 to 4 carbon atoms and $R_4$ is an alkenyl group of from 3 to 10 carbon atoms.

Preferably, the aglycon group is a hydrophobic group of at least 2 carbon atoms and more preferably at least 4 carbon atoms. Most preferably, the aglycon moiety is a hydrophobic group selected from the group consisting of $—(CH_2)_8COOCH_3$, $—(CH_2)_5OCH_2CH{=}CH_2$ and $—(CH_2)_8CH_2OH$.

When the aglycon group is one which is capable of being linked to a carrier such as an antigenic carrier, the methods of this invention are useful in preparing artificial conjugates such as artificial antigens having one or more alpha sialylated oligosaccharide groups containing an analogue of sialic acid which groups are pendant to the antigen. Artificial antigens serve as antigenic determinants (at least in mice) for the preparation of antibodies, including monoclonal antibodies, which will cross-react with the unmodified antigen (i.e., the natural substance).

One embodiment of such a method is a method for the preparation of artificial conjugates having one or more alpha-sialylated oligosaccharides groups containing an analogue of sialic acid which groups are pendant to a carrier and which method comprises the steps of:

a) selecting a sialyltransferase;

b) selecting an analogue of sialic acid which is compatible with the sialyltransferase selected in step a);

c) converting said analogue to its CMP-nucleotide derivative;

d) contacting said CMP-nucleotide derivative with an oligosaccharide glycoside acceptor of the formula oligosaccharide-Y-$R_1$ in the presence of the sialyltransferase under conditions whereby the selected acid is transferred from the CMP-nucleotide derivative to the non-reducing sugar terminus of the oligosaccharide glycoside acceptor so as to form an alphasialylated oligosaccharide glycoside containing an analogue of sialic acid wherein $R_1$ represents an aglycon moiety capable of being linked to a carrier, Y is selected from the group consisting of O, NH and S, and oligosaccharide is an oligosaccharide of from 2 to about 10 saccharide units in which the terminal units at the non-reducing terminus of the oligosaccharide are compatible with the selected sialyltransferase;

e) selecting a carrier having one or more functionalities capable of linking to the aglycon moiety of the alpha-sialylated oligosaccharide glycoside produced in step (d) above; and f) linking one or more of said alpha-sialylated oligosaccharide glycosides containing an analogue of sialic acid, produced in step d), to the carrier so as to form the artificial conjugate.

Another embodiment of such a method is a method for the preparation of artificial conjugates having one or more alpha-sialylated oligosaccharides groups containing an analogue of sialic acid pendant to a carrier which method comprises the steps of:

a) selecting a sialyltransferase;

b) selecting an oligosaccharide glycoside acceptor of the formula oligosaccharide-Y-$R_1$ wherein $R_1$ represents an aglycon moiety capable of being linked to a carrier, Y is selected from the group consisting of O, NH and S, and oligosaccharide is an oligo-saccharide of from 2 to about 10 saccharide units in which the terminal units at the non-reducing terminus of the oligosaccharide are compatible with the selected sialyltransferase;

c) selecting a carrier having one or more functionalities capable of linking to the aglycon moiety of the selected oligosaccharide glycoside;

d) linking one or more of said oligosaccharide glycoside acceptors to said carrier so as to form an artificial conjugate having one or more oligosaccharide glycoside groups pendant thereto;

e) selecting an analogue of sialic acid which is compatible with the sialyltransferase selected in step a);

f) converting said analogue to its CMP-nucleotide derivative;

g) contacting said CMP-nucleotide derivative with the artificial conjugate produced in step d) above in the presence of a sialyltransferase under conditions whereby the selected acid is transferred from the CMP-nucleotide derivative to the non-reducing sugar terminus of the oligosaccharide group(s) pendant to the artificial conjugate so as to form an artificial conjugate having one or more alpha sialylated oligosaccharide groups containing an analogue of sialic acid pendant to said conjugate.

In these embodiment, $R_1$ is preferably selected from the group consisting of —(A)—Z″ wherein A is selected from the group consisting of an alkylene group of from 2 to 10 carbon atoms and a moiety of the form $-(CN_2-CR_5G)_n-$ wherein n is an integer equal to 1 to 5; $R_5$ is selected from the group consisting of hydrogen, methyl, or ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z″ is selected from the group consisting of hydrogen and, when G is not oxygen, sulphur or nitrogen, then Z″ is also selected from the group consisting of —OH, —SH, $-NH_2$, $-NHR_6$, —C (O) OH, $-C(O)OR_6$, $-C(O)NHNH_2$, and $-OR_7$ wherein each $R_6$ is independently alkyl of from 1 to 4 carbon atoms and $R_7$ is an alkenyl group of from 3 to 10 carbon atoms with the proviso that when A is a bond, Z is not hydrogen. In such cases, the —(A)—Z″ group defines a group capable of being linked to a carrier or is capable of being derivatized to a group which is capable of being linked to a carrier.

Most preferably, the aglycon moiety is a hydrophobic group selected from the group consisting of $-(CN_2)_8COOCH_3$ $-(CN_2)_5OCN_2CH{=}CH_2$ and $-(CH_2)_8CH_2OH$. In particular, the use of a hydrophobic group and most especially, a $-(CH_2)_8COOCH_3$ or $-(CH_2)_5OCH_2CH{=}CH_2$ or $-(CH_2)_8CH_2OH$ group may provide for some enhancement in the kinetics of sialic acid transfer via a sialyltransferase.

In a preferred embodiment, the analogue of sialic acid is converted to its CMP-nucleotide derivative by use of the enzyme CMP-sialic acid synthase.

BRIEF DESCRIPTION OF THE DRAWINGS

FIG. 1 illustrates a general synthetic scheme used for the synthesis of some analogues of Neu5Ac.

FIG. 2 illustrates the structures of oligosaccharide glycosides acceptors 3*b* to 7*a*.

FIG. 3 illustrates a general reaction scheme for the synthesis of oligosaccharide glycoside 4*c* as specified in Example 8 and for the synthesis of monosaccharide glycoside 37 as specified in Example 9.

FIG. 4 illustrates the enzymatic transfer of Neu5Ac, and of analogues thereof by the $\beta$Gal(1→$\frac{3}{4}$)$\beta$GlcNAc $\alpha$(2→3′)sialyltransferase to a $\beta$Gal(1→3)$\beta$GlcNAc-terminal structure. FIG. 4 also illustrates the enzymatic transfer of L-fucose onto the sialylated oligosaccharide glycosides.

FIG. 5 illustrates the enzymatic transfer of Neu5Ac, and analogues thereof by the $\beta$Gal(1→$\frac{3}{4}$)$\beta$GlcNAc $\alpha$(2→3′)sialyltransferase to a $\beta$Gal(1→4)$\beta$GlcNAc-terminal structure. FIG. 5 also illustrates the enzymatic transfer of L-fucose onto the sialylated oligosaccharide glycosides.

FIG. 6 illustrates the enzymatic transfer of Neu5Ac, and analogues thereof by the $\beta$Gal(1→4)$\beta$GlcNAc $\alpha$(2→6′)sialyltransferase to a $\beta$Gal(1→4)$\beta$GlcNAc-terminal structure.

FIG. 7 illustrates the enzymatic transfer of Neu5Ac, and analogues thereof by the $\beta$Gal(1→$\frac{3}{4}$)$\beta$GlcNAc $\alpha$(2→3′)sialyltransferase to a $\beta$Gal(1→4)$\beta$Glc- (lactose) terminal structure.

FIG. 8 illustrates the enzymatic transfer of Neu5Ac, and analogues thereof by the $\beta$Gal(1→3)$\alpha$GalNAc $\alpha$(2→3′)sialyltransferase to a $\beta$Gal(1→3)$\alpha$GalNAc-("T") terminal structure.

FIGS. 9 and 10 illustrate the reaction schemes involved in the synthesis of analogues of Sialyl Lewis$^a$ by chemical modification of a sialylated hapten.

FIG. 11 illustrates the reaction schemes involved in the synthesis of analogues of Sialyl Lewis$^x$ by chemical modification of a sialylated hapten.

FIG. 12 illustrates the reaction schemes involved in the synthesis of artificial antigens having one or more alpha sialylated oligosaccharide groups pendant thereto.

FIG. 13 illustrates the reaction schemes involved in the synthesis of artificial antigens containing one or more alpha sialylated oligosaccharide groups by linking of one or more alpha sialylated oligosaccharide glycosides to an antigenic carrier.

FIG. 14 illustrates the reaction schemes involved in the synthesis of copolymers containing one or more alpha sialylated oligosaccharide groups pendant thereto by using a $\beta$Gal(1→$\frac{3}{4}$)$\beta$GlcNAc $\alpha$(2→3')sialyltransferase.

FIG. 15 illustrates the reaction schemes involved in the synthesis of copolymers containing one or more alpha sialylated oligosaccharide groups pendant thereto by using a $\beta$Gal(1→4)$\beta$GlcNAc $\alpha$(2→6')sialyltransferase.

DETAILED DESCRIPTION OF THE PREFERRED EMBODIMENTS

The present invention is directed to the discovery that sialyltransferases will transfer compatible analogues of sialic acid to certain oligosaccharide glycosides derivatives which are not the natural acceptors for such sialyltransferases. This discovery permits the versatile synthesis of a panel of alpha-sialylated oligosaccharide glycosides containing different sialic acid analogues. This discovery also permits the versatile synthesis of artificial carriers having one or more alpha-sialylated oligosaccharide groups pendant to the carrier.

However, prior to discussing this invention in further detail, the following terms will first be defined.

A. Definitions

As used herein, the following terms have the definitions given below:

The term "sialic acid" means all of the naturally occurring structures of sialic acid including 5-acetoamido-3,5-dideoxy-D-glycero-D-galacto-nonulopyranosylonic acid ("Neu5Ac") and the naturally occurring analogues of Neu5Ac, including N-glycolyl neuraminic acid (Neu5Gc) and 9-O-acetyl neuraminic acid ($Neu5,9Ac_2$), which are compatible with the selected sialyltransferase. A complete list of naturally occurring sialic acids known to date are provided by Schauer[31].

Naturally occurring sialic acids which are recognized by a particular sialyltransferase so as to bind to the enzyme and are then available for transfer to an appropriate acceptor oligosaccharide structure are said to be compatible with the sialyltransferase and are sometimes referred to herein as a "compatible naturally occurring sialic acid".

The term "analogues of sialic acid" refers to analogues of naturally occurring structures of sialic acid including those wherein the sialic acid unit has been chemically modified so as to introduce, modify and/or remove one or more functionalities from such structures. For example, such modification can result in the removal of an —OH functionality, the introduction of an amine functionality, the introduction of a halo functionality, and the like.

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 8-deoxy-Neu5Ac, 8-epi-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-dideoxy-Neu5Ac, 4-oxo-Neu5Ac, 3-hydroxy-Neu5Ac, 3-fluoro-Neu5Ac acid as well as the 6-thio analogues of Neu5Ac. The nomenclature employed herein in describing analogues of sialic acid is as set forth by Reuter et al.[20]

Insofar as sialyltransferases are designed to transfer or donate compatible naturally occurring sialic acids, analogues of Neu5Ac are sometimes referred to herein as "artificial donors" whereas the compatible naturally occurring sialic acids are sometimes referred to herein as the "natural donors".

The term "sialyltransferase" refers to those enzymes which transfer a compatible naturally occurring sialic acid, activated as its cytidine monophosphate (CMP) derivative, to the terminal oligosaccharide structures of glycolipids or glycoproteins (collectively glycoconjugates) and include enzymes produced from microorganisms genetically modified so as to incorporate and express all or part of the sialyltransferase gene obtained from another source, including mammalian sources. Numerous sialyltransferases have been identified in the literature with the different sialyltransferases generally being distinguished from each other by the terminal saccharide units on the glycoconjugates which accept the transferase[83]. For example, sialyltransferases, which build the following terminal oligosaccharide structures on glycoconjugates have been characterized:

$\alpha$Neu5Ac(2-3)$\beta$Gal(1$\frac{3}{4}$)$\beta$GlcNAc[21]
$\alpha$Neu5Ac(2-6)$\beta$Gal(1-4)$\beta$GlcNAc-[21,22]
$\alpha$Neu5Ac(2-3)$\beta$Gal(1-3)$\alpha$GalNAc-[23-25]
$\alpha$Neu5Ac(2-6)$\alpha$GalNAc-[26-28]
$\alpha$Neu5Ac(2-6)$\beta$GlcNAc-[29,30].

Other sialyltransferases with a variety of specificities have been isolated from a variety of sources.

Analogues of sialic acid activated as their cytidinemonophosphate derivative which are recognized by a particular sialyltransferase so as to bind to the enzyme and are then available for transfer to an appropriate acceptor oligosaccharide structure are said to be compatible with the sialyltransferase and are sometimes referred to herein as a "compatible analogue of sialic acid". Because the transfer reaction employs a sialyltransferase, it goes without saying that an analogue of sialic acid employed in such a reaction must be a compatible analogue of sialic acid.

CMP-nucleotide derivative of Neu5Ac refers to the compound:

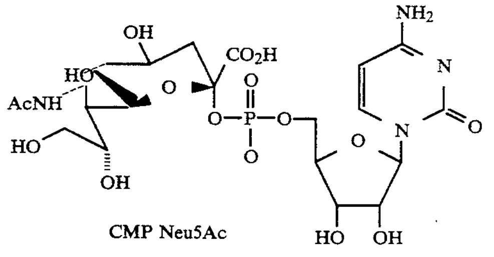

CMP Neu5Ac

CMP-derivatives of analogues of sialic acid refer to those compounds having structures similar to that above with the exception that the Neu5Ac residue is replace with an analogue of sialic acid.

The term "oligosaccharide glycoside" refers to compounds of the formula

OLIGOSACCHARIDE-Y-R wherein oligosaccharide represents a carbohydrate structure of from 2 to about 10 saccharide units in which the terminal units at the non-reducing terminus of the oligosaccharide are compatible with the selected sialyltransferase; Y is selected from the group consisting of O, S, —NH— and a bond; and R represents an aglycon moiety containing at least one carbon atom.

The oligosaccharide glycosides described above are different from oligosaccharides and glycoconjugates because the aglycon moiety is not hydrogen, a protein, or a lipid capable of forming a micelle or other large aggregate structure.

Since such naturally occurring oligosaccharides and glycoconjugates are known acceptors for sialyltransferase, and are believed to be acceptors of sialyltransferase in vivo , these oligosaccharides and glycoconjugates are sometimes referred to herein as "natural acceptors". Contrarily, since the oligosaccharide glycosides employed in this invention are different from such "natural acceptors", they are sometimes referred to herein as "artificial acceptors". That is to say that artificial acceptors are those oligosaccharide glycosides which contain a substituent at the anomeric carbon atom of the reducing sugar which substituent is other than hydroxyl, a protein, or a lipid capable of forming a micelle or other large molecular weight aggregate. Accordingly, a protein linked to the anomeric carbon atom of the reducing sugar of the oligosaccharide glycoside through its aglycon moiety would be an artificial acceptor since this acceptor contains an "artificial" unit, i.e., the aglycon linking group.

Optionally, the oligosaccharide glycosides of this invention can be further distinguished from such natural acceptors by virtue of chemical modification(s) to one or more of the saccharide units of the oligosaccharide glycoside. For example, such chemical modification could involve the introduction and/or removal of one or more functionalities in one or more of the saccharide unit(s). For example, such modification can result in the removal of an —OH functionality, the removal of saccharide unit(s), the introduction of an amine functionality, the introduction of a halo functionality, the introduction of one or more saccharide unit(s), and the like.

In a preferred embodiment, the aglycone moiety, R, is selected from the group consisting of —(A)—Z' wherein A represents a bond, an alkylene group of from 2 to 10 carbon atoms, and a moiety of the form $—(CH_2—CR_2G)_n—$ wherein n is an integer equal to 1 to 5; $R_2$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z' is selected from the group consisting of hydrogen, methyl and, when G is not oxygen, sulphur or nitrogen and A is not a bond, then Z' is also selected from the group consisting of —OH, —SH, $—NH_2$, $—NHR_3$, $—N(R_3)_2$, —C(O)OH, $—C(O)OR_3$, $—C(O)NH—NH_2$, $—C(O)NH_2$, $—C(O)NHR_3$, $—C(O)N(R_3)_2$, and $—OR_4$ wherein each $R_3$ is independently alkyl of from 1 to 4 carbon atoms and $R_4$ is an alkenyl group of from 3 to 10 carbon atoms.

When the alpha-sialylated oligosaccharide glycoside is used for preparing an artificial conjugate, then the aglycon, R, on OLIGOSACCHARIDE-Y-R, is then $R_1$, which is a group capable of being linked to a carrier. Preferably, $R_1$ is selected from the group consisting of —(A)—Z" wherein A is selected from the group consisting of an alkylene group of from 2 to 10 carbon atoms, and a moiety of the form $—(CH_2—CR_5G)_n—$ wherein n is an integer equal to 1 to 5; $R_5$ is selected from the group consisting of hydrogen, methyl, or ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z" is selected from the group consisting of hydrogen and, when G is not oxygen, sulphur or nitrogen, then Z" is also selected from the group consisting of —OH, —SH, $—NH_2$, $—NHR_6$, —C(O)OH, $—C(O)OR_6$, $—C(O)NHNH_2$, and $—OR_7$ wherein each $R_6$ is independently alkyl of from 1 to 4 carbon atoms and $R_7$ is an alkenyl group of from 3 to 10 carbon atoms with the proviso that when A is a bond, Z is not hydrogen. In such cases, the —(A)—Z" group defines a group capable of being linked to a carrier or is capable of being derivatized to a group which is capable of being linked to a carrier. The choice of an appropriate carrier may be useful in enhancing immunogenic properties.

The carrier is a low or high molecular weight, nonimmunogenic or antigenic carrier including the linking to a fluorescent label, a radioactive label, biotin, or a photolabile linking arm or a moiety to be targeted. Preferably, the carrier is an antigenic carrier and accordingly, the artificial conjugate is an artificial antigen. In some cases it may be advantageous to employ a nonimmunogenic carrier.

On the other hand, the carrier can be a low molecular weight carrier such as ethylene diamine, hexamethylene diamine, tris(2-aminoethyl)amine, L lysilysine, poly-L-lysine, and polymers of various molecular weights.

Saccharide units (i.e., sugars) useful in the oligosaccharide glycosides described above include by way of example, all natural and synthetic derivatives of glucose, galactose, N-acetyl-glucosamine, N-acetyl-galactosamine, fucose, sialic acid, 3-deoxy-D,L-octulosonic acid and the like. In addition to being in their pyranose form, all saccharide units in the oligosaccharide glycosides are in their D form except for fucose which is in its L form.

As noted above, oligosaccharide glycosides useful in the processes disclosed herein contain terminal units which are compatible with the selected sialyltransferase. That is to say that such compatible terminal units permit recognition of the oligosaccharide glycoside by a particular sialyltransferase so that the sialyltransferase binds to the oligosaccharide glycoside and further permits transfer of the compatible analogue of sialic acid onto the oligosaccharide glycoside.

In a preferred embodiment, the oligosaccharide glycosides (OLIGOSACCHARIDE GLYCOSIDES-Y-R) used to prepare the alpha-sialylated oligosaccharide glycosides by the methods described herein are related to blood group determinants and contain from 3 to 9 saccharide units and possess an analogue of sialic acid on the non-reducing sugar portion of the oligosaccharide.

The term "blood group substances" refer to specific glycoconjugate antigens on red blood cells which serve as the basis for assigning blood into various classes according to immunological compatibility.

The term "blood group determinant" refers to any naturally occurring oligosaccharide segment of the nonreducing-terminal, 3-9 glycosyl residues that constitute the glycan chains of blood group substances.

The term "oligosaccharide glycosides relating to a blood group determinant" refer to an alpha sialylated oligosaccharide glycoside (a) having an oligosaccharide group of from 3 to 9 saccharide units, (b) which is terminated with an aglycon group on the reducing sugar, and (c) wherein the oligosaccharide group is a blood group determinant (as defined above) or an analogue thereof.

Analogues of blood group determinants include those wherein one or more of the monosaccharide units of the blood group determinant has or have been chemically modified so as to introduce, exchange and/or remove one or more functionalities in one or more of the saccharide unit(s). For example, such modification can result in the removal of an —OH functionality, the removal or replacement of saccharide unit(s), the introduction of an amine functionality, the introduction of a halo functionality, the introduction of one or more saccharide unit(s), and the like.

The term "antigenic carrier" refers to a carrier containing one or more functional groups which permit linking to the carrier of an oligosaccharide glycoside containing an analogue of sialic acid at the non-reducing sugar terminus and which produces an antigenic response when injected into animals to which the particular carrier is not endogenous. Such carriers can be proteins [e.g., bovine serum albumin (BSA), human serum albumin (HSA), diphtheria or tetanus toxoid, S-layers, and the like] and are sometimes referred to herein by the abbreviation "Ag".

The particular antigenic carrier selected for use in preparing an artificial antigen is not critical provided it contains or can be derivatized to contain one or more functional groups which permit linking to the carrier of such an oligosaccharide glycoside. Suitable functional groups include, by way of example, carboxylic acid groups, amines groups (including primary and secondary amines), hydroxyl groups, thio groups, and the like. Such functional groups are commonly found on antigenic carriers (e.g., proteins contain numerous such functionality) and/or can be introduced onto such carriers via art recognized methods.

Coupling of one or more of the oligosaccharide glycosides containing an analogue of sialic acid to the antigenic carrier results in a product which is described herein as an "artificial antigen" because when injected into an animal, this antigen will possess one or more nonnaturally occurring oligosaccharide glycoside determinants. The artificial antigens so produced are preferably represented by the formula:

$$[\alpha\text{-sialic acid}'\text{-oligosaccharide-Y-}R_1]_p\text{-Ag}$$

wherein oligosaccharide, Y, $R_1$ and Ag are as defined above, α-sialic acid' refers to an analogue of sialic acid, and p is an integer equal to at least 1. In this embodiment, the artificial antigen, Ag, is linked to the oligosaccharide glycoside through a functional group on the antigen which couples to a complementary functional group on the aglycon group, i.e., the $R_1$ group, of the oligosaccharide.

The term "antibody" refers to an immunoglobulin, or derivative thereof, having an area on the surface or in a cavity which specifically binds to and is thereby defined as complementary with a particular spatial and polar organization of another molecule. The antibody can be monoclonal or polyclonal and can be prepared by techniques that are well known in the art, such as, for example, immunization of a host and collection of sera or hybrid cell line technology.

In this regard, the artificial antigens described above are useful in generating antibodies which recognize and are complementary to the antigenic determinants on the antigen as well as which cross-reacts with the natural substance.

The term "natural substance" refers to a naturally occurring material associated with a defined disease condition (e.g., a tumor-associated carbohydrate antigen) which material contains one or more α-sialylated oligosaccharide groups and which material is either non-immunogenic or weakly immunogenic in the diseased mammal.

B. Synthesis and Methodology

B1. Preparation of Oligosaccharide Glycosides

Oligosaccharide glycosides to which the sialic acid analogue is to be enzymatically coupled are readily prepared either by complete chemical synthesis or by chemical/enzymatic synthesis wherein glycosyltransferases (other than sialyltransferases) are employed to effect the sequential addition of one or more sugar units onto a saccharide or an oligosaccharide. Such methods are well known in the art and do not form a part of this invention. For example, chemical synthesis is a convenient method for preparing either the complete oligosaccharide glycoside; for chemically modifying a saccharide unit which can then be chemically or enzymatically coupled to an oligosaccharide glycoside; or for chemically preparing an oligosaccharide glycoside to which can be enzymatically coupled one or more saccharide units.

Chemical modifications of saccharide units are well known in the art which methods are generally adapted and optimized for each individual structure to be synthesized. In general, the chemical synthesis of all or part of the oligosaccharide glycosides first involves formation of a glycosidic linkage on the anomeric carbon atom of the reducing sugar. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, thioglycoside, etc. The donor is then reacted under catalytic conditions (e.g., a soluble silver salt such as silver trifluoromethanesulfonate, a Lewis acid such as boron trifluoride etherate or trimethylsilyltrifluoromethanesulfonate, or thioglycoside promoters such as methyl trifluoromethanesulfonate or dimethyl(methylthio)sulfonium trifluoromethanesulfonate) with an aglycon or an appropriate form of a carbohydrate acceptor which possess one free hydroxyl group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[32] Ratcliffe et al.[33], Abbas et al.[34], Paulsen[35], Schmidt[36], Fûgedi et al.[37], and Kameyama et al.[38]. The disclosures of each of these references are incorporated herein by reference in their entirety.

On the other hand, enzymatic coupling is accomplished by the use of glycosyl transferases which transfer sugar units, activated as their appropriate nucleotide donors, to specific saccharide or oligosaccharide acceptors, generally at the non-reducing sugar portion of the saccharide or oligosaccharide. See, for example, Toone et al.[62]. Moreover, it is possible to effect selected chemical modifications of the saccharide or oligosaccharide acceptor, of the sugar donor or the product of the enzymatic reaction so as to introduce modifications or further modifications into the structure.

B2. Preparation of Analogues of Sialic Acid

Certain analogues of sialic acid are well known in the art and are prepared by chemical modification of sialic acid using procedures well documented in the art. For example, chemically modified Neu5Ac derivatives including 9-azido-Neu5Ac[39], various 9-amino-Neu5Ac derivatives[40], 9-deoxy-Neu5Ac[41], 9-fluoro-Neu5Ac[42], 9-bromo-Neu5Ac[43], 8-deoxy-Neu5Ac[41], 8-epi-Neu5Ac[44], 7-deoxy-Neu5Ac[47]-epi-Neu5Ac[45], 7,8-bis-epi-Neu5Ac[45], 4-O-methyl-Neu5Ac[53], 4-N-acetyl-Neu5Ac[48], 4-epi-Neu5Ac[47], 4,7-di-deoxy-Neu5Ac[41], 4-oxo-Neu5Ac[49],4-deoxy-Neu5Ac[52], 3-hydroxy-Neu5Ac[50], 3-fluoro-Neu5Ac[51] acid, the product of cleavage of the side chain at C-8 or at C-7[46] as well as the 6-thio analogues of Neu5Ac[54] are reported in the literature. Chemical modification leading to other sialic acid analogues would follow such established procedures.

B3. Activation of Analogues of Sialic Acid to Their CMP—Nucleotide Derivatives

The enzymatic transfer of analogues of sialic acid require the prior synthesis (i.e., activation) of their nucleotide (CMP) derivatives. Activation of the analogues of sialic acid is usually done by using the enzyme CMP-sialic acid synthase which is readily available and the literature provides examples of the activation of various analogues of sialic acid such as 9-substituted Neu-5Ac[28,39,40,55-57], 7-epiNeu5Ac[58], 7,8-bis-epi-Neu5Ac[58], 4-O-methyl-Neu5Ac[59], 4-deoxy-Neu5Ac[60], 4-acetamido-Neu5Ac[48], 7-deoxy-Neu5Ac[56], 4 7-dideoxy-Neu5Ac[56], the 6-thio derivatives of Neu5Ac[61] and Neu-5OH (KDN).

B4. Transfer of the Analogues of Sialic Acid to the Oligosaccharide Glycoside Acceptor The nucleotide derivative of a compatible analogue of sialic acid and the compatible acceptor (i.e., a saccharide glycoside or an oligosaccharide glycoside having terminal saccharide unit(s) on the non-reducing end which are recognized by the selected sialyltransferase) are combined with each other in the presence of the selected sialyltransferase under conditions wherein the analogue of sialic acid is transferred to the acceptor. As is apparent, the saccharide or oligosaccharide acceptor employed must be one which functions as a substrate of the particular sialyltransferase employed.

In this regard, the art recognizes that while sialic acid is usually enzymatically transferred to a natural acceptor some sialyltransferases can tolerate certain modifications in the structure of the acceptor whereas other sialyltransferases show strict specificity for one type of acceptor83. The art also recognizes that artificial acceptors are tolerated in some cases by sialyltransferases especially where modification is in the aglycon part of the structure; modification in one or the sugar portion leads to results which are less predictable. For example, not all chemical modifications in the sugar portion of the acceptor can be tolerated. For example, $\beta$Gal(1→$\frac{3}{4}$)$\beta$GlcNAc-$\alpha$(2→3')sialyltransferase can transfer Neu-5Ac to terminal $\beta$Gal(1→$\frac{3}{4}$)$\beta$GlcNAc- disaccharides structure. However, in this situation, it has been found that the hydroxyl groups at the 4 and 6 positions of $\beta$-galactose are critical to recognition by this enzyme and accordingly chemical modification at one or more of these points can result in non-recognition of the modified oligosaccharide by the enzyme. On the other hand, extensive modifications are accepted at the 2 and 6 positions of the GlcNAc unit and some modification is accepted at the 2 position of $\beta$-galactose and at the 3 position of GlcNAc.

Likewise, when an analogue of sialic acid (i.e., an artificial donor) is to be enzymatically transferred, it is necessary that the CMP derivative of the analogue also be recognized by the sialyltransferase. In this regard, the art recognizes that certain sialyltransferases can tolerate some modifications to naturally occurring sialic acids and still transfer these analogues of sialic acid to glycoproteins or glycolipids possessing a suitable terminal acceptor structure.

Surprisingly, it has been found that sialyltransferases possess sufficient recognition flexibility so as to transfer an artificial donor to an artificial acceptor. Such flexibility permits the facile synthesis of a panel of oligosaccharide glycosides containing different analogues of sialic acid at the non-reducing sugar terminus of the oligosaccharide glycoside.

As noted above, a nucleotide derivative of a compatible analogue of sialic acid is combined with a compatible acceptor (i.e., a saccharide glycoside or an oligosaccharide glycoside having terminal saccharide unit(s) on the nonreducing end which are recognized by the selected sialyltransferase) in the presence of the sialyltransferase under conditions wherein the analogue is transferred to the acceptor. Suitable conditions, known in the art, include the addition of the appropriate sialyltransferase to a mixture of the compatible acceptor and of the CMP-derivative of the compatible sialic acid analogue in a appropriate buffer such as 0.1M sodium cacodylate in appropriate conditions of pH and temperature such as at a pH of 6.5 to 7.5 and a temperature between 25° and 45° C., preferably 35°-40° C. for 12 hours to 4 days. The resulting oligosaccharide can be isolated and purified using conventional methodology comprising HPLC, ion exchange-, gel-, reverse-phase- or adsorption chromatography.

Once formed, the alpha-sialylated oligosaccharide glycoside can be further modified by chemical and/or enzymatic means to further derivatize this compound. For example and as illustrated in the examples herein below, in some cases, L-fucose or a compatible analogue of L-fucose which is recognized by the transferase can be enzymatically transferred via a fucosyltransferase so as to provide for structures comprising those presenting a terminal Sialyl Lewis$^x$ or Sialyl Lewis$^a$ moieties. This example is not limiting insofar as other glycosyltransferases can be used to add a glycosyl group to an alpha sialylated oligosaccharide glycoside recognized by the transferase. This latter aspect is important insofar as the modifications made to the oligosaccharide glycoside must be compatible with the desired enzymatic transfers.

Additionally, the alpha sialylated oligosaccharide glycoside can be chemically modified to provide further derivatization of these compounds. As illustrated in the examples, such chemical modification includes reduction of a 9-azido group on an analogue of sialic acid to an amine group which can be still further functionalized to another derivative such as the 9-acetamido derivative. Similarly, the carboxyl group found on analogues of sialic acid can be selectively transformed on alpha sialylated oligosaccharide glycosides via lactonization, reduction or transformation into an amide.

In one or more of the enzymatic steps recited above, the enzyme can be bound to a solid support so as to facilitate the reaction of the reagents and the recovery of the product from the enzyme.

B5. Coupling of an Oligosaccharide Glycoside to an Antigenic Carrier

1. Coupling of an Alpha—Sialylated Oligosaccharide Glycoside to an Artificial Carrier Procedures for coupling (linking) an alpha sialylated oligosaccharide glycoside containing an aglycon having a functional group capable of linking to an antigenic carrier so as to form an artificial antigen are documented in the literature[63,64]. In general, such antigenic carriers contain at least one complementary reactive functional group which will react with the functional group on the aglycon (or a derivative thereof). Care should be taken to ensure that the functional groups and the coupling procedure employed is compatible with the nature of the oligosaccharide glycoside used and, in particular, with the functional groups present on the oligosaccharide glycoside (e.g., the carboxyl group on the sialic acid analogue). One suitable coupling procedure documented in the art employs a ester functionality (COOR' where R' is a leaving group or is transformable into a leaving group such as an alkyl of from 1 to 6 carbon atoms) on the aglycon which is transformed into an acyl azide ($—CON_3$) following known procedures. The azide can then be coupled to an antigenic carrier following known procedures[65,66].

Another suitable procedure employs an aglycon moiety having a terminal ethylenic group, preferably an activated terminal ethylenic group, such as an allyloxy group $—O—CH_2CH═CH_2$, which can then be activated by known methods in order to effect coupling to the carrier[67,68].

Once the aglycon functional group of the α-sialylated oligosaccharide glycoside has been activated, the coupling reaction is generally conducted by adding a molar amount or a substantial molar excess of this oligosaccharide glycoside to a composition containing the carrier under conditions whereby the functional group(s) or activated functional groups (if activation is necessary) on the aglycon react with a complementary reactive functional groups on the carrier. The amount of the alpha-sialylated oligosaccharide glycoside added in conjunction with the number of reactive sites on the carrier dictates the number of alpha-sialylated oligosaccharide glycoside substituents attached to each carrier and this number will vary with the selected carrier. In general, sufficient oligosaccharide glycoside is added so as to provide at least 1 such substituent per carrier. Preferably, the number of substituents is from 1 to about 60 per each carrier and more preferably, the number of substituents is from about 1 to about 20 per each carrier.

The examples herein below present specific procedures for coupling a carrier having a reactive functional group to an alpha-sialylated oligosaccharide glycosides having a complementary reactive functional group on the aglycon moiety or a functional group on the aglycon moiety which is capable of being activated (derivatized) to a complementary reactive functional group. These examples are non-limiting.

2. Coupling of an Oligosaccharide Glycoside to an Artificial Carrier followed by Addition of an Analogue of Sialic Acid via a Sialyltransferase As noted above, the coupling reactions useful in linking the alpha sialylated oligosaccharide glycoside to the artificial antigen is limited by the fact that the coupling reaction employed must not affect the sialic acid analogue in an unintended manner (e.g., at its —COOH group). To circumvent this restriction, it may be advantageous to first couple the asialo oligosaccharide glycoside to the antigenic carrier via its aglycon functionality and then enzymatically transfer an analogue of sialic acid to the artificial antigen containing one or more asialo oligosaccharide groups so as to provide for artificial antigens having pendent thereto one or more oligosaccharide groups containing an analogue of sialic acid at the non-reducing sugar terminus of the oligosaccharide. In this embodiment, an artificial antigen containing one or more asialo oligosaccharide groups is an artificial acceptor (as that term is defined herein) because the asialo oligosaccharide groups are not attached to the antigen through the hydroxyl group of the anomeric carbon atom of the reducing sugar but rather are attached through the aglycon functionality.

In this embodiment, the coupling of the asialo oligosaccharide glycoside to the antigenic carrier is achieved in the same manner as described above in Section B5 (A) above. Likewise, the enzymatic transfer of an analogue of sialic acid to the artificial antigen containing one or more asialo oligosaccharide groups is achieved in the same manner as described in Section B4 above.

B6. Coupling of an Alpha Sialylated Oligosaccharide Glycoside to Carriers other than Antigenic Carriers Small molecular weight carriers could provide di-, tri- or multivalent haptens with increased inhibitory potency. Appropriate sialylated polymeric carriers or co-polymerization of a sialylated monomer with an appropriate monomer could lead to non-immunogenic or biocompatible products. Artificial liposomes or micelles could be used as antigens, drug carriers or multivalent inhibitors. Accordingly, in addition to coupling to antigenic carriers, the alpha sialylated oligosaccharide glycosides described herein can be coupled to or incorporated with other carriers. For example, if the aglycon moiety of such oligosaccharide glycosides contains a hydrophobic group, then the oligosaccharide glycosides can be incorporated into micelles and liposomes.

Liposomes and micelles containing alpha sialylated oligosaccharide glycosides are useful for antigens or inhibitors of cellular adhesion phenomena/targeting.

Similarly, the carrier employed can be a solid phase particle containing one or more reactive functionalities and one or more alpha sialylated oligosaccharide glycosides containing a complementary reactive functional group on the aglycon can be coupled to the solid phase particle. Such coupling would proceed in a manner similar to that of Section B5 above. In this embodiment, the resulting solid phase particles would be useful in isolating enzymes (not sialyltransferases) lectins or other biological receptors from an aqueous solution containing such transferases. Solid phase particles containing reactive functional groups are well known in the art and include Sepharose, aminopropylsilica, aminopropyl—CPG (controlled pore glass), aminoethyl cellulose, Trisacryl ®-NH, glass beads, polyacrylamide particles, and the like.

The alpha sialylated oligosaccharide glycosides can also be coupled to larger molecular weight carriers of a polymeric nature which are chosen for their properties such as nonimmunogenicity, bio-compatibility and the ability to incorporate numerous alpha sialylated oligosaccharide glycoside groups per molecule of carrier. Examples illustrating the preparation of such polymeric carriers are set forth in the examples presented herein below.

Solid phase and polymeric carriers containing one or more alpha sialylated oligosaccharide glycosides are also useful, for example, in competitive immunoassays wherein the solid phase or polymeric carriers are added to a sample suspected of containing the natural substance. Antibodies raised against the modified alpha sialylated oligosaccharide glycoside and which cross-react with the natural substance are then added to the sample. Such antibodies are appropriately labeled so as to provide a detectable signal. The degree of binding of the labeled antibody to the solid phase or polymeric carrier depends on the amount of natural substance found in the sample. After incubation, the solid phase or polymeric carrier is then isolated from the sample and the amount of antibody bound to the carrier is ascertained by measuring the signal level. Correlation of the measured signal to standards permits an assessment of the level of natural antigen in the sample.

Additionally, non-immunogenic conjugates would be useful as inhibitors of cellular adhesion phenomena where multivalent conjugates are contemplated to be more effective inhibitors than monovalent haptens.

C. Utility

The methods of this invention are useful in preparing oligosaccharide glycosides containing an analogue of sialic acid bound via an α-linkage to the non-reducing sugar terminus of the oligosaccharide glycoside. In turn, such oligosaccharide glycosides are useful in suppressing a cellmediated immune response to an antigen[3].

Additionally, methods of this invention are useful in preparing oligosaccharide glycosides containing an analogue of sialic acid bound via an α-linkage to the non-reducing sugar terminus of the oligosaccharide glycoside which can be coupled to an antigenic carrier so as to produce artifical antigens. Accordingly, such oligosaccharide glycosides act as intermediates in the preparation of artifical antigens.

The artifical antigens can be injected into mice, for example, so as to produce antibodies which cross-react with the natural substance (i.e., a substance, e.g., antigen, having an alpha sialylated oligosaccharide group similar to that of the artifical antigen so that the sialyl analogue is generally the only change made in the terminal 2-4 sugars of oligosaccharide of the artifical antigen as compared to the sialic acid group of the oligosaccharide of the natural substance). Such antibodies can be used in immunoassay techniques for the purpose of determining the presence and/or level of the natural substance in a sample suspected of containing the natural substance.

In addition to the above, the antibodies (particularly monoclonal antibodies) can be used in antibody therapy for a particular natural antigen (i.e., a natural substance). Specifically, an artifical antigen can be synthesized so as to have one or more antigenic determinants similar to an antigenic determinant in the natural antigen. The antigenic determinant of such an artifical antigen is an oligosaccharide glycoside containing an analogue of sialic acid bound via an α-linkage to its non-reducing terminus. When injected into mice, the artifical antigen produces antibodies which cross-react with natural antigen. Such antibodies can then be collected and employed in antibody treatment for the natural antigen. Preferably, the antibodies are monoclonal antibodies. Methods of isolating a hybridoma line which generates monoclonal antibodies which recognize the antigenic determinant of the artifical antigen and which cross-react with a similar antigenic determinant on the natural antigen are well known in the art. Optionally, such antibodies can be coupled to therapeutic agents to enhance their therapeutic effectiveness.

Likewise, the utility for artificial conjugates other than artificial antigens has been set forth above.

The following examples are offered to illustrate this invention and are not to be construed in any way as limiting the scope of this invention.

In these examples, unless otherwise defined below, the abbreviations employed have their generally accepted meaning:

| | |
|---|---|
| AB = | AB pattern |
| AgOTF = | silver trifluoromethanesulphonate |
| ax = | axial |
| BSA = | bovine serum albumin |
| CMP = | cytidine-5-monophosphate |
| d = | doublet |
| dd = | doublet of doublets |
| ddd = | doublet of doublets of doublets |
| DTH = | delayed-type hypersensitivity |
| eq = | equatorial |
| Fuc T = | fucosyl transferase |
| GDP-Fuc = | guanosine-5-diphospho-L-fucose |
| i.r. = | infra red |
| m = | multiplet |
| phth = | phthalimido |
| q = | quartet |
| s = | singlet |
| ST = | sialyl transferase |
| t = | triplet |
| t.l.c. = | thin layer chromatography |
| U = | Units |
| μm = | microns |
| AG 1 × 8 (formate form) = | ion exchange resin AG 1 × 8 (formate form) available from Bio-Rad Laboratories, Richmond, CA |
| Dowex 50W × 8 ($H^+$ form) = | ion exchange resin Dowex 50W × 8 ($H^+$ form) available from Dow Chemical, Midland, MI |
| IR-C50 resin ($H^+$ form) = | ion exchange resin IR-C50 ($H^+$ form) available from Rohm & Haas, Philadelphia, PA |

Commercially available components are listed by manufacturer and where appropriate, the order number. Some of the recited manufacturers are as follows:

Iatron = Iatron Laboratories, Tokyo, Japan

Merck = E. Merck AG, Darmstadt, Germany

Millipore = Millipore Corp., Bedford, Mass.

Waters = Waters Associates, Inc., Milford, Mass.

EXAMPLES

In the following examples, Examples 1–13 illustrate the synthesis of numerous oligosaccharide glycosides whereas Examples 14–16 illustrate coupling of alpha sialylated oligosaccharide glycosides to carriers such as antigenic carriers, polymeric carriers, and the like.

Some of the examples set forth below are not true examples of this invention because they employ naturally occurring structures of sialic acid ("natural donors") rather than analogues of sialic acid ("artifical donors"). However, these examples are included herein for the purpose of exemplifying transfer of the sialic acid to the oligosaccharide glycoside via an appropriate sialyltransferase.

In Examples 1–16, the oligosaccharide glycosides recited are referred to by Arabic numerals which are depicted in FIGS. 1–15.

In one or more of Examples 1–16, pre-coated plates of silica gel (Merck, 60-$F_{254}$,) were used for analytical t.l.c. and spots were detected by charring after spraying with a 5% solution of sulfuric acid in ethanol. Silica gel 60 (Merck, 40–63 μm) was used for column chromatography. Iatrobeads were from Iatron (Order No. 6RS-8060). Millex-GV filters (0.22 μm) were from Millipore. $C_{18}$ Sep-Pak cartridges and bulk $C_{18}$ silica gel were from Waters Associates.

Commercial reagents were used in chemical reactions and solvents were purified and dried according to usual procedures. Unless otherwise noted, the reaction mixtures were processed by dilution with dichloromethane and washing with a dilute solution of sodium bicarbonate followed by water. After drying over magnesium sulfate, the solvents were removed by evaporation under vacuum with a bath temperature of 35° C. or lower when necessary.

$^1$H-n.m.r. were recorded at 300 MHz (BrukerAM-300) with either tetramethylsilane in $CDCl_3$ or acetone set at 2.225 in $D_2O$ as internal standards, at ambient temperature, unless otherwise noted. The chemical shifts and coupling constants (observed splittings) were reported as if they were first order, and only partial n.m.r. data are reported. $^{13}$C-n.m.r. spectra were recorded at 75.5 MHz with tetramethylsilane in $CDCl_3$ or dioxane set at 67.4 in $D_2O$ as reference.

A. SYNTHESIS OF ANALOGUES OF SIALIC ACID

Unless otherwise noted, analogues of sialic acid have been prepared following known procedures with suitable substitution of starting materials where necessary. The following derivatives have been prepared by a convenient modification of procedures reported in the literature: 9-$N_3$-Neu5Ac 1b,[39] Neu5Pr (5-propionamido) 1f, 7-d-Neu5Ac 1d[41] and the C8-Neu5Ac 1i[46].

FIG. 1 illustrates a general synthetic scheme used for the synthesis of analogues of sialic acid. Compounds referred to by underlined Arabic numerals in Examples 1–4 below are depicted Table A and in FIG. 1.

EXAMPLE 1

Synthesis of 5-acetamido-9-azido-3,5,9-tri-deoxy-D-glycero-D-galacto-2-nonulopyranosylonic acid (9-$N_3$-Neu5Ac) 1b Glycosyl chloride 38 (2.83 g, 5.57 mmol) in dry dichloromethane (13 mL) was added to the mixture of benzyl alcohol (5.0 mL, 48.2 mmol), molecular sieves 4Å (18.5 g, crushed), dry silver carbonate (4.2 g, 15.2 mmol) in dichloromethane (8 mL). The mixture was stirred in the dark for 4 days, diluted with dichloromethane ( 50 mL) and filtered through cellite. After usual work up, the residue was chromatographed on silica gel using a 3:2 mixture of hexanes and ethyl acetate as eluant. The product was then eluted with a 4:5 mixture of the same solvents giving (1.96 g, 60%) of pure material and 0.33 g (10%) of material containing a small amount of impurities. $^1$H-n.m.r.: 5.436 (ddd, 1H, $J_{7,8}$ 8.5, $J_{8,9}$ 2.5 Hz, H-8), 5.317 (dd, 1H, $J_{6,7}$ 1.8Hz, H-7), 5.110 (d, 1H, $J_{5,NH}$ 9.5 Hz, NH), 4.849 (ddd, 1H, $J_{3ax,4}$ 12.0, $J_{3eq,4}$ 4.5, $J_{4,5}$ 9.5Hz, H-4 ) , 4.788 and 4.397 (AB, 2H, $J_{gem}$ 12.0 Hz, benzy-lics), 3.642 (s, $CO_2CH_3$), 2.629 (dd, 1H, $J_{3\,eq,3ax}$ 12.5 Hz, H-3eq) , 2.140, 2.113, 2.017, 1.997, 1.857, (5s, 15H, 4 OAc, 1 NAc), 1.986 (dd, 1H, H-3ax).

The above material ( 1.5 g, 2.58 mmol ) was de-O-acetylated in dry methanol (20 mL) containing a catalytic amount of sodium methoxide for 5 hours at 22° C. After deionization with Dowex 50W X 8 ($H^+$ form), the solvent was evaporated leaving the product 39 (1.0 g, 94%) which was used in the next step; $^1$H-n.m.r. ($CDCl_3$): 4.815 and 4.619 (AB, 2H, $J_{gem}$ 11.5 Hz benzylics), 3.802 (s, $CO_2CH_3$), 3.582 (dd 1H $J_{5,6}$ 9.0, $J_{6,7}$ 0.5 Hz, H-6), 2.752 (dd, 1H, $J_{3eq,3ax}$ 12.5, $J_{3eq,4}$ 4.5 Hz, H-3eq), 2.039 (s, 3H, N Ac), 1.861 (dd, 1H, $J_{3ax,4}$ 11.0Hz, H-3ax).

A solution of para-toluenesulfonyl chloride (0.125 g, 0.65 mmol) in pyridine (0.1 mL) was syringed into a solution 39 (0. 248 g, 0.60 mmol), 4-dimethylaminopyridine (0.01 g) in pyridine (1.1 mL) at 0° C. After stirring for 4 hours at 0° C., methanol ( 0.10 mL) was added and the mixture was coevaporated with dry toluene. The residue was quickly chromatographed on silica gel using acetonitrile as eluant giving the tosylate (0.21 g, 62%) still containing some impurities. Sodium azide (0.19 g, 2.92 mmol) was added to a solution of this material (0.21 g, 0.37 mmol) in dimethylformamide (0.5 mL). The mixture was stirred at 65° C. for 18 hours after which it was filtered through celite and the solvent evaporated in vacuo. The residue was chromatographed on silica gel using a 6: 1 mixture of ethyl acetate and acetonitrile as eluant giving the product 40 (0.136 g, 85%); i.r.νcm$^{-1}$ 2110 ($N_3$); 1H-n m r: 5.775 (d, 1H, $J_{5,NH}$ 9 0Hz, NH), 4.816 and 4.470 (AB, 2H, $J_{gem}$ 11.5 Hz, benzylics), 3.738 (s, $CO_2CH_3$), 2.871 (dd, 1H, $J_{3eq,4}$ 4.8 $J_{3eq,3ax}$ 13.0Hz, H-3eq) , 2.086 (s, 3H, NAc), 1.964 (dd, 1H, $J_{3ax,4}$ 11.5 Hz, H-3ax).

The above compound 40 (0.105 g, 0.24 retool) was left for 3 hours at 22° C. in 0.25N sodium hydroxide (2 mL). After bringing the pH to 6 by addition of Dowex 50W X 8 ($H^+$ form) followed by filtration, the material, recovered after freeze drying, was chromatographed on Iatrobeads using a 65:35:5 mixture of chloroform, methanol and water as eluant. The appropriate fractions gave the product (0.087 g, 86%). This compound (0.100 g, 0.235 mmol) was heated at 80° C. for 6 hours in 0.025N hydrochloric acid (3 mL). The solution was neutralized with sodium hydroxide and then freeze dried. The product was chromatographed on Iatrobeads (0.60 g) using a 65:35:5 mixture of chloroform, methanol and water giving 1b (0.067 g, 85%); $^1$H-n.m.r.: 4.106–3.895 (m, 5H), 3.639 (dd, 1H, $J_{8,9}$ 3.0, $J_{9,9,}$ 13.0 Hz, H-9), 3.528 (dd, 1H, $J_{8,9,}$ 6.0 Hz, H-9'), 2.249 (dd, 1H, $J_{3eq,4}$ 4.5, $J_{3eq,3ax}$ 12.5 Hz, H-3eq), 2.090 (s, 3H, NAc), 1.852 (dd, 1H, $J_{3ax,4}$ 11.0Hz, H-3ax).

EXAMPLE 2

Synthesis of 5-propionamido-3,5-dideoxy-D-glycero-D-galacto-2-nonulopyranosylonic acid (Neu5Pr) 1f A solution of 39 (0.075 g, 0.18 mmol) in 2N sodium hydroxide (1 mL) was left for 0.5 hours at 22° C. followed by 7 hours at 95° C. The pH was then adjusted to 7.5 by addition of IR-C50 resin (H+ form). The filtrate obtained after filtration of the resin was evaporated in vacuo and the residue dried over phosphorous pentoxide.

Propionic anhydride ( 0.12 mL, 0.94 mmol ) was then syringed into a suspension of the above product in a mixture of dry methanol (1.5 mL) and triethylamine (0.2 mL) which was stirred at 0° C. After 3 hours, more propionic anhydride (0.025 mL, 0.195 mmol) was added and the mixture stirred for 2 more hours at 0° C. The mixture was co-evaporated with methanol, and a solution of the residue in water (2 mL) was passed through Dowex 50W X 8 (H+ form, 6 g). The recovered fractions were evaporated in vacuo and the residue chromatographed on Iatrobeads (5 g) using a 3:1 mixture of chloroform and methanol as eluant giving 41 ( 0. 0646 g, 86.5%); $^1$H-n.m.r.: 4.800, 4,578 (AB, 2H, $J_{gem}$ 11.0 Hz, benzylics), 3.580 (dd, 1H, $J_{5,6}$ 9.0, $J_{6,7}$ 1.0 Hz, H-6) 2.776 (dd, 1H, $J_{3eq,4}$ 4.5, $J_{3eq,3ax}$ 12.5 Hz, H-3eq), 2.316 (q, 2H, J 7.5 Hz, $CH_2CO$), 1.762 (dd, 1H, $J_{3ax,4}$ 12.0 Hz), 1.129 (t, 3H, $CH_3$).

A solution of the above benzyl glycoside (0.115 g, 0.278 mmol) in water (5 mL) was hydrogenated in the presence of 5% palladium on charcoal (10 mg) at atmospheric pressure and 22 ° C. for 5 hours. The eluate obtained after filtration through Celite followed by Millipore filter, was freeze dried leaving compound 1f (0.074 g, 82.5%); $^1$H-n.m.r.: 3.72–4.10 (m, H-4,-5,-7,-8,-9), 3.614 (dd, 1H, $J_{8,9a}$ 6.5, $J_{9a,9b}$ 11.75 Hz, H-9a) , 3. 530 (dd, 1H, $J_{5,6}$ 9.0 $J_{6,7}$ 1.0 Hz, H-6), 2.250–2.400 [m, 2H incl. $CH_2CO$ (q, 2.315, J 7.5 Hz) and H-3eq (dd, $J_{3eq,3ax}$ 11.5 Hz, $J_{3eq,4}$ 4.5Hz) ], 1.880 (t, 1H, $J_{3ax,3eq}$ 11.5Hz, H-3ax) , 1.130 (t, 3H, $CH_3$).

EXAMPLE 3

Synthesis of 5-acetamido-3,5-dideoxy-D-galacto-2-octulosonic acid (C8-Neu5Ac) 1i The synthesis of 1i from 39 essentially follows the published procedure of Hasegawa et al.[46] but using a different starting material than the reported one. In particular, a suspension of 39 (0.52 g, 0.125 mmol) in 2,2-dimethoxypropane (3 mL) was stirred for 1.5 hours at 22° C. in the presence of paratoluenesulfonic acid (0.5 mg). After neutralization with some triethylamine, the mixture was evaporated and the residue chromatographed on silica gel using a 16:1 mixture of chloroform and methanol giving 42 (0.049 g, 88%).

42 (0.054 g, 0.185 mmol) was acetylated in a 2:1 mixture of acetic anhydride (1 mL) and pyridine kept at 50° C. for 5 hours. After the usual work up, the residue was chromatographed on silica gel using ethyl acetate as eluant giving the acetylated product (0.091 g, 92%); $^1$H-n.m.r.: 5.420 (dd, 1H, $J_{6,7}$ 1.5, $J_{7,8}$ 3.5 Hz, H-7), 5.196 (d, 1H, $J_{5,NH}$ 9.0 Hz, NH), 5.009 (ddd, 1H, $J_{4,3ax}$ 13.0, $J_{4,3eq}$ 5.0, $J_{4,5}$ 10.0 Hz, H-4), 4.797 and 4.498 (AB, 2H, $J_{gem}$ 11.5 Hz, benzylics), 3.776 (s, 3H, $CO_2CH_3$), 2.724 (dd, 1H, $J_{3ax,3eq}$ 13.0Hz, H-3eq), 2.151, 2.032, 1.895 (3s, 9H, 2OAc, 1NAc), 2.032 (t, 1H, H-3ax), 1.363 and 1.350 (2s, 6H, methyls).

The above product (0.091 g, 0.169 mmol) was heated for 4 hours at 40° C. in 70% aqueous acetic acid. The mixture was co-evaporated with toluene in vacuo. The dry residue was dissolved in dry methanol and stirred for 2 hours at 22° C. in the presence of sodium metaperiodate (0.059 g, 0.275 mmol). The mixture was filtered through a pad of Celite which was washed with methanol. The combined filtrate was stirred at 0° C. for 25 minutes in the presence of sodium borohydride (0.036 g, 0.95 mmol). The mixture was then stirred at 0° C. with some acetic acid (0.2 mL), after which the solvents were evaporated leaving a residue which was dried in vacuo for 15 minutes and then acetylated in a 5:1 mixture of pyridine and acetic anhydride (6 mL) for 20 hours at 22° C. The residue recovered after the usual work up was chromatographed on silica gel using ethyl acetate as eluant to give a product which still contained some non-separable impurities. The dry material (0. 074 g, still containing some impurities) was dissolved in dry methanol ( 5 mL) and stirred at room temperature for 3 hours in the presence of sodium (3 mg). After de-ionization with Dowex 50W X 8 (H+ form) and filtration, the solvent was evaporated in vacuo and the residue chromatographed on silica gel using a 15:1 mixture of chloroform and methanol to give a pure product 44 (0.047 g, 78%); $^1$H-n.m.r.: ($CD_3OD$): 4.724 and 4.416 (AB, 2H, $J_{gem}$ 11.5 Hz, benzylics), 3.671 (s, 3H, $CO_2CH_3$), 3.456 (dd, 1H, $J_{5,6}$ 9.5, $J_{6,7}$ 1.0 Hz, H-6) , 2.642 (dd, 1H, $J_{3eq,4}$ 4.5, $J_{3eq,3ax}$ 12.5 Hz, H-3eq) , 1.938 (s, 3H, NAc), 1.699 (t, 1H, $J_{3ax,4}$ 12.5Hz, H-3ax).

The above material (0.022 g, 0.057 mmol) was stirred in 0.25N sodium hydroxide (2 mL) for 5 hours at 22° C., the solution was neutralized with Dowex 50W X 8 (H+ form) and the filtrate was freeze dried to give a white solid (0.019 g, 90%). This product was dissolved in water (2 mL) and hydrogenated for 3 hours at 22 ° C. in the presence of 5% palladium on charcoal (4 mg). The mixture was first filtered through Celite and then through a Millipore filter. The filtrate was freeze dried leaving the desired product (13.3 mg, 94); $^1$H-n.m.r.: 3.462–4.093 (m,6H), 2.287 (dd, 1H, $J_{3eq,4}$ 4.5 $J_{3eq,3ax}$ 12.5Hz, H-3eq), 2.052 (s, 3H, NAc), 1 853 (t, 1H, $J_{3eq,4}$ 12.5 Hz H-3ax)

EXAMPLE 4

Synthesis of 5-acetamido-3,5,7-trideoxy-β-D-galacto-2-nonulopyranosylonic acid (7-d-Neu5Ac) 1d The synthesis of 1d essentially follows the published procedure of Zbiral et al.[41] but using a different starting material. In particular, imidazole (0.13 g, 1.93 mmol) and tert-butyldimethylsilyl chloride (0.135 g, 0.89 mmol) were added to a solution of 42 (0.11 g, 0.19 mmol) in dimethylformamide (2 mL). After 4 hours at room temperature, the solvent was removed in vacuo, the residue dissolved in chloroform and worked up as usual. Chromatography of the product on silica gel using a 1:1 mixture of ethyl acetate and hexane provided the monosilylated derivative (0.101 g, 92%): $[\alpha]_D=-2.66$ (c. 0.6, chloroform); $^1$H-n.m.r.: 5.195 (d, 1H, $J_{5,NH}$ 7 Hz, NH), 4. 853 and 4. 603 (AB, 2H, $J_{gem}$ 11.5 Hz, benzylics), 3.736 (s, $CO_2CH_3$), 2.692 (dd, 1H, $J_{3eq,4}$ 4.5, $J_{3eq,3ax}$ 13.0 Hz, H-3eq), 2.022 (s, 3H, NAc), 1.884 (dd, 1H, $J_{3ax,4}$ 11.0 Hz, H-3ax), 1.405, 1.375 (2s, 6H, methyls), 0.868 (s, 9H, t-butyl), 0.093 and 0.084 (2s, 6H, methyls).

Sec-butyl lithium (1.3 M in cyclohexane, 0.65 mL, 0.85 mmol) followed by carbon disulfide (1.25 mL, 20.8 mmol) were added dropwise to a solution of the above compound (0.437 g, 0.77 mmol) in dry tetrahydrofuran (20 mL) at −30° C. After stirring at −25° C. for 0.5 hours, methyl iodide (1.6 mL, 25.6 mmol ) was slowly warmed up to room temperature. After evaporation, the residue was chromatographed on silica gel using a 4:1 mixture of hexanes and ethyl acetate as eluant providing the xanthate (0.327 g, 65%): $[\alpha]_D$ 93.9 (c. 0.655, chloroform); $^1$H-n.m.r.: 6.388 (dd, 1H $J_{6,7}$ 1.0, $J_{7,8}$ 2.5 Hz, H-7), 5.610 (d, 1H, $J_{5,NH}$ 7.0Hz, NH), 4.778, 4.466 (AB, 2H, $J_{gem}$ 11.5Hz, benzylics) , 3.778 (s, $CO_2CH3$) , 2.662 (dd, 1H, $J_{3eq,4}$ 4.5, $J_{3eq,3ax}$ 12.5 Hz, H-3eq), 2.584 (s, 3H, $CH_3$), 1.883 (s, 3H, NAc), 1.693 (dd, 1H, $J_{3ax,4}$ 11.5 Hz, H-3ax), 1.315 (s, 6H, methyls), 0.825 (9H, t-butyl), 0.025, 0.092 (2s, 6H, methyls).

Azobisisobutyronitrile ( 0. 004 g) and tri-n-butyltin hydride (0.5 mL, 1.86 mmol) were added to a solution of the above xanthate ( 0.32 g, 0.48 mmol) in dry toluene ( 3 mL). After heating at 100° C. for 7 hours, the solvents were coevaporated with dry toluene, and the residue chromatographed on silica gel using a 3:2 and then 1:1 mixtures of hexane and ethyl acetate as eluant to give the 7-deoxy product (0.260 g, 70%); $^1$H-n.m.r.: 5.334 (d, 1H, $J_{5,NH}$ 7.0 Hz, NH), 4.740, 4.455 (AB, 2H, $J_{gem}$ 11.6 Hz, benzylics), 3.690 (s, $CO_2CH_3$), 2.628 (dd, 1H, $J_{3eq,4}$ 4.2, $J_{3eq,3ax}$ 12.9Hz, H-3eq), 1.914 (s, 3H, NAc), 1.805 (dd, 1H, $J_{3ax,4}$ 10.9 Hz, H-3ax) , 1. 718 and 1. 597 (m, 2H, H-7 and H-7'), 1.325 (s, 6H, methyls), 0.804 (9H, t-butyl), 0.010, 0.009 (2s, 6H, methyls). The above compound (0.260 g, 0.47 mmol) was heated at 75° C. in 70% acetic acid for 7.5 hours. After co-evaporation with toluene, the residue was chromatographed on silica gel using a 10:1 mixture of chloroform and methanol giving 43 (0.157 g, 84%); $^1$H-n.m.r.: 4.860 and 4.655 (AB, 2H, $J_{gem}$ 11.5 Hz, benzylics), 3.834 (s, $CO_2CH_3$), 2.806 (dd, 1H, $J_{3eq,4}$ 4.5, $J_{3eq,3ax}$ 12.5 Hz, H-3eq), 2.069 (s, 3H, NAc), 1.881 (dd, 1H, $J_{3ax,4}$ 12.5 Hz, H-3ax), 1.698 (m, 2H, H-7 and H-7 ').

Compound 43. (0.157 g, 0.396 mmol) was kept in 0.25N sodium hydroxide (6 mL) at room temperature for 5 hours. After neutralization with Dowex 50W X 8 (H+ form) and filtration, the product (0.149 g, 97%) was recovered after lyophilization of the solution. This product (0.146 g, 0.38 mmol) was hydrogenated in water (5 mL) for 5 hours at room temperature in the presence of 5% palladium on charcoal (0.010 g). The mixture was filtered through Celite and through a Millex-GV (0.22 μm) filter. The filtrate was freeze dried to provide 1d (0.105 g, 94%); $^1$H-n.m.r.: as reported by Christian[56].

Table A summarizes the analogues of sialic acid prepared:

TABLE A

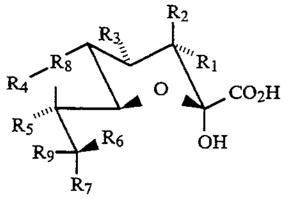

| Compound No. | R1 | R2 | R3 | R4 | R5 | R6 | R7 | R8 | R9 |
|---|---|---|---|---|---|---|---|---|---|
| | | | | Sialic Acid Derivatives | | | | | |
| 1a | H | H | OH | NHAc | H | OH | OH | H | $CH_2OH$ |
| 1b | " | " | " | " | " | " | " | " | $CH_2N_3$ |
| 1c | " | " | " | " | " | " | " | " | $CH_3$ |
| 1d | " | " | " | " | " | H | " | " | $CH_2OH$ |
| 1e | " | " | " | " | OH | H | " | " | " |
| 1f | " | " | " | $NHCOCH_2CH_3$ | H | OH | " | " | " |
| 1g | " | " | " | OH | " | " | " | " | " |
| 1h | " | " | " | $NHCOCH_2OH$ | " | " | " | " | " |
| 1i | " | " | " | NHAc | " | " | " | " | H |

B. SYNTHESIS OF CMP DERIVATIVES OF ANALOGUES OF SIALIC ACID

EXAMPLE 5

Synthesis of the CMP-derivatives of Neu5Ac

CMP-sialic acid synthase was extracted from calf brain and partially purified at 4° C. by a slight modification of the original procedure of Higa et al.[28] Routinely, ~200 g of brain tissue were homogenized in a Cuisinart blender (three 30 second bursts with 1 minute intervals) with 400 mL of 25 mM Tris/HCl, pH 7.5, 10 mMmagnesium chloride, 10 mM sodium chloride, 2.5 mM dithioerythritol, 0.5 mM phenylmethylsulfonyl fluoride. The homogenate was stirred for 1 hour and then centrifuged at 23,000×g for 15 minutes. The supernatant was decanted and the pellets were extracted once again with 200 mL of the same buffer as above. The supernatants were combined and centrifuged at 28,000×g for 15 minutes. The supernatant was filtered through glass wool to give the crude extract (515 mL, 4.7 mg protein/mL, ~90 U of enzyme).

After adjusting salt concentration to 0.4M with solid potassium chloride, the crude extract was stirred and solid ammonium sulfate was added to 35% saturation (208 g/L) over a period of 15 minutes. The solution was stirred for an additional 15 minutes, kept on ice for 1 hour and centrifuged at 28,000×g for 30 minutes. The precipitate was discarded and the supernatant was stirred and adjusted to 60% saturation by the addition of solid ammonium sulfate (163 g/L) over 15 minutes.

After an additional 15 minutes of stirring, the suspension was left on ice overnight and then centrifuged as above. The resultant pellets were washed with 150 mL of 60% ammonium sulfate solution to remove the co-precipitates. The washed pellets contain 70–80 U of enzyme with a specific activity of 0.08 U/mg protein. The enzyme was assayed as described by Kean et al.[70], with one unit of enzymatic activity defined as one μmol of product formed per minute at 37° C.

The enzyme present in the pellet could be stored for several weeks in the cold room. Before using the enzyme for synthesis, the pellets were suspended in a minimal volume of 50 mM Tris/HCl, pH 9.0, 35 mM magnesium chloride, 3 mM 2mercaptoethanol (activation buffer) and dialyzed overnight against 100 volumes of the same buffer. The dialyzed enzyme was centrifuged at 9,000×g for 10 min. The supernatant containing more than 90% of the enzyme activity was used directly for the synthesis.

The CMP-derivatives of sialic acid analogues were synthesized as noted above and purified by a modification of the reported procedures of Higa et al.[28] and Gross et al.[71] For example, 7-d-Neu5Ac 1d (Table A, 20 mg, 69 μmol) was activated by using 15 U of the above dialyzed enzyme for 5–6 hours at 37° C. in 12 mL of the activation buffer in the presence of four fold excess of cytidine triphosphate. When appropriate, the conversion of the sialic acid analogues was estimated by the usual thiobarbituric acid assay for sialic acid after reduction with sodium borohydride as per Kean et al.[70] The product was extracted with cold acetone as per Gross et al.[71] After evaporation of the acetone in vacuo (at ~15° C.), the concentrated solution was applied to a column of Bio-Gel P-2 (2.5×91 cm) equilibrated and eluted with 10 mM ammonium hydroxide at 4° C. with a flow rate of 60 mL/h. Fractions (1 mL) were assayed for cytidine by absorbance at 273 nm, and the fractions corresponding to the first peak were pooled, concentrated in vacuo and the residue was freeze-dried leaving the CMP-7-d-Neu5Ac (2d, 30 mg, ~94%). This material showed a very small amount of impurities by $^1$H-n.m.r. (Table B) and was used directly for the reaction with sialyltransferases. In some cases (2e, 2g, 2h), $^1$H-n.m.r. spectra showed that the CMP-derivatives contained some of the unreacted sialic acid.

Table B below illustrates the CMP-derivatives of analogues of Neu5Ac prepared from the analogues of Neu5Ac set forth in Table A above as well as partial $^1$H-n.m.r. data concerning these compounds.

TABLE B

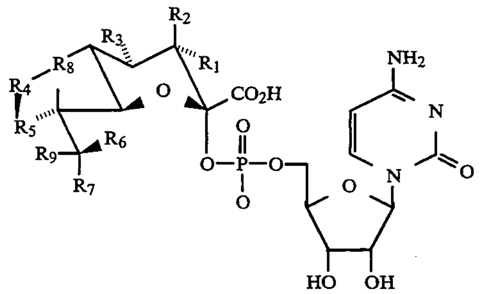

2

| CMP-Sialic Acid Derivatives | | | | | | | | | Comp. p |
|---|---|---|---|---|---|---|---|---|---|
| R1 | R2 | R3 | R4 | R5 | R6 | R7 | R8 | R9 | No. |
| H | H | OH | NHAc | H | OH | OH | H | $CH_2OH$ | 2a |
| " | " | " | " | " | " | " | " | $CH_2N_3$ | 2b |
| " | " | " | " | " | " | " | " | $CH_3$ | 2c |
| " | " | " | " | " | H | " | " | $CH_2OH$ | 2d |
| " | " | " | " | OH | H | " | " | " | 2e |
| " | " | " | $NHCOCH_2CH_3$ | H | OH | " | " | " | 2f |
| " | " | " | OH | " | " | " | " | " | 2g |
| " | " | " | $NHCOCH_2OH$ | " | " | " | " | " | 2h |
| " | " | " | NHAc | " | " | " | " | H | 2i |

$^1$H-n.m.r. Data and Reaction Data for CMP-sialic Acid Derivatives

| Sialic Acid Analogue | CMP-Derivative | Conversion[2] (%) | Ribose H-1 (d) | Cytidine H-5 (d) | Cytidine H-6 (d) | R-4 | H-3eq (dd) | H-3ax (ddd) | Other |
|---|---|---|---|---|---|---|---|---|---|
| 1b | 2b | 70 | 5.98 | 6.12 | 7.97 | NHAc 2.05(s) | 2.48 | 1.64 | |
| | | | | | | | (4.0; 13.5) | (6.0; 13.0; 13.5) | |
| 1c | 2c | 90 | 5.98 | 6.19 | 8.05 | NHAc 2.05(s) | 2.48 | 1.64 | H-9 |
| | | | | | | | (4.2; 13.0) | (6.0; 12.0; 13.0) | 1.23(d, 6.5) |
| 1d | 2d | NA | 5.99 | 6.15 | 8.03 | NHAc 2.05(s) | 2.52 | 1.65 | H-7 |
| | | | | | | | (4.5; 13.5) | (5.7; 12.5; 13.0) | 1.60(m) |
| 1e | 2e | 70 | 5.98 | 6.13 | 7.98 | NHAc 2.05(s) | 2.53 | 1.70 | |
| | | | | | | | (4.5; 13.2) | (12.0; 13.2) | |
| 1f | 2f | 62 | 5.97 | 6.12 | 7.98 | $NHCOCH_2CH_3$[3] | 2.48 | 1.65 | |
| | | | | | | | (4.0; 13.0) | (6.0; 12.0; 13.0) | |
| 1g | 2g[4] | 35 | 5.99 | 6.13 | 7.98 | OH | 2.44 | 1.60 | |
| 1h | 2h | 44 | 5.98 | 6.11 | 7.96 | $NHCOCH_2OH$ | 2.49 | 1.65 | |
| | | | | | | 4.12(s) | (4.7; 12.5) | (5.6; 12.5; 13.0) | |
| 1i | 2i | 94 | 5.97 | 6.11 | 7.97 | NHAc 2.05(s) | 2.48 | 1.64 | |
| | | | | | | | (4.0; 13.2) | (5.6; 12.5; 13.0) | |

[1]in $D_2O$ with DOH set at 4.80
[2]thiobarbituric assay
[3]2.31(q, 7.5Hz, $CH_2$); 1.33(t, $CH_2$)
[4]coupling constants not accurately obtained due to poor resolution.

C. SYNTHESIS OF OLIGOSACCHARIDE GLYCOSIDE ACCEPTORS

Examples 6–7 illustrate the synthesis of oligosaccharide glycoside acceptors which can then be used with a compatible sialyltransferase so as to provide for alpha sialylated oligosaccharide glycosides. The structure of 3b to 7a are illustrated in FIG. 2.

Oligosaccharide glycosides 4b, 5b, 5f, 6a, and 7a were synthesized according to the procedures of Lemieux et al.[72], Lemieux et al.[73], Paulsen et al.[74], Sabesan et al.75, and Lemieux et al.[77] respectively.

Oligosaccharide glycosides 4d and 5d were synthesized following the procedure reported for the synthesis of oligosaccharide glycosides 4b and 5b but by replacing the 8-methoxycarbonyloctyl by methanol. Oligosaccharide glycosides 5e and 5g were synthesized according to the procedures of Paulsen et al.[74] and Alais et al.[76] but replacing the methanol by 8-methoxycarbonyloctanol. In all cases, the oligosaccharide glycosides were purified by chromatography on Iatrobeads with the appropriate solvent mixtures and the recovered materials chromatographed on BioGel P2 or Sephadex LH20 and eluted with water. The recovered materials were lyophilized from water and the products further dried in vacuo over phosphorus pentoxide.

EXAMPLE 6

Synthesis of 9-Hydroxynonyl 2-acetamido-2-deoxy-[β-D-galactopyranosyl—(1-3)-O-]-β-D-glucopyranoside 4a Sodium acetate (0.200 g) and sodium borohydride (0.060 g) were added to a solution of the disaccharide 4b (0.100 g, 0.189 mmol) in a 10:1 mixture of water and methanol (20 mL) cooled at +4° C. After 24 hours, more sodium borohydride (0.020 g) was added to the reaction mixture maintained at +4° C. After 48 hours at the same temperature, the pH was brought to 5–6 by addition of acetic acid. The solution was then co-evaporated with an excess of methanol. The residue was dissolved in water (10 mL) and run through a column of $C_{18}$ silica gel which was further washed with water. After elution with methanol, the solvent was evaporated in vacuo. The residue was dissolved in a 10:1 mixture of water and methanol and the pH brought to 13–14 by addition of 1N sodium hydroxide. The mixture was left at room temperature until t.l.c. (65:35:5—chloroform, methanol and water) indicated the disappearance of the unreacted starting material 4b. The mixture was then neutralized by addition of Dowex 50W X 8 ($H^+$ form) and the resin filtered off. The resulting solution was run through a column of AG 1×8 (formate form). The eluate was freeze dried and the residue was run through Sephadex LH 20 using a 1:1 mixture of water and ethanol. The appropriate fractions were pooled and concentrated to give 4a (0.060 g, 65%); $^1$H-n.m.r. (D2O): 4.545 (d, 1H, $J_{1,2}$ 8.0 Hz, H-1), 4. 430 (d, 1H, $J_{1',2'}$, 7.5 Hz, H-1'), 2.025 (s, 3H, NAc), 1. 543 (m, 4H), and 1. 304 (m, 10H): methylenes; $^{13}$C-n.m.r. ($D_2O$): 175.3 (Ac) , 104.36 (C-1') , 101.72 (C-1) , 67.72, 61.85, 61.60 (three $CH_2OH$).

EXAMPLE 7

9-Hydroxynonyl 2-acetamido-2-deoxy-[β-D-galactopyranosyl-(1-4)-O-]-β-D-glucopyranoside 5a Oligosaccharide glycoside 5a was prepared from 5b as indicated above (60%); $^1$H-n.m.r. ($D_2O$): 4.520 (d, 1H, $J_{1,2}$ 7.5 Hz, H-1), 4.473 (d, 1H, $J_{1',2'}$7.6 Hz, H-1'), 2.033 (s, 3H, NAc), 1.543 (m, 4H) and 1.302 (m,10H):methylenes; $^{13}$C-n.m.r. ($D_2O$): 175.23 (Ac), 103.71 and 101.88 (C-1 and C-1'), 60.93, 61.85 and 62.71 (three $CH_2OH$).

EXAMPLE 8

Synthesis of 5-Allyloxypentyl 2-acetamido-2-deoxy-[β-D-galactopyranosyl—(1-3)-0-]-β-D-glucopyranoside 4c The synthetic schemes for this example and Example 9 are set forth in FIG. 3.

a. Synthesis of Allyloxy-5-pentanol 29

Allyl bromide (2.5 mL, 0.029 mol) was added dropwise to the mixture of 1,5-pentanediol (3 g, 0.029 mol) and sodium hydride (1.2 g, 80% dispersion in oil) in dry dimethylformamide. Stirring was continued overnight at room temperature. Tol.c. (2:1 - toluene and ethyl acetate) still indicated the presence of some unreacted pentanediol. The unreacted sodium hydride was destroyed by addition of methanol. The mixture was concentrated to 50 mL by evaporation in vacuo. After dilution with methylene chloride (150 mL), the solvents were washed with water (three times), dried over magnesium sulfate and evaporated in vacuo. The residue was chromatographed on silica gel using a 2:1 mixture of toluene and ethyl acetate as eluant. The appropriate fractions gave compound 29 (0.931 g, 30%). $^1$H-n.m.r. ($CDCl_3$): 5.83 (m, 1H, —CH═), 5.20 (m, 2H, ═$CH_2$), 3.95 (dd, 1H, J=5.5 and 1.0 Hz, allylics), 3.66 and 3.46 (two t, 2H each, J=6.5 Hz, O—$CH_2$), 1.64 (m, 4H) and 1.44 (m, 2H): methylenes); $^{13}$C-n.m.r.($CDCl_3$): 134.7 and 116.6 (ethylenics), 71.6, 70.1 ($CH_2$—O—CH2), 62.1 ($CH_2OH$) 32.2, 29.2 and 22.2 (methylenes).

b. Synthesis of 5-Allyloxypentyl 2-deoxy-2-phthalimido-β-D-glucopyranoside 32

A solution of 3,4,6-tri-O-acetyl-2-deoxy-2-phthalimido-D-glucopyranosyl bromide 30 (5.0 g, 10.0 mmol) in dichloromethane (5 mL) was added dropwise to a mixture of the alcohol 29 (1.33 mL, 10 mmol), silver trifluoromethanesulphonate (2.57 g, 10.0 mmol) and collidine (1.23 mL, 9.0 mmol) in dichloromethane ( 10 mL) at −70 ° C. After stirring for 3 hours at −70°, t.l.c. (2:1-toluene and ethyl acetate) indicated that the starting bromide and the reaction product had the same Rf. After addition of some triethylamine, the reaction mixture was diluted with dichloromethane and worked up as usual. The syrupy residue was chromatographed on silica gel using a 5:1 mixture of toluene and ethyl acetate providing compound 31 (4.0 g, 71%). $^1$H-n.m.r. ($CDCl_3$): 5.80 (m, 2H, —CH═ and H-3), 5.36 (d, 1H, $J_{1,2}$ 8.5 Hz, H-1), 5.18 (m, 3H, ═$CH_2$ and H-4), 2.13, 2.06, 1.87 (3s, 3H each, 3OAc), 1.40 (2H) and 1.15 (m, 4H): methylenes.

A 0.2M solution of sodium methoxide in methanol (0.500 mL) was added dropwise to a solution of compound 32 (4.00 g, 7.1 mmol) in dry methanol (30 mL) cooled at 0° C. The mixture was stirred at 0 ° C. for 2 hours until t.l.c. (10:1 chloroform and methanol) indicated the disappearance of the starting material. The reaction mixture was de-ionized with Dowex 50W X ($H^+$ form, dry) at 0 ° C. Filtration and evaporation of the solvent left a residue which was purified by chromatography on silica gel using a 100:5 mixture of chloroform and methanol as eluant providing compound 32 (2.36 g, 76%). $^1$H-n.m.r. ($CDCl_3$): 7.70 and 7.80 (m, 4H, aromatics), 5.82 (m, 1H, —CH═), 5.17 (m, 3H, ═$CH_2$ and H-1), 1.38 and 1.10 (m, 6H, methylenes); $^{13}$C-n.m.r. ($CDCl_3$): 134.9 and 116.6 (ethylenics), 98.3 (C-1), 56.6 (C-2).

c. Synthesis of 5-Allyloxypentyl 4,6-O-benzylidene-2-deoxy-2-phthalimido-β-D-glucopyranoside 33

Paratoluenesulfonic acid monohydrate (0.025 g) was added to a solution of 32 (1.0 g, 2.3 mmol) and α,α-dimethoxytoluene (0.690 mL, 4.6 mmol) in dry dimethylformamide. After stirring for 2 h at 40° C., t.l.c. (10:1—chloroform and methanol) indicated the completion of the reaction. After addition of a small amount of triethylamine, most of the solvent was evaporated in vacuo and the residue diluted with dichloromethane and worked up as usual. After evaporation of the solvents, the residue was chromatographed on silica gel using a 9:1 mixture of toluene and ethyl acetate giving compound 33 (1 36 g, 90 1%) $[\alpha]_D^{20}+24.1$ (c 0 5 chloroform); $^1$H-n.m.r. ($CDCl_3$): 7.15–7.90 (m, 9H, aromatics), 5.83 (m, 1H, —CH═), 5.56 (s, 1H, benzylidene), 5.10–5.37 [m, 3H, ═$CH_2$ and H-1 (5.25, d, $J_{1,2}$ 8.5 Hz)], 1.40 (m, 2H) and 1.17 (m, 4H): methylenes.

d. Synthesis of 5-Allyloxypentyl4,6-O-benzylidene-2-deoxy-[2,3,4,6-tetra-O-acetyl-β-D-galactopyranosyl-(1-3)-O-]-2-phthalimido-β-D-glucopyranoside 35

A solution of trimethylsilyltrifluoromethanesulfonate (0.1 mL of a solution made from 0.050 mL of the reagent in 1.0 mL of dichloromethane) was syringed into a mixture of compound 33 (1.20 g, 2.29 mmol), 2,3,4,6-tetra-O-acetyl-α-D-galactopyranosyl acetimidate 34 (1.70 g, 3.50 mmol) and molecular sieves (0.500 g, crushed in a 1:1 mixture of toluene and dichloromethane (30 mL) cooled to −20° C. The mixture was stirred at −20° C. for 0.5 hours and slowly brought to 0° C. in 1 hour. T.l.c. (1:1 hexane and ethyl acetate) indicated the completion of the reaction. Some triethylamine was added and after dilution with methylene chloride and filtration, the solvents were worked up in the usual manner. After evaporation, the residue was applied on a column of silica gel by using toluene and elution was then continued with a 2:1 mixture of hexane and ethyl acetate. The appropriate fractions gave the disaccharide 35 (1.63 g, 74%). $[\alpha]_D^{20}+4.1$ (c, 0.5 $CHCl_3$); $^1$H-n.m.r. ($CDCl_3$): 7.40–8.00 (m, 9H, aromatics) , 5.85 (m, 1H, —CH═) , 5.58 (s, 1H, benzylidene) 5.07–5.25 (m, 4H, incl. ═$CH_2$, H-4' and H-1) , 5.00 (dd, 1H, $J_{1',2'}$8.0, $J_{2',3'}$10.0 Hz, H-2'), 2.11, 1.90, 1.85, 1.58 (4s, 12H, 4OAc) , 1.37 and 1.12 (m, 6H, methylenes); $^{13}$C-n.m.r. ($CDCl_3$): 134.6 and 117.0 (ethylenics) , 102.1, 101.2, 99.4 (benzylidene, C-1 and C-1').

e. Synthesis of 5-Allyloxypentyl 2-deoxy-[2,3,4,6-tetra-O-acetyl-β-D-galactopyranosyl—(1-3)-O-]-2-phthalimido-β-D-glucopyranoside 36

A solution of the disaccharide 35 (1.63 g, 1.91 mmol) in 90% aqueous acetic acid (10 mL) was heated at 70° C. for 1 h at which time t.l.c. (100:5—chloroform and methanol) indicated the completion of the reaction. Co-evaporation with an excess of toluene left a residue which was chromatographed on silica gel using a 100:2 mixture of chloroform and methanol as eluant giving compound 36 (1 12 g, 76%) $[\alpha]_D^{20}$ +9.3 (C 0.55 $CHCl_3$); $^1$H-n.m.r. ($CDCl_3$): 7.70–7.95 (m, 4H, aromatics), 5.82 (m, 1H, —CH═), 5.33 (dd, 1H, $J_{3',4'}$ 3.5, $J_{4',5'}$ 1.0 Hz, H-4'), 5.10–5.27 (m, 3H, incl. ═$CH_2$ and H-2'), 5.07 (d, 1H, $J_{1,2}$ 8.5 Hz, H-1) , 4.84 (dd, 1H, $J_{2',3'}$ 10.0 Hz, H-3') , 2.10, 2.08, 1.90 (3s, 9H, 3OAc), 1.05–1.47 (m, 9H, incl. 1OAc). $^{13}$C-n.m.r. ($CDCl_3$): 100.3 and 97.5 C-1 and C-1'.

Anal.calcd: C, 56.88; H, 6.17; N, 1.83. Found: C, 55.59; H, 6.20; N, 1.84.

f. Synthesis of 5-Allyloxypentyl 2-acetamido-2-deoxy-[β-D-galactopyranosyl—(1-3)-O-]-β-D-glucopyranoside 4c Sodium borohydride (0.690 g, 18 mmol) was added to the disaccharide 36 (0.700 g, 0.91 mmol) in a 5:1 mixture of isopropanol and water (20 mL). The mixture was stirred for 24 hours at room temperature after which t.l.c. (65:35:5, chloroform, methanol and water) showed the disappearance of the starting material. After addition of acetic acid (8.2 mL) the mixture was heated for 3 hours at 100° C. The mixture was co-evaporated with an excess of toluene and the dried residue acetylated in a 3:2 mixture of pyridine and acetic anhydride (5 mL) in the presence of dimethylamino-pyridine for 24 hours at 22° C. After addition of some methanol, the mixture was diluted with dichloromethane worked up as usual leaving a residue which was co-evaporated with some toluene. The final syrup was chromatographed on silica gel using a 100:2 mixture of chloroform and methanol giving the peracetylated disaccharide (0. 500 g, 71%). $^1$H-n.m.r. ($CDCl_3$): 5.90 (m, 1H, —CH═), 5.77 (d, 1H, $J_{2,NH}$ 7.5 Hz, NH), 5.37 (dd, 1H, $J_{3',4'}$ 3.5, $J_{4',5'}$ 1.0 Hz, H-4'), 5.15–5.23 (m, 2H, ═$CH_2$), 1.95–2.18 (7s, 21H, 6OAc, 1 NAc), 1.58 (m, 4H) and 1.41 (m, 2H): methylenes.

A 0.5N solution of sodium methoxide (0.300 mL) was syringed into a solution of the above compound (0.500 g, 0.623 mmol) in dry methanol ( 20 mL). After stirring overnight at room temperature, the mixture was de-ionized with Dowex 50W X (H+ form, dried) and evaporated in vacuo. The residue was dissolved in methanol and coated on Celite (3 g) by evaporation of the solvent. The Celite was then applied on top of a column of Iatrobeads (30 g) and the product eluted with a 65:25:1 mixture of chloroform, methanol and water giving the disaccharide 4c (0.266 g, 80%); $[\alpha]_D^{20}$-0.164 (c.l, water); $^1$H-n.m.r. ($D_2O$): 5.95 (m, 1H, —CH═), 5.30 (m, 2H, ═$CH_2$), 4.548 (d, 1H, $J_{1,2}$ 7.7 Hz, H-1), 4.426 (d, 1H, $J_{1',2'}$ 7.7 Hz, H-1'), 4.031 (dd, 1H, J 1.0, 11.5 Hz, allylics), 2.023 (s, 3H, NAc), 1.58 (m, 4H) and 1.38 (m, 2H): methylenes; $^{13}$C-n.m.r. ($D_2O$): 175.24 (carbonyl) , 134.70 and 119.05 (ethylenics), 104.33 (C-1'), 101.68 (C-1), 55.42 (C-2).

EXAMPLE 9

Synthesis of 5-Allyloxypentyl 2-acetamido-2-deoxy-β-D-glucopyranoside 37

The starting material 32 (0.300 g, 0.689 mmol) was deprotected as indicated previously for compound 36. The crude material recovered after peracetylation was chromatographed on silica gel using a 1:1 mixture of hexane and ethyl acetate which gave the peracetylated derivative (0.180 g, 55%), $[\alpha]_D^{20}$ +11.5 (c, 0.7, chloroform); $^1$H-n.m.r. ($CDCl_3$): 5.90 (m, 1H, —CH═), 5.64 (d, 1H, $J_{2,NH}$ 8.5 Hz, NH), 4.68 (d, 1H, $J_{1,2}$ 7.5Hz, H-1), 1.95, 2.03 (two), 2.05 (3s, 12H, 3 OAC, 1 NAc), 1.58 (m, 4H) and 1.41 (m, 2H): methylenes.

Anal. calcd.: C, 55.8; H, 7.5; N, 2.05. Found: C, 55.82; H, 7.53; N, 2.98.

This material was de-O-acetylated in methanol (5 mL) to which a 0.5N solution of sodium methoxide in methanol (0.100 mL) was added. After overnight at room temperature, the mixture was de-ionized with IR—C50 resin (H+ form, dry) and the solvents evaporated. The residue was run through Iatrobeads using a 7:1 mixture of chloroform and methanol giving the pure 37 (0 103 g, 80%), $[\alpha]_D^{20}$ -0.17 (c 1, water); $^1$H-n.m.r. ($D_2O$): 5.85 (m, 1H, —CH=), 5.29 (m, 2H,—CH=), 4.50 (d, 1H, $J_{1,2}$ 8.5 Hz, H-1), 4.03 (d, 2H, J 6.0 Hz, allylics), 2.033 (s, 3H, NAc), 1.58 (m, 4H) and 1.36 (m, 2H): methylenes; $^{13}$C-n.m.r. ($D_2O$): 175.2 (carbonyl) , 134.7 and 119.1 (ethylenes), 101.9 (C-1), 61.6 (C-6), 56.4 (C-2), 29.1, 23.0 and 22.6 (methylenes).

D. TRANSFER OF ANALOGUES OF SIALIC ACIDS TO OLIGOSACCHARIDE GLYCOSIDES

EXAMPLE 10

Transfer of Analogues of Sialic Acids Oligosaccharide Structures via Glycosyltransferases This example demonstrates the enzymatic transfer of Neu5Ac and analogues thereof onto oligosaccharide glycoside structures via sialyltransferases. The purpose of this example is to demonstrate that analogues of sialic acid (artificial donors) can be transferred to oligosaccharide glycosides in the same manner as Neu5Ac by use of a compatible sialyltransferase. FIGS. 4, 5, 6, 7 and 8 illustrate these transfers and provide structures for the prepared compounds identified by an underlined arabic numeral. In Examples 10a–10e, preparative sialylation was performed as follows:

Preparative Sialylation

Sialic acids, activated as their CMP-derivatives (as set forth in Examples 1–5 above), were transferred onto synthetic oligosaccharide structures containing βGal(1-3)GlcNAc-, βGal(1-4)βGlcNAc-, βGal(1-3)βGalNAc-, and βGal(1-4)βGlc-terminal sequences by using three mammalian sialyltransferases (Ex. 10a–e). The βGal(1$\frac{3}{4}$)βGlcNAc α(2-3') sialyltransferase (EC 2.4.99.5) and the βGal (1-4)βGlcNAc α(2-6')sialyltransferase (EC 2.4.99.1) from rat liver were purified to homogeneity by affinity chromatography according to the procedure of Mazid et al.[69], which is incorporated herein by reference. The βGal(1-3)αGalNAc α(2-3')sialyltransferase (EC 2.4.99.4) was purchased from Genzyme Corporation, Norwalk, Conn.

In all preparative sialylation reactions, the acceptor oligosaccharide (5–20 mg) was incubated with the selected CMP-sialic acids (5–20 mg) in the presence of the appropriate sialyltransferase (10–50 mU) and calf intestine alkaline phosphatase (Boehringer Mannheim, Mannheim, Germany) as in the procedure of Unverzagt et al.[78] for 37° C. for 24–48 hours in 50 mM sodium cacodylate pH 6.5, 0.5% Triton CF-54, 1 mg/mL BSA ("sialyl transfer buffer"). For example, the sialyloligosaccharide 7-d-αNeu5Ac(2-6)βGal(1-4)βGlcNAc-O-$(CH_2)_8$—$COOCH_3$ (13d, 4.4 mg) was synthesized by incubation of βGal(1-4)βGlcNAc-O-$(CH_2)_8$—$COOCH_3$ (5b, 4.6 mg) and CMP-7-d-Neu5Ac (2d, 15.6 mg) in the presence of βGal(1-4)βGlcNAc α(2-6') sialyltransferase (51 mU) and calf intestine alkaline phosphatase (2.4 U) for 28 hours at 37° C. in 2.5 mL of the sialyl transfer buffer (see Examples 1–5). After completion, the reaction mixture was diluted to 10 mL and passed onto three Sep-Pak $C_{18}$ cartridges, conditioned as suggested by the manufacturer. Each cartridge was washed with water (4×5 mL) and then with methanol (3×5 mL). The methanol eluate was evaporated to dryness in vacuo and the residue was dissolved in a 65:35:3 mixture of chloroform, methanol and water (0.5 mL—solvent I) and applied on to a small column of Iatrobeads (500 mg) equilibrated in the same solvent. The column was successively eluted with solvent I followed by a 65:35:5 mixture of chloroform, methanol and water (solvent II) and then by a 65:35:8 mixture of chloroform, methanol and water (solvent III). The appropriate fractions (30 drops) containing the product, as identified by t.l.c. on silica gel plates (with a 65:35:8 mixture of chloroform, methanol and 0.2% calcium chloride solution as eluant), were pooled together and concentrated to dryness in vacuo. The residue was run through a small column of AG 50W-X8 ($Na^+$ form), the eluate freeze-dried and the recovered product characterized by $^1$H-n.m.r. which, in all cases, indicated good purity.

In some cases, after sialylation of the oligosaccharide glycoside with an analogue of sialic acid via a sialyltransferase, the alpha sialylated oligosaccharide glysocide can be further enzymatically modified by addition of another saccharide unit. Exemplary of such saccharide units is L-fucose which is added via a compatible fucosyltransferase. FIGS. 4, 5, and 6 illustrate these transfers and provide structures for the prepared compounds identified by an underlined arabic numeral. In Examples 10a–10e, preparative fucosylation was performed as follows:

Preparative Fucosylation

Sialylated analogues of the type I and II oligosaccharides can be further fucosylated by the human milk βGlcNAc α(1$\frac{3}{4}$) fucosyltransferase. The enzyme was purified from human milk according to the methodology using affinity chromatography on GDP-hexanolamine Sepharose described by Palcic et al.[79] The synthesis and purification of the fucosylated oligosaccharides was carried out by a modification of the procedures of Palcic et al.$^F$79 For example, the fucosylated structure 9-$N_3$-αNeu5Ac(2-3)βGal (1-3)-[α-L-Fuc(1-4)]-βGlcNAc-O-$(CH_2)_8$—$CH_2OH$ 17b was synthesized by incubating GDP-fucose (2.5 mg) and 9-$N_3$-αNeu5AC(2-3)βGal(1-3)βGlcNAc-O-$(CH_2)_8$—$CH_2OH$ 8b (1.7 mg) with affinity purified βGlcNAc- α(1$\frac{3}{4}$)fucosyltransferase (4.6 mU) in 1.3 mL of 100 mM sodium cacodylate (pH 6.5), 10 mM manganese chloride, 1.6 mM ATP, 1.6 mM sodium azide. After 27 hours at 37° C., 2.5 mg of GDP-fucose and 2.3 mU of the fucosyltransferase were added to the reaction mixture, which was kept at 37° C. for an additional 21 hours. The product was isolated as described above for the sialylation reaction. T.l.c. of the crude material (as above) indicated that the fucosylation was almost complete. After purification and chromatography on AG 50W x 8 ($Na^+$ form), 1H-n.m.r. of the product 17b (1.0 mg) indicated a very good purity (Table E). In some cases where the fucosyltransferase was not highly purified, partial hydrolysis of the methyl ester of the linking arm occurred. Examples 10a–10e are as follows:

Example 10a: this example refers to the transfer of modified sialic acids such as 1a–g to the 3—OH of a terminal βGal of acceptors possessing a βGal(1-3)βGlcNAc- (Lewis$^C$ or Type I) terminal structure such as 4a and 4b by a sialyltransferase such as the βGal(1$\frac{3}{4}$)βGlcNAc α(2-3')sialyltransferase from rat liver following the experimental procedure reported above. The $^1$H-n.m.r. data of the reaction products, which were purified as indicated previously, are reported (Tables C and D).

Example 10b: this example refers to the transfer of modified sialic acids such as 1b and 1c to the 3—OH of the terminal βGal of acceptors possessing a βGal(1-4)βGlcNAc(LacNAc or Type II) terminal structure such as 5a, b, d–g by a sialyltransferase such as that used in 10a. The [1]H-n.m.r. data of the reaction products, which were purified as indicated previously, is reported (Tables F, H). In some cases, dimethylsulfoxide (5% volume) may be added to solubilize the acceptor. The reaction mixture was worked up in the manner described previously.

Example 10c: this example refers to the transfer of modified sialic acids such as 1c to the 3—OH structure of the terminal βGal of acceptors possessing a βGal(1-4)βGlc-(lactose) terminal structure such as 6a by a sialyltransferase such as that used in Example 10a following the same experimental procedure. The [1]H-n.m.r. data of the reaction products, which were purified as indicated previously, is reported (Table F).

Example 10d: this example refers to the transfer of modified sialic acids such as 1b-h to the 6—OH of the terminal βGal of acceptors possessing a βGal(1-4)βGlcNAc(LacNAc or Type II) terminal unit such as 5b, d-g by a sialyltransferase such as the βGal(1-4)βGlcNAc-α(2-6')sialyltransferase reported previously. The [1]H-n.m.r. data of the reaction products, which were purified as indicated previously, is reported (Tables G, H).

Example 10e: this example refers to the transfer of modified sialic acids such as 1c to the 3—OH of the terminal βGal of acceptors possessing a βGal(1-3)βGalNAc- ("T") terminal unit such as 7a by a sialyltransferase such as the βGal(1-3)eGalNAc-α(2-3)sialyltransferase (Genzyme)following the experimental procedure reported previously. The [1]H-n.m.r. data of the reaction products, which were purified as indicated previously, is reported (Table I).

TABLE C

[1]H-n.m.r. Data of Sialyloligosaccharides Obtained by Transfer of Sialic Acids on the Acceptor 4a by the βGal(1$^{3}_{4}$)βGlcNAc α(2-3)Sialyltransferase, and by Chemical Modification

| | | Sialic Acid | | | | β Gal | | |
|---|---|---|---|---|---|---|---|---|
| Sialic Acid | Reaction Product | H-3eq(dd) ($J_{3eq,3ax}$; $J_{3eq,4}$) | H-3ax(t) ($J_{3ax,4}$) | R5 | Other | H-1(d) ($J_{1,2}$) | H-3(dd) ($J_{2,3}$;$J_{3,4}$) | H-4 (d) |
| 1b | 8b | 2.756 (12.5, 4.6) | 1.775 (12.5) | NHAc | — | 4.485 (7.7) | 4.065 (10.0; 3.1) | |
| 1c | 8c | 2.756 (12.0; 4.0) | 1.771 (12.0) | NHAc | H-9 1.254 (d, 6.3) | 4.473 (8.0) | 4.058 (9.7, 3.5) | — |
| 1d | 8d | 2.720 (12.5, 3.5) | 1.800 (12.0) | NHAc | H-7 (1) (m) | 4.500 (7.6) | 4.080 (9.7; 3.0) | 3.945 |
| 1f | 8f | 2.763 (12.5, 4.5) | 1.785 | NHCOCHCH$_2$CH$_3$: 2.295(q, 7.7) 1.114(t) | — | 4.496 (7.5) | 4.083 (10.0; 3.5) | |
| 1j | 8j | 2.742 (12.0; 4.2) | 1.810 (12.2) | NHAc | (2) | 4.510 (7.5) | 4.076 (9.7; 3.0) | 3.982 |
| 1k | 8k | 2.755 (12.0; 4.5) | 1.792 (12.0) | NHAc | — | 4.494 (7.7) | 4.072 (9.8; 3.3) | |
| 1m | 8m | 2.698 (12.0, 4.0) | 1.757 (12.0) | NHAc | — | 4.497 (7.6) | 4.085 (9.7; 3.1) | 3.980 |

| Sialic Acid | Reaction Product | βGlcNAc H-1(d) ($J_{1,2}$) | NHAc | CO$_2$CH$_3$ (s) | (CH$_2$)$_8$ (two m) | CH$_2$—CO$_2$ (t, J=7.5) |
|---|---|---|---|---|---|---|
| 1b | 8b | 4.556 (8.1) | 2.034 (two) | NA | 1.546; 1.308 | NA |
| 1c | 8c | 4.558 (7.5) | 2.028; 2.034 | " | 1.542; 1.304 | " |
| 1d | 8d | 4.552 (7.7) | 2.022; 2.018 | " | 1.548; 1.305 | " |
| 1f | 8f | 4.555 (7.5) | 2.026 (one) | " | 1.548; 1.305 | " |
| 1j | 8j | 4.562 (7.7) | 2.032 (two) | " | 1.547, 1.309 | " |
| 1k | 8k | 4.552 (7.8) | 2.020; 2.032 (three) | " | 1.546; 1.308 | " |
| 1m | 8m | 4.553 (7.8) | 2.024 (two) | " | 1.541; 11.306 | " |

(1) overlapping signals 1.500-1.730
(2) H-9a: 3.110(dd, 2.8, 13.2); H-9b: 2.792(dd, 8.3, 13.2)

TABLE D

[1]H-n.m.r. data of Sialyloligosaccharides Obtained by Transfer of Sialic Acids on the Acceptor 4b by the βGal(1$^{3}_{4}$)βGlcNAc α(2-3) Sialyltransferase

| | | Sialic Acid | | | | β Gal | | |
|---|---|---|---|---|---|---|---|---|
| Sialic Acid | Reaction Product | H-3eq(dd) ($J_{3eq,3ax}$; $J_{3eq,4}$) | H-3ax(t) ($J_{3ax,4}$) | R5 | Other | H-1(d) ($J_{1,2}$) | H-3(dd) ($J_{2,3}$;$J_{3,4}$) | H-4 |
| 1c | 9c | 2.756 (12.5; 4.5) | 1.769 (12.5) | NHAc | H-9 1.252 (d, 6.3) | 4.469 (7.9) | 4.057 (9.7; 3.0) | |
| 1e | 9e | 2.740 (12.5, 4.5) | 1.779 (12.2) | NHAc | 4.017 dd | 4.500 (7.7) | 4.125 (9.7; 3.0) | |
| 18 | 9g | 2.710 (12.0; 4.2) | 1.726 (12.2) | HO | — | 4.481 (7.7) | 4.064 (10.0; 3.0) | |
| 1i | 9i | 2.705 (12.5; 4,5) | 1.768 (12.0) | NHAc | — | 4.494 (7.7) | 4.050 (10.0; 3.0) | |

| Sialic | Reaction | βGlcNAc H-1(d) | CO$_2$CH$_3$ | (CH$_2$)$_8$ | CH$_2$—CO$_2$ |
|---|---|---|---|---|---|

TABLE D-continued

| $^1$H-n.m.r. data of Sialyloligosaccharides Obtained by Transfer of Sialic Acids on the Acceptor 4b by the $\beta$Gal(1$\frac{3}{4}$)$\beta$GlcNAc $\alpha$(2-3) Sialyltransferase | | | | | | |
|---|---|---|---|---|---|---|
| Acid | Product | ($J_{1,2}$) | NHAc | (s) | (two m) | (t, J=7.5) |
| 1c | 9c | 4.551 (8.1) | 2.030 (two) | 3.687 | 1.567; 1.299 | 2.390 |
| 1e | 9e | 4.552 (7.7) | 2.047 1.996 | 3.689 | 1.560; 1.299 | 2.390 |
| 18 | 9g | 4.540 (7.7) | 2.023 (one) | 3.689 | — | 2.390 |
| 1i | 9i | 4.559 (8.0) | 2.035 (two) | 3.685 | 1.560; 1.290 | 2.389 |

TABLE E $^1$H-n.m.r. Data of Sialyl Lewis$^a$ (CA19-9, 17) and of Sialyl Lewis$^a$ 18 Structures.

| | | Sialic Acid | | | | $\beta$Gal | | |
|---|---|---|---|---|---|---|---|---|
| Sialic Acid | Reaction Product | H-3eq(dd) ($J_{3eq,3ax}$; $J_{3eq,4}$) | H-3ax(t) ($J_{3ax,4}$) | R5 | Other | H-1(d) ($J_{1,2}$) | H-3(dd) ($J_{2,3}$;$J_{3,4}$) | H-4(d) |
| 1b | 17b | 2.767 (12.5; 4.5) | 1.757 (12.2) | NHAc | — | 4.520 (1) (7.7) | (2) | (2) |
| 1k | 17k | 2.770 (12.5; 4.5) | 1.755 (12.0) | NHAc | H-9a(dd) 3.270 (13.5; 7.5) | 4.530 (1) (8.0) | (2) | (2) |
| 1m | 17m | 2.709 (12.0; 4.4) | 1.749 (12.0) | NHAc | — | 4.528 (1) (8.8) | (2) | (2) |
| 1c | 18c | 2.757 (12.5; 4.5) | 1.782 (12.4) | NHAc | H-9, 1,273 (d, 6.5) | 4.514 (1) (7.5) | 4.027 (3.0; 10.8) | (2) |
| 1l | 18l | 2.770 (2) (4.1) | 1.918 (12.5) | NHAc | $CONHCH_3$ (3) | 4.518 (1) (7.5) | 4.027 (3.0; 10.8) | (2) |

| | | $\beta$GlcNAc | $\alpha$Fuc | | | | | | |
|---|---|---|---|---|---|---|---|---|---|
| Sialic Acid | Reaction Product | H-1(d) ($J_{1,2}$) | H-1(d) ($J_{1,2}$) | H-5(q) ($J_{5,6}$) | H-6(d) ($J_{5,6}$) | NHAc | $CO_2CH_3$ (s) | $(CH_2)_3$ (two m) | $CH_2CO_2$ (t, J=7.5) |
| 1b | 17b | 4.536 (1) (8.5) | 5.010 (3.6) | 4.870 (6.5) | 1.169 (6.5) | 2.059; 2.031 | N.A. | 1.546; 1.308 | N.A. |
| 1k | 17k | 4.530 (1) (8.0) | 5.010 (3.5) | (2) | 1.170 (6.5) | 2.025 (three) | N.A. | 1.570; 1.300 | N.A. |
| 1m | 17m | 4.558 (1) (7.7) | 5.011 (6.5) | (2) | 1.175 (6.5) | 2.049; 2.023 | N.A. | 1.540; 1.304 | N.A. |
| 1c | 18c | 4.520 (1) (7.5) | 5.100 (3.8) | (2) | 1.165 (6.5) | 2.028 2.014 | 3.688 | 1.550; 1.300 | 2.385 |
| 1l | 18l | 4.529 (1) (7.5) | 5.100 (3.8) | (2) | 1.169 (6.5) | 2.035 2.015 | N.A. (3) | 1.545 1.285 | $CH_2CONH$ 2.225 |

(1) interchangeable
(2) overlapping with other signals
(3) $CH_3NHCO$ (2.708 and 2.797, two s)

TABLE F $^1$H-n.m.r Data of Sialyloligosaccharides Obtained by Transfer of Sialic Acids on the Acceptors 5a, 5b and 6a by the $\beta$Gal(1$\frac{3}{4}$)$\beta$GlcNAc $\alpha$(2-3)Sialyltransferase.

| | | | Sialic Acid | | | | $\beta$ Gal | | |
|---|---|---|---|---|---|---|---|---|---|
| Sialic Acid | Acceptor | Reaction Product | H-3eq(dd) ($J_{3eq,3ax}$; $J_{3eq,4}$) | H-3ax(t) ($J_{3ax,4}$) | R5 | Other | H-1(d) ($J_{1,2}$) | H-3(dd) ($J_{2,3}$;$J_{3,4}$) | H-4 |
| 1b | 5a | 10b | 2.758 (12.5, 4.4) | 1.790 (12.0) | NHAc | — | 4.540 (8.0) | 4.099 (9.5; 3.0) | (2) |
| 1c | 5b | 11c | 2.749 (12.5, 4.5) | 1.794 (12.1) | NHAc | H-9 1.219(d, 6.6) | 4.540 (7.7) | 4.099 (10.0; 3.1) | (2) |
| 1a | 6a | 14a | 2.760 (12.5, 4.7) | 1.798 (12.0) | NHAc | — | 4.529 (1) (8.0) | 4.113 (10.0, 3.0) | |
| 1c | 6a | 14c | 2.752 (12.5, 4.3) | 1.795 (12.5) | NHAc | H-9 1.268(d, 6.5) | 4.517 (1) (8.0) | 4.100 (10.0; 2.8) | (2) |

| Sialic Acid | Acceptor | Reaction Product | $\beta$GlcNAc $\beta$Glc H-1(d) ($J_{1,2}$) | NHAc | $CO_2CH_3$ (s) | $(CH_2)_8$ (two m) | $CH_2$—$CO_2$ (t, J=7.5) |
|---|---|---|---|---|---|---|---|
| 1b | 5a | 10b | 4.520 (7.0) | 2.030; 2.034 | NA | 1,570; 1.310 | NA |
| 1c | 5b | 11c | 4.513 (7.7) | 2.029 (two) | 3.685 | 1.560; 1.297 | 2.389 |
| 1a | 6a | 14a | 4.475 (1) (8.0) | 2.030 (one) | 3.687 | 1.609 1.314 | 2.387 |
| 1c | 6a | 14c | 4.478 (1) | 2.029 | 3.685 | 1.600; | 2.378 |

TABLE F-continued $^1$H-n.m.r Data of Sialyloligosaccharides Obtained by Transfer of Sialic Acids on the Acceptors 5a, 5b and 6a by the βGal(1$\frac{3}{4}$)βGlcNAc α(2-3)Sialyltransferase.

| | | |
|---|---|---|
| (8.2) | (one) | 1.312 |

(1) interchangeable
(2) overlapping with other signals

TABLE G $^1$H-n.m.r. data of Sialyloligosaccharides Obtained by Transfer of Sialic Acids on the Acceptor 5b by the βGal(1-4)βGlcNAc α(2-6)Sialyltransferase

| Sialic Acid | Reaction Product | Sialic Acid: H-3eq(dd) ($J_{3eq,3ax}$; $J_{3eq,4}$) | H-3ax(t) ($J_{3ax,4}$) | R5 | Other | β Gal H-1(d) ($J_{1,2}$) | βGlcNAc H-1(d) ($J_{1,2}$) | NHAc | $CO_2CH_3$ (s) | $(CH_2)_8$ (two m) | $CH_2$—$CO_2$ (t, J=7.5) |
|---|---|---|---|---|---|---|---|---|---|---|---|
| 1b | 13b | 2.660<br>(12.2; 4.5) | 1.706<br>(12.0) | NHAc | — | 4.442<br>(7.8) | 4.550<br>(8.0) | 2.033;<br>2.054 | 3.680 | 1.550;<br>1.289 | 2.388 |
| 1c | 13c | 2.665<br>(12.5; 4.5) | 1.708<br>(12.0) | NHAc | H-9 1.266<br>(d, 6.3) | 4.446<br>(7.7) | 4.549<br>(7.7) | 2.029<br>2.055 | 3.680 | 1.556;<br>1.300 | 2.389 |
| 1d | 13d | 2.676<br>(12.4; 4.0) | (1) | NHAc | H-7(m)<br>(1) | 4.455<br>(7.6) | 4.549<br>(7.1) | 2.048<br>2.022 | 3.688 | (1);<br>1.302 | 2.307 |
| 1e | 13e | 2.654<br>(12.1; 4.4) | 1.718<br>(12.0) | NHAc | — | 4.441<br>(7.7) | 4.551<br>(8.1) | 1.992<br>2.059 | 3.691 | 1.560;<br>1.305 | 2.390 |
| 1f | 13f | 2.672<br>(12.5; 4.5) | 1.715<br>(12.0) | $NHCOCH_2CH_3$:<br>2.294(q, 7.6);<br>1.113(t) | — | 4.447<br>(7.5) | 4.554<br>(7.6) | 2.055<br>(one) | 3.685 | 1.554;<br>1.299 | 2.389 |
| 1g | 13g | 2.623<br>(13.0; 4.0) | 1.660<br>(12.0) | HO | — | 4.435<br>(7.5) | 4.545<br>(7.5) | 2.056<br>(one) | 3.688 | 1.560;<br>1.300 | 2.390 |
| 1h | 13h | 2.688<br>(12.7; 4.9) | 1.730<br>(12.0) | $NHCOCH_2OH$:<br>4.115(s) | — | 4.450<br>(8.1) | 4.553<br>(7.7) | 2.055<br>(one) | 3.680 | 1.558;<br>1.305 | 2.787 |

(1) overlapping signals 1.500–1.730

TABLE H $^1$H-n.m.r. data of Sialylogliogsaccharides Obtained by Transfer of Sialic Acids on the Acceptor 5g by the βGal(1$\frac{3}{4}$)βGlcNAc α(2-3)sialyltransferase (I) and the βGal(1-4)βGlcNAc α(2-6) sialyltransferase (II)

Acceptor: 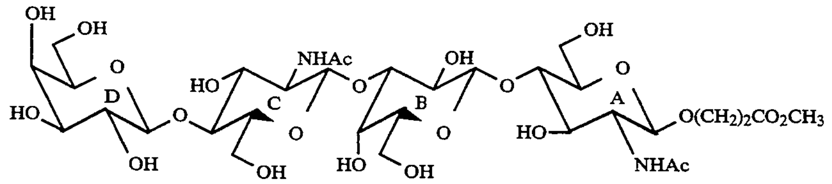 5g

| Sialic Acid | En-zyme | Reaction Product | Sialic Acid: H-3eq (dd) | H-3ax (t) | Other | H-1 (C) (d) | H-3 (D) (dd) | H-1 (A,B,D) (d) | H-4 (B) | NHAc | $COCH_3$ (s) | $CH_2CO_3$ t, J=7.5 |
|---|---|---|---|---|---|---|---|---|---|---|---|---|
| 1a | I | 12a | 2.755<br>(4.5;<br>12.0Hz) | 1.795<br>(12.0Hz) | — | 4.695<br>(8.0Hz) | 4.112<br>(3.0;<br>10.0Hz) | 4.552; 4.513;<br>4.455 (8.0; 7.5;<br>8.0Hz) | 4.152<br>(2.7Hz) | 2.020<br>(three) | 3.695 | 2.382 |
| 1a | II | 14a | 2.670<br>(4.5;<br>12.0Hz) | 1.720<br>(12.1Hz) | — | (1) | N.A. | 4.485; 4.460;<br>(three,<br>7.5Hz) | 4.155<br>(2.7Hz) | 2.018<br>2.050 | 3.685<br><br>(three) | 2.389 |
| 1g | II | 14g | 2.623<br>(4.5;<br>13.0Hz) | 1.658<br>(12.5Hz) | — | (1) | N.A. | 4.515; 4.464;<br>4.439(7.5Hz) | 4.156<br>(2.7Hz) | 2.027<br>2.057<br>(two) | 3.690 | 2.387 |

(1) overlapping with other signals

TABLE I $^1$H-n.m.r. Data of Sialyloligosaccharides Obtained by Transfer of Sialic Acids on the Acceptors 7a by the βGal(1-3)αGalNAcα(2-3)Sialyltransferase.

| Sialic Acid | Reaction Product | Sialic Acid: H-3eq(dd) ($J_{3eq,3ax}$; $J_{3eq,4}$) | H-3ax(t) ($J_{3ax,4}$) | R5 | Other | βGal: H-1(d) ($J_{1,2}$) | H-3(dd) ($J_{2,3}$;$J_{3,4}$) | H-4 ($J_{4,5}$) |
|---|---|---|---|---|---|---|---|---|
| 1c | 16c | 2.749<br>(11.9, 5.0) | 1.777<br>(12.3) | NHAc | H9 1.259<br>(d, 6.6) | 4.538<br>(8.09) | (1) | (1) |

| Sialic Acid | Reaction Product | αGalNAc: H-1(d) ($J_{1,2}$) | H-2(dd) ($J_{2,3}$) | H-4(d) ($J_{3,4}$) | NHAc | $CO_2CH_3$ (s) | $(CH_2)_8$ (two m) | $CH_2CO_2$ (t, J=7.5) |
|---|---|---|---|---|---|---|---|---|
| 1c | 16c | 4.905 | 4.278 | 4.233 | 2.029 | 3.689 | 1.560; | 2.388 |

TABLE I-continued

| $^1$H-n.m.r. Data of Sialyloligosaccharides Obtained by Transfer of Sialic Acids on the Acceptors 7a by the βGal(1-3)αGalNAcα(2-3)Sialyltransferase. | | | | |
|---|---|---|---|---|
| (3.60) | (11.0) | (3.5) | (two) | 1.300 |

(1) overlapping with other signals

E. PREPARATION OF ANALOGUES OF ALPHA SIALYLATED OLIGOSACCHARIDE GLYCOSIDES BY FURTHER CHEMICAL MODIFICATION

Examples 11–13 below describe the synthesis of further analogues of alpha sialylated oligosaccharide glycosides by the chemical modification of alpha sialylated oligosaccharide glycoside structures. FIGS. 9–11 illustrate the reaction schemes involved in the preparation of these analogues and provide structures for the prepared analogues which are identified by an underlined arabic numeral.

EXAMPLE 11

Synthesis of 9-Hydroxynonyl (5-acetamido-3,5-dideoxy-β-L-arabino-2-heptulopyranosylonic acid)-(2-3)-O-β-D-galactopyranosyl-(1-3)-O-[α-L-fucopyranosyl-(1-4)-O-]-2-acetamido-2-deoxy-β-D-glucopyranoside 17m The starting trisaccharide 8a (1.3 mg) was stirred for 24 hours at +4° C. in 1.7 mL of a solution 0.05M in sodium acetate and 0.010M in sodium periodate. The excess of sodium periodate was then destroyed by addition of some ethylene glycol. Sodium borohydride (20 mg) was then added and the stirring was continued for 24 hours at 4° C. The pH of the reaction mixture was then brought to 6 by addition of acetic acid and the solvents were co-evaporated with methanol. The residue was dissolved in water (1 mL) and run through a Sep-Pak cartridge which was further washed with water followed by methanol. The methanol eluate was evaporated and the residue chromatographed on Iatrobeads (200 mg) using a 65:35:5 mixture of chloroform, methanol and water as eluant. The appropriate fractions were pooled and evaporated leaving the product 8m (1 mg); $^1$H-n.m.r.: see Table C above.

Trisaccharide 8m was enzymatically fucosylated following the procedure reported in Example 10 and the product purified in the same manner. T.l.c. of the recovered crude material indicated that the transformation of 8m was almost complete. Purification gave 17m (0.5 rag); $^1$H-n.m.r.: see Table 5 above.

EXAMPLE 12

Synthesis of 9-Hydroxynonyl (5,9-diacetamido-3,5,9-tri-deoxy-α-D-glycero-D-galacto-2-nonulopyranosylonic acid)-(2-3)-O-β-D-galactopyranosyl-(1-3)-O-[α-L-fucopyranosyl-(1-4)-O-]-2-acetamido-2-deoxy-β-D-glucopyranoside 17k A solution of the trisaccharide 8b (1 mg) in water (0.5 mL) was hydrogenated at 22° C. at atmospheric pressure in the presence of Lindlar catalyst (1.0 mg, Aldrich Chemical Company, Milwaukee, Wis.) for 15 minutes T.l.c. (65:35:8—chloroform, methanol and 0.2% calcium chloride), indicated a complete transformation. The mixture was filtered through Celite and the solid extensively washed with water. The filtrate was concentrated, filtered through Millipore filter and the eluate freeze dried leaving the trisaccharide 8j; $^1$H-n.m.r.: see Table C above.

Acetic anhydride (about 0.2 mg) in methanol (10 μL) was added to a solution of 8j (about 1 mg) in a 1:1 solution of 0.002N sodium hydroxide and methanol (0.300 mL) at 0° C. T.l.c. (solvent as above) indicated a complete reaction and the solvents were then evaporated. The residue was dissolved in water (2 mL) and applied to a Sep-Pak cartridge. The cartridge was washed with water and the product eluted with methanol giving the trisaccharide 8k (about 1 mg); $^1$H-n.m.r.: see Table C above.

Trisaccharide 8k was enzymatically fucosylated following the procedure reported in Example 10 and the product purified in the same manner. T.l.c. of the recovered crude material indicated that the transformation of 8k was almost complete. Purification gave 17k (about 0.5 mg); $^1$H-n.m.r.: see Table E above.

EXAMPLE 13

Synthesis of 8-N-methylamidooctyl (5-acetamido-3,5-dideoxy-α-D-glycero-galacto-2-nonulo-pyranosylonic acid N-methylamide)-(2-3)-O-β-D-galactopyranosyl-(1-3)-O-[α-L-fucopyranosyl-(1-4)-O-]-2-acetamido-2-deoxy-β-D-glucopyranoside 18l Tetrasaccharide 18a (0.003 g) was applied on Dowex 50×8 (Na+ form) resin and eluted with water. The appropriate fractions, were freeze-dried, followed by further drying over phosphorous pentoxide. Methyl iodide (0.050 mL) was added to the residue dissolved in dimethyl sulfoxide. After stirring in the dark for 20 hours, the solution was evaporated in vacuo, diluted with water (11 mL) and applied to a Sep-Pak Cls cartridge. After washing with water (10 mL), the product was eluted with methanol. Evaporation of the appropriate fractions left a residue which was chromatographed on Iatrobeads (0.5 g) using a 65:35:5 mixture of chloroform: methanol:water providing the methyl ester of compound 18a (0.025 g): $^1$H-n.m.r.: 5,099 (d, 1H, $J_{1,2}$ 3.75 Hz, H-1 αFUC), 4.517 (d, 2H, $J_{1,2}$ 7.5 Hz, H-1 βGal and βGlcNAc), 3,866 and 3.683 (2s, $CO_2CH_3$), 2.781 (dd, 1H, $J_{3ax,3eq}$ 12.5Hz, $J_{3eq,4}$ 4.5Hz, H-3eq Neu5Ac), 2,032 and 2,018 (2s, 6H, 2 NAc), 1,913 (dd, 1H, $J_{3ax,4}$ 12.5 Hz, H-3ax Neu5Ac), 1,160 (d, 3H, $J_{5,6}$ 6.5 Hz, H-6 αFuc).

This material was heated at 50° C. in a 40% solution of N-methylamine (1 mL) for 3.5 hours. After evaporation in vacuo, the residue was dissolved in water (1 mL) and applied on a Sep-Pak cartridge which was further washed with water. After elution of the product with methanol, the solvent was evaporated and the residue freeze-dried from water providing 18l (0.0025 g); $^1$H-n.m.r.: (Table E).

F. SYNTHESIS OF ARTIFICIAL ANTIGENS BY SIALYLATION WITH A SIALYLTRANSFERASE OF AN ANTIGENIC CARRIER CONTAINING ONE OR MORE OLIGOSACCHARIDE GROUPS COMPATIBLE WITH SAID SIALYLTRANSFERASE

Oligosaccharide glycosides containing an appropriate functional group in the glycoside moiety were conjugated to antigenic carriers containing one or more complementary functional groups following procedures known in the art.

Specifically, the conjugation of the oligosaccharide glycosides such as structures 4b, 5b, 6a and 7a to BSA, KLH or other carriers is achieved by procedures such as the "acyl-azide" procedure of Lemieux et al. and Pinto et al.[65,66].

The conjugates are then sialylated with an enzyme of appropriate specificity by a procedure similar to that reported in Example 10 above and the products purified by a combination of ultra-filtration and Gel-filtration.

FIG. 12 illustrates the reaction schemes employed to prepare such artificial antigens.

EXAMPLE 14

Enzymatic Transfer of an Analogue of Sialic Acid to an Antigenic Carrier

Bovine serum albumin was linked to oligosaccharide glycoside 4b by the "acyl-azide" procedure of Lemieux et al. and Pinto et al.[65,66] leading to the conjugate 20a using 0.22 μmol of oligosaccharide glycoside 4b for 1 mg of BSA. 12 mg of the resulting conjugate, 20a, was combined with 3 mg of CMP-9-d-Neu5Ac, 2c, and 5 mU of βGal(1→$\frac{3}{4}$)βGlcNAc-α(2→3)sialyltransferase and incubated at 37° C. in 2 mL of 50 mM sodium cocodylate buffer at pH 6.5 which additionally contains 0.5% by weight Triton CF-54 (available from Rohm & Haas, Philadelphia, Pa.) and 1 mg/ml BSA. After 24 hours, 3 mg of additional CMP-9-d-Neu5Ac, 2c, and sialyltransferase (5 mU) were added to the reaction mixture. The resulting mixture was incubated for an additional 24 hours to yield an artificial antigen, 21c, which contains one or more alpha sialylated oligosaccharide groups bound to the BSA. This product was then purified by ultra filtration on an Amicon PM10 membrane. The residue was dissolved in water (3 ml), applied to a column of Sephadex LH-20 (1.0×70 cm) and the product eluted with water. The fractions containing the product, 21c, (as judged by adsorbency at 280 nm) were pooled and lyophilized to yield 13 mg of product.

The results of this example as well as other examples of artificial antigens prepared in a manner similar to Example 14 are set forth in Table J below:

TABLE J

| Oligosac. glycoside | Antigenic Carrier | Conj | Incorp A (1) | CMP-Sialic Acid | Enz. | Artif. Antig. |
|---|---|---|---|---|---|---|
| 4b | BSA | 20a | 0.22 | 2c | (3) | 21c |
| 5b | BSA | 20b | 0.12 | 2c | (4) | 22c |

TABLE J-continued

| Oligosac. glycoside | Antigenic Carrier | Conj | Incorp A (1) | CMP-Sialic Acid | Enz. | Artif. Antig. |
|---|---|---|---|---|---|---|
| 5b | BSA | 20b | 0.12 | 2d | (4) | 22d |

1. phenol sulphuric assay
2. micro thiobarbituric assay (μmol of sialic acid per mg of artificial antigen)
3. βGal(1 → 3)βGlcNAc-α(2 → 3)sialyltransferase
4. βGal(1 → 4)βGlcNAc-α(2 → 6)sialyltransferase Oligosac. glycoside = oligosaccharide glycoside
Conj = conjugate of oligosaccharide glycoside and antigenic carrier
Incorp A = μmol of oligosaccharide glycoside incorporated onto the antigenic carrier per mg of conjugate
Incorp B = μmol of sialic acid incorporated onto the antigenic carrier per mg of artificial antigen
Enz. = enzyme
Artif. Antig. = Artificial Antigen Similarly, by following the procedures set forth in Example 14 above, other antigenic carriers can be used to create artificial antigens including KLH, human serum albumin (HSA), diphtheria or tetanus toxins, S-layers, and the like. Likewise, other compatible oligosaccharide glycosides could be coupled to the antigenic carriers used in place of the oligosaccharide glycosides employed above. Sialyltransferases compatible with the oligosaccharide glycosides could also be used. Additionally, other CMP derivatives of analogues of sialic acid compatible with the sialyltransferase could be employed.

F. SYNTHESIS OF ARTIFICIAL ANTIGENS BY COUPLING ONE OR MORE ALPHA SIALYLATED OLIGOSACCHARIDE GLYCOSIDES TO AN ANTIGENIC CARRIER

Alpha sialylated oligosaccharide glycosides containing an appropriate functional group in the glycoside moiety can be conjugated to antigenic carriers containing one or more complementary functional groups following procedures known in the art. For example, an alpha sialylated oligosaccharide glycoside containing a $-(CH_2)_nCO_2CH_3$ aglycon can be modified by reaction with hydrazine and $N_2O_4$ to convert the ester ($COOCH_3$) to a carbonyl azide ($-C(O)N_3$). The azide is then displaced by reaction with an amino functionality on the antigenic carrier resulting in linking of the alpha sialylated oligosaccharide glycoside to the carrier via an amide bond. Because the carrier can contain numerous amine groups, the carrier is capable of adding more than one alpha sialylated oligosaccharide glycoside. FIG. 13 illustrates the reaction scheme involved in the formation of these artificial antigens.

G. SYNTHESIS OF CARRIERS CONTAINING ALPHA SIALYLATED OLIGOSACCHARIDE GLYCOSIDES

Copolymers incorporating oligosaccharide glycosides can be synthesized by methods known in the art from appropriately functionalized glycosides and polymerizable monomers[s°]. In the following example, the oligosaccharide glycoside or saccharide unit is synthesized to contain a polymerizable functional group, such as an ethylenic bond, particularly an activated double bond such as that of compounds 4c and 37, i.e., having a $-(CH_2)_5OCH_2CH{=}CH_2$ aglycon group. Such compounds are then used to synthesize copolymers which incorporate one or more oligosaccharide groups.

The copolymer so formed is then used as an acceptor structure for a compatible sialyltransferase and a compatible analogue of sialic acid which is then transferred to such groups so as to provide for a copolymer containing one or more alpha sialylated oligosaccharide glycosides.

FIGS. 14 and 15 illustrate reaction scheme for the synthesis of these copolymers.

EXAMPLE 15

Synthesis of a Copolymer Containing One or More Alpha Sialylated Oligosaccharide Glycoside A. An appropriate amount of compound 4c is combined in water with acrylamide in the presence of an initiator system as described in the art.[80] The product is purified by appropriate techniques such as ultrafiltration on PM10 membrane and gel chromatography on Sephadex LH20 leading to copolymer 23: $^1$H-n.m.r.: 4,559 (d, 1d, J 7.7 Hz) and 4.440 (d, J 7.5 Hz): H-1 and H-1', 2.053 (s, NAc); incorporation 0.44 μmol/mg.

B. Copolymer 23 (10 mg, 0.44 μmol/mg), CMP-9-$N_3$-Neu5Ac 2b (1 equivalent), βGal(1→¾)βGlcNAc-α(2→3')sialyltransferase (10–15 mU) are incubated in a plastic tube at 37° C. in 50 mM sodium cacodylate buffer (pH 6.5, 2 mL) containing 0.5 % Triton CF-54 (available from Rohm & Haas, Philadelphia, PA) and serum albumin ( 1 mg/mL). After 24 hours, more CMP-derivative ( 1.0 equivalent) and sialyltransferase (5–10 mU) are added. After 48 hours, the reaction is stopped and the product purified as indicated above leading to copolymer 24 (10 mg): $\alpha_D^{20}-2.43$ (c. 0.37, $H_2O$); $^1$H-n.m.r.: 4. 567 (d, J 7.5 Hz) and 4. 491 (d, J 7.7 Hz): H-1 and H-1' 4.074 (dd, 1H, $J_{2',3'}$10.0, $J_{3',4'}$ 2.8 Hz, H-3'), 2.760 (dd, 1H, $J_{3''eq,4''}$4.3) 2.036 (s, 2NAc).

Copolymers 27c and 27h were obtained in a similar manner by transfer of sialic acid from 2c and 2h respectively to copolymer 26 using the βGal (1→4) βGlcNAc-α(2→6) sialyltransferase. Physical data for these compounds are as follows:

Compound 27c: $\alpha_D^{20}=-5.52$ (c , 0.87, $H_2O$); $^1$H-n.m.r.: 4. 577 (d, $J_{3''eq,4''}$4.5, $J_{3''eq,3''ax}$ 12.5 Hz, H-3 "eq), 2.051 and 2.073 (two s, NAc), 1.285 (d, $J_{8'',9''}$6.0 Hz, H-9");

Compound 27h: 4.581 (d, J 7.5 Hz): H-1 and H-1' 4.141 (s, 2H, $CH_2CO$), 2.731 (dd, 1H, $J_{3''eq,3''ax}$ 12.5 Hz, H-3"dq), 2.077 (s, NAC).

In copolymers 24b, 27c, and 27h, the incorporation was calculated from the integral of the appropriate signals of the $^1$H-n.m.r. and further checked by the thiobarbituric assay for sialic assays.

EXAMPLE 16

Synthesis of a Copolymer Containing One or More Alpha Sialylated Oligosaccharide Glycoside A. An appropriate amount of compound 37 is combined in water with acrylamide in the presence of an initiator system as described in the art.[80] The product is purified by appropriate techniques such as ultrafiltration on PM10 membrane and gel chromatography on Sephadex LH20 leading to copolymer 25: $\alpha_D^{20}=-6.08$ (c, 1.43, $H_2O$); $^1$H-n.m.r.: 4.517 (d, J 8.5 Hz H-1), 2.041 (s, NAc); incorporation 0.5 μmol/mg.

B. Copolymer 25 (22 mg, 0.57 μmol/mg), UDP-galactose (2.0 equivalents), and bovine milk galactosyltransferase (EC 2.4.1.22, 1U), are incubated in sodium cacodylate buffer (pH 7.5, 2.0 mL) containing 20 mM manganese dichloride in a plastic tube at 30° C. After 10 hours, more UDP-galactose (1.0 equivalent) is added to the reaction mixture. After 24 hours, the reaction mixture is stopped by precipitation of the protein with phosphotungstic acid (0.1% in 0.5 N hydrochloric acid, 2 mL at 4° C., and centrifugation (10,000 g, 10 minutes). The clear supernatant was filtered through PM 10 membrane. After lyophilization, the residue was chromatographed on Sephadex LH20 leading to copolymer 26 (20 mg): $\alpha_D^{20}=-1.03$ (c 1.07, H2O); $^1$H-n.m.r.: 4.551 (d, J 7.0 Hz), 4.496 (d, J 7.7 Hz); H-1 and H-1' 2.053 (s, NAc); incorporation: 0.50 μmol/mg.

In Examples 15 A and 16 A, the incorporation of the carbohydrate moiety was calculated by using the integral of the appropriate signals in the $^1$H-n.m.r. spectrum and checked by the phenol-sulphuric assay.

G. SYNTHESIS OF AGGREGATES CONTAINING ALPHA SIALYLATED OLIGOSACCHARIDE GLYCOSIDES

Aggregates such as liposomes and micelles can be prepared so as to incorporate oligosaccharide glycosides. Specifically, incorporation of the oligosaccharide glycoside into such aggregates requires that the aglycon moiety be hydrophobic. Suitable hydrophobic groups include alkyl groups of at least 4 carbon atoms, $-(CH_2)_8COOCH_3$, and the like. In such aggregates, the hydrophobic aglycon group of the oligosaccharide glycoside becomes partitioned in the lipid portion of the aggregate whereas the oligosaccharide group is generally partitioned in the aqueous phase.

Methods of preparing such aggregates are well known in the art. See, for instance, U.S. Pat. No. 4,522,803 which is incorporated herein by reference.

Similarly, the methods of this invention can be used to prepare sialylated and monofucosylated derivatives of βGal(1-4)βGlcNAc(1-3)βGal(1-4)βGlcNAc-OR wherein the sialylating group is an analogue of sialic acid. Specific exemplification of the preparation of such derivatives is set forth in U.S. Ser. No. 07/771,259, filed Oct. 2, 1991, and entitled "METHODS FOR THE SYNTHETIS OF MONOFUCOSYLATED OLIGOSACCHARIDES TERMINATING IN DI—N-ACETYLLACTOSAMINYL STRUCTURES", now abandoned, which application is incorporated herein by reference in its entirety.

What is claimed is:

1. A method for the enzymatic synthesis of an alpha-sialylated oligosaccharide glycoside containing an analogue of sialic acid which method comprises the steps of:

a) selecting a sialyltransferase;

b) selecting a CMP-sialic acid analogue which is compatible with the sialyltransferase selected in, step a) and which is a derivative of a naturally occurring sialic acid;

c) contacting the selected CMP-sialic acid analogue with an oligosaccharide glycoside acceptor of the formula oligosaccharide-Y-R in the presence of the selected sialyltransferase under conditions whereby the sialic acid analogue is transferred from the selected CMP-sialic acid analogue to the non-reducing sugar terminus of the oligosaccharide glycoside acceptor so as to form an alpha-sialylated oligosaccharide glycoside containing an analogue of sialic acid wherein R represents an aglycon moiety containing at least one carbon atom with the proviso that R is neither hydrogen, a lipid or a protein, Y is selected from the group consisting of O, NH and S, and oligosaccharide is an oligosaccharide of from 2 to about 10 saccharide units in which the terminal saccharide units at the non-reducing sugar terminus of the oligosaccharide are compatible with the selected sialyltransferase.

2. The method of claim 1, wherein the CMP-sialic acid analogue is obtained by treating the sialic acid analogue with the enzyme CMP-sialic acid synthase.

3. The method of claim 1, wherein the aglycon moiety, R, is selected from the group consisting of —(A)—Z′ wherein A represents a bond, an alkylene group of from 2 to 10 carbon atoms, and a moiety of the form $-(CH_2-CR_2G)_n-$ wherein n is an integer equal to 1 to 5; $R_2$ is selected from the group consisting of hydrogen, methyl, and ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z′ is selected from the group consisting of hydrogen, methyl and, when G is not oxygen, sulphur or nitrogen and A is not a bond, then Z′ is also selected from the group consisting of —OH, —SH, $-NH_2$, $-NHR_3$, $-N(R_3)_2$, —C(O)OH, $-C(O)OR_3$, $-C(O)NH-NH_2$, $-C(O)NH_2$, $-C(O)NHR_3$, $-C(O)N(R_3)_2$, and $-OR_4$ wherein each $R_3$ is independently alkyl of from 1 to 4 carbon atoms and $R_4$ is an alkenyl group of from 3 to 10 carbon atoms.

4. The method of claim 1 wherein the aglycon moiety is a hydrophobic group of at least 2 carbon atoms.

5. The method of claim 4 wherein the aglycon moiety is a hydrophobic group selected from the group consisting of $-(CH_2)_8COOCH_3$ and $-(CH_2)_5OCH_2CH{=}CH_2$ and $-(CH_2)_8CH_2OH$.

6. A method for the preparation of an antigenic carrier having one or more alpha-sialylated oligosaccharide groups containing an analogue of sialic acid which groups are pendent to said carrier which method comprises the steps of:

a) selecting a sialyltransferase;

b) selecting a CMP-sialic acid analogue which is compatible with the sialyltransferase selected in step a) and which is a derivative of a naturally occurring sialic acid;

c) contacting the selected CMP-sialic acid analogue with an oligosaccharide glycoside acceptor of the formula oligosaccharide-Y-$R_1$ in the presence of the selected sialyltransferase under conditions whereby the sialic acid analogue is transferred from the selected CMP-sialic acid analogue to the non-reducing sugar terminus of the oligosaccharide glycoside acceptor so as to form an alpha-sialylated oligosaccharide glycoside containing an analogue of sialic acid wherein $R_1$ represents an aglycon moiety capable of being linked to an antigenic carrier with the proviso that $R_1$ is neither hydrogen, a lipid nor a protein, Y is selected from the group consisting of O, NH and S, and oligosaccharide is an oligosaccharide of from 2 to about 10 saccharide units in which the terminal saccharide units at the non-reducing terminus of the oligosaccharide are compatible with the selected sialyltransferase;

d) selecting an antigenic carrier having one or more functionalities capable of linking to the aglycon moiety of the alpha-sialylated oligosaccharide glycoside produced in step c) above;

e) linking one or more of said alpha-sialylated oligosaccharide glycosides containing an analogue of sialic acid, produced in step c) to the antigenic carrier selected in step d).

7. The method according to claim 6 wherein said CMP-sialic acid analogue is obtained by treating the sialic acid analogue with the enzyme CMP-sialic acid synthase.

8. A method according to claim 6 wherein $R_1$ is selected from the group consisting of —(A)—Z″ wherein A is selected from the group consisting of an alkylene group of from 2 to 10 carbon atoms and a moiety of the form $-(CH_2-CR_5G)_n-$ wherein n is an integer equal to 1 to 5; $R_5$ is selected from the group consisting of hydrogen, methyl, and ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z″ is selected from the group consisting of hydrogen and, when G is not oxygen, sulphur or nitrogen, then Z″ is also selected from the group consisting of —OH, —SH, $-NH_2$, $-NHR_6$, —C(O)OH, $-C(O)OR_6$, $-C(O)NHNH_2$, and $-OR_7$ wherein each $R_6$ is independently alkyl of from 1 to 4 carbon atoms and $R_7$ is an alkenyl group of from 3 to 10 carbon atoms with the proviso that when A is a bond, Z is not hydrogen.

9. A method according to claim 8 wherein the aglycon moiety, $R_1$, is a hydrophobic group selected from the group consisting of $-(CH_2)_8COOCH_3$, $-(CH_2)_5OCH_2CH{=}CH_2$ and $-(CH_2)_8CH_2OH$.

10. A method for the preparation of an antigenic carrier having one or more alpha-sialylated oligosaccharide groups containing an analogue of sialic acid which groups are pendent to said carrier which method comprises the steps of:

a) selecting a sialyltransferase;

b) selecting an oligosaccharide glycoside acceptor of the formula oligosaccharide-Y-$R_1$ wherein $R_1$ represents an aglycon moiety capable of being linked to an antigenic carrier with the proviso that $R_1$ is neither hydrogen, a lipid nor a protein, Y is selected from the group consisting of O, NH and S, and oligosaccharide is an oligosaccharide of from 2 to about 10 saccharide units in which the terminal saccharide units at the non-reducing terminus of the oligosaccharide are compatible with the selected sialyltransferase:

c) selecting an antigenic carrier having one or more functionalities capable of linking to the aglycon moiety of the selected oligosaccharide glycoside acceptor;

d) linking at least one said oligosaccharide glycoside acceptor to said carrier selected in step c) to form oligosaccharide groups pendant to the antigenic carrier;

e) selecting a CMP-sialic acid analogue which is compatible with the sialyltransferase selected in step a) and which is a derivative of a naturally occurring sialic acid;

f) contacting the selected CMP-sialic acid analogue with the antigenic carrier produced in step d) above in the presence of the selected sialyltransferase under conditions whereby the sialic acid analogue is transferred from the selected CMP-sialic acid analogue to the non-reducing sugar terminus of the oligosaccharide group(s) pendant to the antigenic carrier so as to form an antigenic carrier having one or more alpha sialylated oligosaccharide groups containing an analogue of sialic acid pendant to said carrier.

11. The method according to claim 10 wherein said CMP-sialic acid analogue is obtained by treating the sialic acid analogue with the enzyme CMP-sialic acid synthase.

12. A method according to claim 10 wherein $R_1$ is selected from the group consisting of —(A)—Z″ wherein A is selected from the group consisting of an alkylene group of from 2 to 10 carbon atoms and a moiety of the form $—(CH_2—CR_5G)_n—$ wherein n is an integer equal to 1 to 5; $R_5$ is selected from the group consisting of hydrogen, methyl, and ethyl; and G is selected from the group consisting of hydrogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z″ is selected from the group consisting of hydrogen and, when G is not oxygen, sulphur or nitrogen, then Z″ is also selected from the group consisting of —OH, —SH, $—NH_2$, $—NHR_6$, —C(O)OH, $—C(O)OR_6$, $—C(O)NHNH_2$, and $—OR_7$ wherein each $R_6$ is independently alkyl of from 1 to 4 carbon atoms and $R_7$ is an alkenyl group of from 3 to 10 carbon atoms with the proviso that when A is a bond, Z is not hydrogen.

13. The method according to claim 12 wherein aglycon moiety, $R_1$, is a hydrophobic group selected from the group consisting of $—(CH_2)_8COOCH_3$, $—(CH_2)_5OCH_2CH═CH_2$ and $—(CH_2)_8CH_2OH$.

14. The method according to claim 1 wherein the selected sialyltransferase is $\beta$Gal(1$\frac{3}{4}$)$\beta$GlcNAc $\alpha$(2-3)sialyltransferase and the oligosaccharide glycoside acceptor contains a disaccharide group on the nonreducing terminus which group is selected from the group consisting of $\beta$Gal(1-3)$\beta$GlcNAc-, $\beta$Gal(1-4)$\beta$GlcNAc-, and $\beta$Gal(1-4)$\beta$Glc-.

15. The method according to claim 1 wherein the selected sialyltransferase is $\beta$Gal(1-4)$\beta$GlcNAc $\alpha$(2-6)sialyltransferase and the oligosaccharide glycoside acceptor contains a $\beta$Gal(1-4)$\beta$GlcNAc- disaccharide group on the nonreducing terminus.

16. The method according to claim 1 wherein the selected sialyltransferase is $\beta$Gal(l-3)eGalNAc $\alpha$(2-3)sialyltransferase and the oligosaccharide glycoside acceptor contains a $\beta$Gal(1-3)$\beta$GalNAc- disaccharide group on the nonreducing terminus.

17. The method according to claim 1 wherein said contacting step (c) is conducted at a temperature of from 25° to 45° C.; for a period of time of from 12 hours to 4 days; and at a pH of from about 6.5 to 7.5.

* * * * *